US008173141B2

(12) United States Patent
Cox et al.

(10) Patent No.: US 8,173,141 B2
(45) Date of Patent: *May 8, 2012

(54) IMMUNOGENIC COMPLEXES AND METHODS RELATING THERETO

(75) Inventors: John Cooper Cox, Bullengarook (AU); Debbie Pauline Drane, Bullengarook (AU); Andreas Suhrbier, Bunya (AU)

(73) Assignee: CSL Limited, Parkville, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 12/458,116

(22) Filed: Jul. 1, 2009

(65) Prior Publication Data

US 2010/0010193 A1 Jan. 14, 2010

Related U.S. Application Data

(63) Continuation of application No. 09/506,011, filed on Feb. 17, 2000, now Pat. No. 7,776,343.

(30) Foreign Application Priority Data

Feb. 17, 1999 (AU) .......................................... PP8735
Jul. 27, 1999 (AU) ....................................... PQ1861

(51) Int. Cl.
*A61K 47/00* (2006.01)
(52) U.S. Cl. ........................... 424/278.1; 424/9.2; 204/1
(58) Field of Classification Search .................. None
See application file for complete search history.

(56) References Cited

U.S. PATENT DOCUMENTS

| | | | |
|---|---|---|---|
| 4,469,863 A | 9/1984 | Ts'o et al. |
| 4,578,269 A | 3/1986 | Morein |
| 4,981,684 A | 1/1991 | MacKenzie et al. |
| 5,023,243 A | 6/1991 | Tullis |
| 5,057,540 A | 10/1991 | Kensil et al. |
| 5,177,198 A | 1/1993 | Spielvogel et al. |
| 5,178,860 A | 1/1993 | MacKenzie et al. |
| 5,273,965 A | 12/1993 | Kensil et al. |
| 5,284,656 A | 2/1994 | Platz et al. |
| 5,443,534 A | 8/1995 | Vinciarelli et al. |
| 5,443,829 A | 8/1995 | Kensil et al. |
| 5,451,569 A | 9/1995 | Wong et al. |
| 5,583,112 A | 12/1996 | Kensil et al. |
| 5,612,030 A | 3/1997 | Chatterjee et al. |
| 5,650,398 A | 7/1997 | Kensil et al. |
| 5,663,153 A | 9/1997 | Hutcherson et al. |
| 5,679,354 A | 10/1997 | Morein et al. |
| 5,716,848 A | 2/1998 | Dalsgard et al. |
| 5,723,335 A | 3/1998 | Hutcherson et al. |
| 5,780,448 A | 7/1998 | Davis |
| 5,859,231 A | 1/1999 | Shaw et al. |
| 5,897,873 A | 4/1999 | Popescu |
| 5,977,081 A | 11/1999 | Marciani |
| 6,027,732 A | 2/2000 | Morein et al. |
| 6,080,725 A | 6/2000 | Marciani |
| 6,160,109 A | 12/2000 | Just et al. |
| 6,190,870 B1 | 2/2001 | Schmitz et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,221,882 B1 | 4/2001 | Macfarlane |
| 6,231,859 B1 | 5/2001 | Kensil |
| 6,239,116 B1 | 5/2001 | Krieg et al. |
| 6,251,603 B1 | 6/2001 | Jager et al. |
| 6,339,068 B1 | 1/2002 | Krieg et al. |
| 6,352,697 B1 | 3/2002 | Cox et al. |
| 6,355,244 B1 | 3/2002 | Foon et al. |
| 6,399,630 B1 | 6/2002 | Macfarlane |
| 6,406,705 B1 | 6/2002 | Davis et al. |
| 6,429,199 B1 | 8/2002 | Krieg et al. |
| 6,479,504 B1 | 11/2002 | Macfarlane et al. |
| 6,521,637 B2 | 2/2003 | Macfarlane |
| 6,558,670 B1 | 5/2003 | Friede et al. |
| 6,610,308 B1 | 8/2003 | Haensler |
| 6,610,661 B1 | 8/2003 | Carson et al. |
| 6,639,814 B2 | 10/2003 | Gan et al. |
| 6,653,292 B1 | 11/2003 | Krieg et al. |
| 6,727,230 B1 | 4/2004 | Hutcherson et al. |
| 6,821,957 B2 | 11/2004 | Krieg et al. |
| 6,835,395 B1 | 12/2004 | Semple et al. |
| 6,881,821 B2 | 4/2005 | Simmonds et al. |
| 6,943,240 B2 | 9/2005 | Bauer et al. |
| 6,949,520 B1 | 9/2005 | Hartmann et al. |
| 7,001,890 B1 | 2/2006 | Wagner et al. |
| 7,049,302 B1 | 5/2006 | Kensil |

(Continued)

FOREIGN PATENT DOCUMENTS

EP  0 180 564 B1  5/1986

(Continued)

OTHER PUBLICATIONS

Morein et al., "Functional aspects of isocoms," *Immunology & Cell Biology*, vol. 76, 1998, pp. 295-299.
Coulter et al., "Studies on experimental adjuvanted influenza vaccines: comparison of immune stimulating complexes (Iscoms™) and oil-in-water vaccines," *Vaccine*, 1997, pp. 1243-1253, vol. 16, No. 11/12, Elsevier Science Ltd., Great Britain.
Dass et al., Immunostimulatory activity of cationic-lipid-nucleic-acid complexes against cancer. J Cancer Res Clin Oncol. Apr. 2002; 128(4): 177-81.
Evans et al., The use of ISCOMATRIX adjuvant for delivery of CpG 7909. Jul. 2004 Meeting. Poster and Abstract.
Gouttefangeas et al., Problem solving for tumor immunotherapy. Nat Biotechnol. May 2000; 18(5):491-2.
Gregoriadis et al. (Eds.), *Vaccine Design, The Role of Cytokine Networks*, 1996, Table of Contents Only, Plenum Press.
Grossmann et al., Avoiding tolerance against prostatic antigens with subdominant peptide epitopes. J Immunother. May-Jun. 2001; 24(3):237-41.

(Continued)

*Primary Examiner* — Agnieszka Boesen
(74) *Attorney, Agent, or Firm* — Foley & Lardner LLP

(57) ABSTRACT

The present invention relates generally to an immunogenic complex comprising a charged organic carrier and a charged antigen and, more particularly, a negatively charged organic carrier and a positively charged antigen. The complexes of the present invention are useful, inter alia, as therapeutic and/or prophylactic agents for facilitating the induction of a cytotoxic T-lymphocyte response to an antigen.

17 Claims, 48 Drawing Sheets

U.S. PATENT DOCUMENTS

| | | | |
|---|---|---|---|
| 7,198,892 B2 | 4/2007 | Simmonds et al. | |
| 7,776,343 B1 * | 8/2010 | Cox et al. | 424/278.1 |
| 2001/0044416 A1 | 11/2001 | McCluskie et al. | |
| 2002/0065236 A1 | 5/2002 | Yew et al. | |
| 2002/0091097 A1 | 7/2002 | Bratzler et al. | |
| 2002/0164341 A1 | 11/2002 | Davis et al. | |
| 2002/0192184 A1 | 12/2002 | Carpentier et al. | |
| 2003/0026801 A1 | 2/2003 | Weiner et al. | |
| 2003/0050261 A1 | 3/2003 | Krieg et al. | |
| 2003/0050268 A1 | 3/2003 | Krieg et al. | |
| 2003/0059937 A1 | 3/2003 | Ruben et al. | |
| 2003/0091599 A1 | 5/2003 | Davis et al. | |
| 2003/0100527 A1 | 5/2003 | Krieg et al. | |
| 2003/0104523 A1 | 6/2003 | Bauer et al. | |
| 2003/0118635 A1 | 6/2003 | Dalsgaard et al. | |
| 2003/0139364 A1 | 7/2003 | Kreig et al. | |
| 2003/0148316 A1 | 8/2003 | Lipford et al. | |
| 2003/0148976 A1 | 8/2003 | Krieg et al. | |
| 2003/0175884 A1 | 9/2003 | Umana et al. | |
| 2003/0181406 A1 | 9/2003 | Schetter et al. | |
| 2003/0191079 A1 | 10/2003 | Kreig et al. | |
| 2003/0212026 A1 | 11/2003 | Krieg et al. | |
| 2003/0224010 A1 | 12/2003 | Davis et al. | |
| 2003/0232074 A1 | 12/2003 | Lipford et al. | |
| 2003/0232856 A1 | 12/2003 | Macfarlane | |
| 2004/0009949 A1 | 1/2004 | Krieg | |
| 2004/0030118 A1 | 2/2004 | Wagner et al. | |
| 2004/0038922 A1 | 2/2004 | Haensler et al. | |
| 2004/0047869 A1 | 3/2004 | Garcon et al. | |
| 2004/0053880 A1 | 3/2004 | Krieg | |
| 2004/0067902 A9 | 4/2004 | Bratzler et al. | |
| 2004/0067905 A1 | 4/2004 | Krieg | |
| 2004/0087534 A1 | 5/2004 | Krieg et al. | |
| 2004/0087538 A1 | 5/2004 | Krieg et al. | |
| 2004/0092472 A1 | 5/2004 | Krieg | |
| 2004/0106568 A1 | 6/2004 | Krieg et al. | |
| 2004/0131628 A1 | 7/2004 | Bratzler et al. | |
| 2004/0132685 A1 | 7/2004 | Krieg et al. | |
| 2004/0142469 A1 | 7/2004 | Krieg et al. | |
| 2004/0143112 A1 | 7/2004 | Krieg et al. | |
| 2004/0147468 A1 | 7/2004 | Krieg et al. | |
| 2004/0152649 A1 | 8/2004 | Krieg | |
| 2004/0152656 A1 | 8/2004 | Krieg et al. | |
| 2004/0152657 A1 | 8/2004 | Krieg et al. | |
| 2004/0162258 A1 | 8/2004 | Krieg et al. | |
| 2004/0162262 A1 | 8/2004 | Krieg et al. | |
| 2004/0167089 A1 | 8/2004 | Krieg et al. | |
| 2004/0171150 A1 | 9/2004 | Krieg et al. | |
| 2004/0171571 A1 | 9/2004 | Krieg et al. | |
| 2004/0181045 A1 | 9/2004 | Krieg et al. | |
| 2004/0191270 A1 | 9/2004 | Drane et al. | |
| 2004/0198680 A1 | 10/2004 | Krieg | |
| 2004/0198688 A1 | 10/2004 | Krieg et al. | |
| 2004/0229835 A1 | 11/2004 | Krieg et al. | |
| 2004/0234512 A1 | 11/2004 | Wagner et al. | |
| 2004/0235770 A1 | 11/2004 | Davis et al. | |
| 2004/0235774 A1 | 11/2004 | Bratzler et al. | |
| 2004/0235777 A1 | 11/2004 | Wagner et al. | |
| 2004/0235778 A1 | 11/2004 | Wagner et al. | |
| 2004/0247662 A1 | 12/2004 | Dow et al. | |
| 2004/0266719 A1 | 12/2004 | McCluskie et al. | |
| 2005/0004061 A1 | 1/2005 | Krieg et al. | |
| 2005/0004062 A1 | 1/2005 | Krieg et al. | |
| 2005/0009774 A1 | 1/2005 | Krieg et al. | |
| 2005/0013812 A1 | 1/2005 | Dow et al. | |
| 2005/0031638 A1 | 2/2005 | Dalemans et al. | |
| 2005/0032734 A1 | 2/2005 | Davis et al. | |
| 2005/0032736 A1 | 2/2005 | Krieg et al. | |
| 2005/0037403 A1 | 2/2005 | Krieg et al. | |
| 2005/0037985 A1 | 2/2005 | Krieg et al. | |
| 2005/0043529 A1 | 2/2005 | Davis et al. | |
| 2005/0049215 A1 | 3/2005 | Krieg et al. | |
| 2005/0049216 A1 | 3/2005 | Krieg et al. | |
| 2005/0054601 A1 | 3/2005 | Wagner et al. | |
| 2005/0054602 A1 | 3/2005 | Krieg et al. | |
| 2005/0059619 A1 | 3/2005 | Krieg et al. | |
| 2005/0059625 A1 | 3/2005 | Krieg et al. | |
| 2005/0070491 A1 | 3/2005 | Krieg et al. | |
| 2005/0075302 A1 | 4/2005 | Hutcherson et al. | |
| 2005/0079152 A1 | 4/2005 | Bot et al. | |
| 2005/0100983 A1 | 5/2005 | Bauer et al. | |
| 2005/0101554 A1 | 5/2005 | Krieg et al. | |
| 2005/0101557 A1 | 5/2005 | Krieg et al. | |
| 2005/0119273 A1 | 6/2005 | Lipford et al. | |
| 2005/0123523 A1 | 6/2005 | Krieg et al. | |
| 2005/0130911 A1 | 6/2005 | Uhlmann et al. | |
| 2005/0148537 A1 | 7/2005 | Krieg et al. | |
| 2005/0169888 A1 | 8/2005 | Hartman et al. | |
| 2005/0171047 A1 | 8/2005 | Krieg et al. | |
| 2005/0181035 A1 | 8/2005 | Dow et al. | |
| 2005/0181422 A1 | 8/2005 | Bauer et al. | |
| 2005/0182017 A1 | 8/2005 | Krieg | |
| 2005/0197314 A1 | 9/2005 | Krieg et al. | |
| 2005/0215500 A1 | 9/2005 | Krieg et al. | |
| 2005/0215501 A1 | 9/2005 | Lipford et al. | |
| 2005/0222072 A1 | 10/2005 | Wang et al. | |
| 2005/0233995 A1 | 10/2005 | Krieg et al. | |
| 2005/0233999 A1 | 10/2005 | Krieg et al. | |
| 2005/0239732 A1 | 10/2005 | Krieg et al. | |
| 2005/0239733 A1 | 10/2005 | Lurk et al. | |
| 2005/0239734 A1 | 10/2005 | Uhlmann et al. | |
| 2005/0239736 A1 | 10/2005 | Krieg et al. | |
| 2005/0244379 A1 | 11/2005 | Krieg et al. | |
| 2005/0244380 A1 | 11/2005 | Krieg et al. | |
| 2005/0245477 A1 | 11/2005 | Krieg et al. | |
| 2005/0250726 A1 | 11/2005 | Krieg et al. | |
| 2005/0256073 A1 | 11/2005 | Lipford et al. | |
| 2005/0267057 A1 | 12/2005 | Krieg | |
| 2005/0267064 A1 | 12/2005 | Krieg et al. | |
| 2005/0277604 A1 | 12/2005 | Krieg et al. | |
| 2005/0277609 A1 | 12/2005 | Krieg et al. | |
| 2006/0003955 A1 | 1/2006 | Krieg et al. | |
| 2006/0003962 A1 | 1/2006 | Ahluwalia et al. | |
| 2006/0019916 A1 | 1/2006 | Krieg et al. | |
| 2006/0019923 A1 | 1/2006 | Davis et al. | |
| 2006/0058251 A1 | 3/2006 | Krieg et al. | |
| 2006/0089326 A1 | 4/2006 | Krieg et al. | |
| 2006/0094683 A1 | 5/2006 | Krieg et al. | |
| 2006/0140875 A1 | 6/2006 | Krieg et al. | |
| 2006/0154890 A1 | 7/2006 | Bratzler et al. | |
| 2006/0172966 A1 | 8/2006 | Lipford et al. | |
| 2006/0188913 A1 | 8/2006 | Krieg et al. | |
| 2006/0210555 A1 | 9/2006 | Kensil et al. | |
| 2006/0211639 A1 | 9/2006 | Bratzler et al. | |
| 2006/0211644 A1 | 9/2006 | Krieg et al. | |
| 2006/0229271 A1 | 10/2006 | Krieg et al. | |
| 2006/0241076 A1 | 10/2006 | Uhlmann et al. | |
| 2006/0246035 A1 | 11/2006 | Ahluwalia et al. | |
| 2006/0286070 A1 | 12/2006 | Hartmann et al. | |
| 2006/0287263 A1 | 12/2006 | Davis et al. | |
| 2007/0037767 A1 | 2/2007 | Bratzler et al. | |
| 2007/0065467 A1 | 3/2007 | Krieg et al. | |
| 2007/0066554 A1 | 3/2007 | Krieg et al. | |
| 2007/0078104 A1 | 4/2007 | Krieg et al. | |
| 2007/0184465 A1 | 8/2007 | Wagner et al. | |
| 2007/0190072 A1 | 8/2007 | Cebon et al. | |
| 2007/0224210 A1 | 9/2007 | Krieg et al. | |
| 2007/0232622 A1 | 10/2007 | Lipford et al. | |
| 2008/0031936 A1 | 2/2008 | Krieg et al. | |
| 2009/0017021 A1 | 1/2009 | Davis et al. | |

FOREIGN PATENT DOCUMENTS

| | | |
|---|---|---|
| EP | 0 109 942 B1 | 3/1991 |
| EP | 0 231 039 B1 | 1/1992 |
| EP | 0468520 A2 | 1/1992 |
| EP | 0 092 574 B1 | 4/1992 |
| JP | 7-242554 | 9/1995 |
| WO | WO 89/11296 A1 | 11/1989 |
| WO | WO 90/01947 | 3/1990 |
| WO | WO 90/03184 A1 | 4/1990 |
| WO | WO 94/25602 A1 | 11/1994 |
| WO | WO 95/01363 A1 | 1/1995 |
| WO | WO 95/09179 A1 | 4/1995 |
| WO | WO 96/02555 A1 | 2/1996 |
| WO | WO 96/04385 | 2/1996 |
| WO | WO 96/11711 | 4/1996 |
| WO | WO 96/33739 A1 | 10/1996 |

| | | |
|---|---|---|
| WO | WO 98/15287 | 4/1998 |
| WO | WO 98/18810 A1 | 5/1998 |
| WO | WO 98/22135 A1 | 5/1998 |
| WO | WO 98/36772 A1 | 8/1998 |
| WO | WO 98/40100 | 9/1998 |
| WO | WO 99/11241 | 3/1999 |
| WO | WO 99/12565 | 3/1999 |
| WO | WO 99/53938 | 10/1999 |
| WO | WO 99/56755 A1 | 11/1999 |
| WO | WO 99/59578 A1 | 11/1999 |
| WO | WO 99/61056 | 12/1999 |
| WO | WO 99/61056 A2 | 12/1999 |
| WO | WO 00/03745 | 1/2000 |
| WO | WO 00/06588 A1 | 2/2000 |
| WO | WO 00/07621 | 2/2000 |
| WO | WO 00/09159 A1 | 2/2000 |
| WO | WO 00/14217 A2 | 3/2000 |
| WO | WO 00/15256 A2 | 3/2000 |
| WO | WO 00/41720 A1 | 7/2000 |
| WO | WO 00/48360 | 8/2000 |
| WO | WO 00/54803 A2 | 9/2000 |
| WO | WO 00/62800 A2 | 10/2000 |
| WO | WO 00/67787 A2 | 11/2000 |
| WO | WO 00/72876 A2 | 12/2000 |
| WO | WO 00/75304 A1 | 12/2000 |
| WO | WO 01/07917 A1 | 2/2001 |
| WO | WO 01/15727 | 3/2001 |
| WO | WO 01/15727 A2 | 3/2001 |
| WO | WO 01/22972 | 4/2001 |
| WO | WO 01/22990 A2 | 4/2001 |
| WO | WO 01/35991 A2 | 5/2001 |
| WO | WO 01/37879 A1 | 5/2001 |
| WO | WO 01/45750 A1 | 6/2001 |
| WO | WO 01/51083 | 7/2001 |
| WO | WO 01/51083 A2 | 7/2001 |
| WO | WO 01/62909 A1 | 8/2001 |
| WO | WO 02/28428 A2 | 4/2002 |
| WO | WO 02/32450 A2 | 4/2002 |
| WO | WO 03/040299 A2 | 5/2003 |
| WO | WO 2004/007743 A2 | 1/2004 |
| WO | WO 2004/026888 A2 | 4/2004 |
| WO | WO 2004/039950 A2 | 5/2004 |
| WO | WO 2004/094671 A2 | 11/2004 |
| WO | WO 2005/004910 A2 | 1/2005 |
| WO | WO 2005/026370 A2 | 3/2005 |
| WO | WO 2005/033278 A2 | 4/2005 |
| WO | WO 2007/026190 A2 | 3/2007 |

OTHER PUBLICATIONS

Hartmann et al., "CpG DNA: A potent signal for growth, activation, and maturation of human dendritic cells," Proc. Natl. Acad. Sci. USA, Aug. 1999, pp. 9305-9310, vol. 96.
Hartmann et al., J. Immunol., vol. 164, 2000, pp. 1617-1624.
Liu et al., CpG ODN is an effective adjuvant in immunization with tumor antigen. J Invest Med. Sep. 7, 1997; 45(7):333A.
O'Hagan et al., Recent developments in vaccine delivery systems. Curr Drug Targets Infect Disord. Nov. 2001; 1(3):273-86.
Singh et al., Recent advances in vaccine adjuvants. Pharm Res. Jun. 2002; 19(6):715-28.
Singh et al., Recent advances in veterinary vaccine adjuvants. Int J Parasitol. May 2003; 33(5-6):469-78.
Bomford et al., 1992, "Adjuvanticity and ISCOM Formation by Structurally Diverse Saponins," Vaccine 10(9):572-7.
Bomford, 1982, "Studies on the Cellular Site of Action of the Adjuvant Activity of Saponin for Sheep Erythrocytes," Int. Arch. Allergy Appl. Immunol. 67(2):127-31.
Campbell et al., 1992, "Saponin," Res. Immunol. 143(5):526-30; discussion 577-8.
Coughlin et al., 1995, Adjuvant Activity of QS-21 for Experimental E. coli 018 Polysaccharide Vaccines, Vaccine 13(1); 17-21.
Dalsgaard, 1974, "Saponin Adjuvants. 3. Isolation of a Substance from Quillaja saponaria Molina with Adjuvant Activity in Food-and-Mouth Disease Vaccines," Arch. Gesamte. Virusforsch.. 44(3):243-54.
Estrada et al., 1998, "Adjuvant Action of Chenopodium quinoa Saponins on the Induction of Antibody Responses to Intragastric and Intranasal Administered Antigens in Mice", Comp. Immunol. Microbiol. Infect. Dis. 21(3):225-36.
Hancock et al, 1995, "Formulation of the Purified Fusion Protein of Respiratory Syncytial Virus with the Saponin QS-21 Induces Protective Immune Responses in Balb/c Mice that are similar to those generated by Experimental Infection," Vaccine 13(4):391-400.
Higuchi et al., 1987, "Structure of Desacylsaponins Obtained from the Bark of Quillaja saponaria," Phytochemistry 26:229-35.
Kensil et al., 1991, "Separation and Characterization of Saponins with Adjuvant Activity from Quillaja saponaria Molina Cortex," J. Immunol. 146(2):431-7.
Soltysik et al., 1993, "Adjuvant Activity of QS-21 Isomers," Ann. N.Y. Acad. Sci. 690:392-5.
Kensil et al., 1995, "Structural and Immunological Characterization of the Vaccine adjuvant QS-21," Vaccine Design: The Subunit and Adjuvant Approach, Powell and Nuwman eds., Plenum Press, New York.
Kersten et al., "Incorporation of the Major Outer Membrane Protein of Neisseria gonorrhoeae in Saponin-Lipid Complese (Isocoms); Chemuical Analysis, Some Structural Features, and Comparison of Their Immunogenicity with Three Other Antigen Delivery Systems," Infect. Immun. 56(2):432-8.
Lacaille-Dubois et al., 1996, "A Review of the Biological and Pharmacological Activities of Saponins," Phytomedicine vol. 2, 363-386.
Livingston et al., 1994, "Phase I Trial of Immunological Adjuvant QS-21 with a GM2 Granglioside-Keyhole Limpet Haemocyanin Conjugate Vaccine in Patients with Malignant Melanoma," Vaccine 12(14):1275-80.
Ma et al., "Impact of the Saponin Adjuvant QS-21 and Aluminum Hydroxide on the Immunogenicity of Recombinent OspA and OspB of Borrelia burgdorferi," Vaccine 12(10):925.
Newman et al., 1992, "Saponin Adjuvant Induction of Ovalbumin-Specific CD8+ Cytotoxic T Lymphocyte Responses," J. Immunol. 148(8):2357-62.
Soltysik et al., 1995, "Structure/function Studies of QS-21 Adjuvant: Assessment of Triterpene Aldehyde and Glucuronic Acid Roles in Adjuvant Function," Vaccine 13(15):1403-10.
White et al., 1991, "A Purified Saponin Acts as an Adjuvant for a T-independent Antigen," Immunobiology of Proteins and Peptides, vol. VI (Atassi ed.), Plenum Press, New York, 207-210.
Wu et al., 1992, "Saponin Adjuvant Enhancement of Antigen-Specific Immune Responses to an Experimental HIV-I Vaccine," J. Immunol. 148(5):1519-25.
Wu et al., 1994, "Accessory Cell Requirements for Saponin Adjuvant-Induced Class I MHC Antigen-Restricted Cytotoxic T-Lymphocytes," Cell. Immunol. 154(a):393-406.
Hitomi et al., "High Efficiency Prokaryotic Expression and Purification of a Portion of the Hepatitis C Core Protein and Analysis of the Immune Response to Recombinant Protein in BALB/c Mice," Viral Immunology, vol. 8, No. 2, 1995, pp. 109-119.
Khemka et al. "The Capacity of a Combined Liposomal Hepatitis B and C Vaccine to Stimulate Humoral and Cellular Responses in Mice," Viral Immunology, vol. 11, No. 2, 1998, pp. 73-78.
Lamonaca et al., "Conserved Hepatitis C Virus Sequences are Highly Immunogenic for CD4+ T Cells: Implications for Vaccine Development," Hepatology, vol. 30, No. 4, Oct. 1999, pp. 1088-1098.
Polakos et al., "Characterization of Hepatitis C Virus Core-Specific Immune Responses Primed in Rhesus macaques by a Nonclassical ISCOM Vaccine," Journal of Immunology, vol. 166, No. 5, Mar. 1, 2001, pp. 3589-3598.
Lee et al. "Identification of a Domain Containing B-Cell Epitopes in Hepatitis C Virus E2 Glycoprotein by Using Mouse Monoclonal Antibodies," Journal of Virology, vol. 73, No. 1, Jan. 1999, pp. 11-18.
Sjolander et al., Advanced Drug Delivery Reviews, vol. 34, Issues 2-3, Dec. 1, 1998, pp. 321-338.
Cerny et al., J. Clin. Invest., vol. 95, No. 2, Feb. 1995, pp. 521-530.
Cruse et al., Illustrated Dictionary of Immunology, 2nd edition, published on 2003 by CRC, pp. 577-578.
Selby et al., "Expression, identification and subcellular localization of the proteins encoded by the hepatitis C Viral genome", J. of General Virology, vol. 74, 1993, pp. 1103-1113.
Christie et al., Hepatology, vol. 30, No. 4, 1999, pp. 1037-1044.
Farci et al., Science, vol. 288, 2000, pp. 399-344.

Cooper et al., *Immunity*, vol. 10, 1999, pp. 439-449.
Agrawal et al., Chapter 19: Pharmacokinetics and bioavailability of antisense oligonucleotides following oral and colorectal administrations in experimental animals. 1998: 525-43.
Agrawal et al., Antisense oligonucleotides: towards clinical trials. Trends in Biotechnology, 1996; 14: 376-87.
Askew et al., CpG DNA induces maturation of dendritic cells with distinct effects on nascent and recycling MHC-II antigen-processing mechanisms. J Immunol. Dec. 15, 2000;165(12):6889-95.
Baral et al., Immunostimulatory CpG oligonucleotides enhance the immune response of anti-idiotype vaccine that mimics carcinoembryonic antigen. Cancer Immunol Immunother. May 2003; 52(5):317-27.
Carpentier et al., Successful treatment of intracranial gliomas in rat by oligodeoxynucleotides containing CpG motifs. Clin Cancer Res. Jun. 2000; 6(6):2469-73.
Choi et al., The level of protection against rotavirus shedding in mice following immunization with a chimeric VP6 protein is dependent on the route and the coadministered adjuvant. Vaccine. Mar. 15, 2002;20(13-14):1733-40.
Chu et al., CpG oligodeoxynucleotides act as adjuvants that switch on T helper 1 (Th1) immunity. J Exp Med. Nov. 17, 1997; 186(10):1623-31.
Cooper et al., Safety and immunogenicity of CPG 7909 injection as an adjuvant to Fluarix influenza vaccine. Vaccine. Aug. 13, 2004; 22(23-24):3136-43.
Crooke et al., Phosphorothioate Oligonucleotides. Therapeut Apps. 1995; ch5:63-84.
Daftarian et al., Two distinct pathways of immuno-modulation improve potency of p53 immunization in rejecting established tumors. Cancer Res. Aug. 1, 2004;64(15):5407-14.
Davila et al., Generation of antitumor immunity by cytotoxic T lymphocyte epitope peptide vaccination, CpG-oligodeoxynucleotide adjuvant, and CTLA-4 blockade. Cancer Res. Jun. 15, 2003; 63(12):3281-8.
Davis et al., CpG ODN is safe and highly effective in humans as adjuvant to HBV vaccine: Preliminary results of Phase I trial with CpG ODN 7909. Third Annual Conference on Vaccine Res. 2000. Abstract s25, No. 47.
Gallichan et al., Intranasal immunization with CpG oligodeoxynucleotides as an adjuvant dramatically increases IgA and protection against herpes simplex virus-2 in the genital tract. J Immunol. Mar. 1, 2001; 166(5):3451-7.
Garbi et al., CpG motifs as proinflammatory factors render autochthonous tumors permissive for infiltration and destruction. J Immunol. May 15, 2004; 172(10):5861-9.
Holmgren et al., Mucosal adjuvants and anti-infection and anti-immunopathology vaccines based on cholera toxin, cholera toxin B subunit and CpG DNA. Expert Rev Vaccines. Apr. 2003; 2(2):205-17.
Jakob et al., Activation of cutaneous dendritic cells by CpG-containing oligodeoxynucleotides: a role for dendritic cells in the augmentation of Th1 responses by immunostimulatory DNA. J Immunol. Sep. 15, 1998; 161(6):3042-9.
Jakob et al., Bacterial DNA and CpG-containing oligodeoxynucleotides activate cutaneous dendritic cells and induce IL-12 production: implications for the augmentation of Th1 responses. Int Arch Allergy Immunol. Feb.-Apr. 1999; 118(2-4):457-61.
Klinman et al., Immunotherapeutic applications of CpG-containing oligodeoxynucleotides. Drug News Perspect. Jun. 2000; 13(5):289-96.
Kovarik et al., CpG oligodeoxynucleotides can circumvent the Th2 polarization of neonatal responses to vaccines but may fail to fully redirect Th2 responses established by neonatal priming. J Immunol. Feb. 1, 1999; 162(3):1611-7.
Krieg et al., Applications of immune stimulatory CpG DNA for antigen-specific and antigen-nonspecific cancer immunotherapy. Eur J Canc. Oct. 1999; 35/Suppl4:S10. Abstract #14.
Krieg et al., Causing a commotion in the blood: immunotherapy progresses from bacteria to bacterial DNA. Immunol Today. Oct. 2000; 21(10):521-6.
Krieg et al., Enhancing vaccines with immune stimulatory CpG DNA. Curr Opin Mol Ther. Feb. 2001; 3(1): 15-24.
Krieg et al., Chapter 7: CpG oligonucleotides as immune adjuvants. Ernst Schering Research Found Workshop 2001; 30: 105-18.
Krieg, Immune effects and mechanisms of action of CpG motifs. Vaccine. Nov. 8, 2000; 19(6):618-22.
Krieg et al., Induction of systemic TH1-like innate immunity in normal volunteers following subcutaneous but not intravenous administration of CPG 7909, a synthetic B-class CpG oligodeoxynucleotide TLR9 agonist. J Immunother. Nov.-Dec. 2004; 27(6):460-71.
Kuramoto et al., Induction of T-cell-mediated immunity against MethA fibrosarcoma by intratumoral injections of a bacillus Calmette-Guerin nucleic acid fraction. Cancer Immunol Immunother. 1992; 34(5):283-8.
Lee et al., Immuno-stimulatory effects of bacterial-derived plasmids depend on the nature of the antigen in intramuscular DNA inoculations. Immunology. Jul. 1998; 94(3):285-9.
Lipford et al., CpG-containing synthetic oligonucleotides promote B and cytotoxic T cell responses to protein antigen: a new class of vaccine adjuvants. Eur J Immunol. Sep. 1997; 27(9):2340-4.
Lipford et al., Immunostimulatory DNA: sequence-dependent production of potentially harmful or useful cytokines. Eur J Immunol. Dec. 1997; 27(12):3420-6.
Lonsdorf et al., Intratumor CpG-oligodeoxynucleotide injection induces protective antitumor T cell immunity. J Immunol. Oct. 15, 2003; 171(8):3941-6.
Magnusson et al., Importance of CpG dinucleotides in activation of natural IFN-alpha-producing cells by a lupus-related oligodeoxynucleotide. Scand J Immunol. Dec. 2001; 54(6):543-50.
McCluskie et al., CpG DNA is a potent enhancer of systemic and mucosal immune responses against hepatitis B surface antigen with intranasal administration to mice. J Immunol. Nov. 1, 1998; 161 (9):4463-6.
McCluskie et al., CpG DNA as mucosal adjuvant. Vaccine, 18: 231-237, 2000.
McCluskie et al., Oral, intrarectal and intranasal immunizations using CpG and non-CpG oligodeoxynucleotides as adjuvants. Vaccine. Oct. 15, 2000; 19(4-5):413-22.
McCluskie et al., CpG DNA is an effective oral adjuvant to protein antigens in mice. Vaccine. Nov. 22, 2000; 19(7-8):950-7.
McCluskie et al., The potential of oligodeoxynucleotides as mucosal and parenteral adjuvants. Vaccine. Mar. 21, 2001; 19(17-19):2657-60.
McCluskie et al., The use of CpG DNA as a mucosal vaccine adjuvant. Curr Opin Investig Drugs. Jan. 2001; 2(1):35-9.
McCluskie et al., The role of CpG in DNA vaccines. Springer Semin Immunopathol. 2000; 22(12):125-32.
Miconnet et al., CpG are efficient adjuvants for specific CTL induction against tumor antigen-derived peptide. J Immunol. Feb. 1, 2002; 168(3):1212-8.
O'Hagan et al., Recent developments in adjuvants for vaccines against infectious diseases. Biomol Eng. Oct. 15, 2001; 18(3):69-85.
Payette et al., History of vaccines and positioning of current trends. Curr Drug Targets Infect Disord. Nov. 2001; 1(3):241-7.
Revaz et al., The importance of mucosal immunity in defense against epithelial cancers. Curr Opin Immunol. Apr. 2005; 17(2): 175-9.
Roman et al., Immunostimulatory DNA sequences function as T helper-1-promoting adjuvants. Nat Med. Aug. 1997; 3(8):849-54.
Sonehara et al., Hexamer palindromic oligonucleotides with 5'-CG-3' motif(s) induce production of interferon. J Interferon Cytokine Res. Oct. 1996; 16(10):799-803.
Threadgill et al., Mitogenic synthetic polynucleotides suppress the antibody response to a bacterial polysaccharide. Vaccine. Jan. 1998; 16(1):76-82.
Tortora et al., Oral antisense that targets protein kinase a cooperates with taxol and inhibits tumor growth, angiogenesis, and growth factor production. Clin Cancer Res. Jun. 2000; 6(6):2506-12.
Vicari et al., Reversal of tumor-induced dendritic cell paralysis by CpG immunostimulatory oligonucleotide and anti-interleukin 10 receptor antibody. J Exp Med. Aug. 19, 2002; 196(4):541-9.
Wagner et al., CpG motifs are efficient adjuvants for genetic vaccines to induce antigen-specific protective anti-tumor T cell responses. 2000; 203:429. Abstract R46.

Wang et al., Synergy between CpG-60 or non-CpG DNA and specific antigen for B cell activation. Int Immunol. Feb. 2003; 15(2):223-31.
Weeratna et al., CpG ODN can re-direct the Th bias of established Th2 immune responses in adult and young mice. FEMS Immunol Med Microbiol. Dec. 2001; 32(1):65-71.
Weiner et al., Immunostimulatory oligodeoxynucleotides containing the CpG motif are effective as immune adjuvants in tumor antigen immunization. Proc Natl Acad Sci USA. Sep. 30, 1997; 94(20): 10833-7.
Wernette et al., CpG oligodeoxynucleotides stimulate canine and feline immune cell proliferation. Vet Immunol Immunopathol. Jan. 15, 2002; 84(3-4):223-36.
Yamamoto et al., Lipofection of synthetic oligodeoxyribonucleotide having a palindromic sequence of AACGTT to murine splenocytes enhances interferon production and natural killer activity. Microbiol Immunol. 1994; 38(10):831-6.
Weigel et al., "CpG oligodeoxynucleotides potentiate the antitumor effects of chemotherapy or tumor resection in an orthotopic murine model of rhabdomyosarcoma," *Clin. Cancer Res.*, Aug. 2003, vol. 9, No. 8, pp. 3105-3114.
Agrawal (Ed.), *Methods in Molecular Biology.*, "Protocols for Oligonucleotides and Analogs, Synthesis and Properties," Table of Contents Only, Humana Press, Totowa, New Jersey.
Abuchowski et al., "Soluble Polymer-Enzyme Adducts," *Enzymes as Drugs*, Chapter 13, 1981, pp. 367-383, John Wiley & Sons.
Ackley et al., "Immunologic Abnormalities in Pathogen-Free Cats Experimentally Infected with Feline Immunodeficiency Virus," *Journal of Virology*, Nov. 1990, pp. 5652-5655, vol. 64, No. 11, American Society for Microbiology.
Adjei et al., "Pulmonary Delivery of Peptide Drugs: Effect of Particle Size on Bioavailability of Leuprolide Acetate in Healthy Male Volunteers," *Pharmaceutical Research*, Jun. 1990, pp. 565-569, vol. 7, No. 6, Plenum Press.
Sjödin et al., "Radioreceptor assay for formulations of salmon calcitonin," *International Journal of Pharmaceutics*, 1990, pp. 135-142, vol. 63, Elsevier Science Publishers B.V.
Ballas et al., "Induction of NK Activity in Murine and Human Cells by CpG Motifs in Oligodeoxynucleotides and Bacterial DNA," *The Journal of Immunology*, 1996, pp. 1840-1845.
Berman et al., "Protection of chimpanzees from infection by HIV-1 after vaccination with recombinant glycoprotein gp120 but not gp160," *Nature*, Jun. 14, 1990, pp. 622-625, vol. 345.
Braquet et al., "Effect of Endothelin-1 on Blood Pressure and Bronchopulmonary System of the Guinea Pig," *Journal of Cardiovascular Pharmacology*, 1989, pp. S143-S146, vol. 13, Suppl. 5, Raven Press.
Bülow et al., "Erhohte Pathogenitat des Erregers der aviaren infektiosen Anamie bei Huhnerkuken (CAA) bei simultaner Infektion mit Virus der Marekschen Krankheit (MDV), Bursitisvirus (IBDV) oder Reticuloendotheliosevirus (REV)," *J. Vet. Med. B*, 1986, pp. 93-116, vol. 33, Paul Parey Scientific Publishers.
Thomas (Ed.), *Medical Microbiology, 5th Edition*, 1983, Table of Contents Only, Bailliere Tindall, Great Britain.
Carlson et al., "Vaccine Protection of *Rhesus macaques* Against Simian Immunodeficiency Virus Infection," *AIDS Research and Human Retroviruses*, 1990, pp. 1239-1246, vol. 6, No. 11, Mary Ann Liebert, Inc.
Cohen et al., "CD4+ T-Cells from Mice Immunized to Syngeneic Sarcomas Recognize Distinct, Non-Shared Tumor Antigens," *Cancer Research*, Feb. 15, 1994, pp. 1055-1058, vol. 54.
Crooke et al., "Progress in Antisense Oligonucleotide Therapeutics," *Annu. Rev. Pharmacol. Toxicol.*, 1996, pp. 107-129, Annual Reviews Inc.
Debs et al., "Lung-Specific Delivery of Cytokines Induces Sustained Pulmonary and Systemic Immunomodulation in Rats," *The Journal of Immunology*, May 15, 1998, pp. 3482-3488, vol. 140, No. 10, The American Association of Immunologists, USA.
Desrosiers et al., "Vaccine protection against simian immunodeficiency virus infection," *Proc. Natl. Acad. Sci. USA*, Aug. 1989, pp. 6353-6357, vol. 86.
Durand et al., "Triple-Helix Formation by an Oligoneculeotide Containing One $(dA)_{12}$ and Two $(dT)_{12}$ Sequences Bridged by Two Hexaethylene Glycol Chains," *Biochemistry*, 1992, pp. 9197-9203, vol. 31, No. 38, American Chemical Society.
Eckstein (ed.), *Oligonucleotides and Analogues, A Practical Approach*, 1991, Table of Contents Only, Oxford University Press, New York.
Fontanel et al., "Sterical recognition by $T_4$ polynucleotide kinase of non-nucleosidic moieties 5'-attached to oligonucleotides," *Nucleic Acids Research*, 1994, pp. 2022-2027, vol. 22, No. 11, Oxford University Press.
Froehler et al., "Triple-Helix Formation by Oligodeoxynucleotides Containing the Carbocyclic Analogs of Thymidine and 5-Methyl-2'-deoxycytidine," *J. Am. Chem. Soc.*, 1992, pp. 8320-8322, vol. 114, American Chemical Society.
Goodchild, "Conjugates of Oligonucleotides and Modified Oligonucleotides: A Review of Their Synthesis and Properties," *Bioconjugate Chemistry*, May/Jun. 1990, pp. 165-187, vol. 1, No. 3, American Chemical Society.
Hubarrd et al., "Anti-Neutrophil-Elastase Defenses of the Lower Respiratory Tract in α1-Antitrypsin Deficiency Directly Augmented with an Aerosol of α1-Antitrypsin," *Annal of Internal Medicine*, Aug. 1, 1989, pp. 206-212, vol. 111, No. 3.
Radhakrishnan et al., "Modified oligonucleotides—synthesis, properties and applications," *Current Opinion in Moleculare Therapeutics*, Jun. 1999, pp. 344-358, vol. 1, No. 3.
Jiang et al., "Pseudo-Cyclic Oligonucleotides: In Vitro and In Vivo Properties," *Bioorganic & Medicinal Chemistry*, 1999, pp. 2727-2735, vol. 7, Elsevier Science Ltd.
Kaufmann (Ed.), *Novel Vaccination Strategies*, 2004, Table of Contents Only, Wiley-VCH Verlag GmbH & Co.
Krieg et al., "Sequence motifs in adenoviral DNA block immune activation by stimulatory CpG motifs," *Proc. Natl. Acad. Sci. USA*, Oct. 1988, pp. 12631-12636, vol. 95, The National Academy of Sciences.
Krieg et al., "CpG motifs in bacterial DNA trigger direct B-cell activation," *Nature*, Apr. 6, 1995, pp. 546-549, vol. 374.
Krieg, "Leukocyte Stimulation by Oligodeoxynucleotides," *Applied Antisense Oligonucleotide Technology*, 1998, Chapter 24, pp. 431-448, Wiley-Liss, Inc.
Krieg, "Mechanisms and application of immune stimulatory CpG oligodeoxynucleotides," *Biochimica et Biophysica Acta*, 1999, pp. 107-116, vol. 1489, Elsevier Science B.V.
Kriegler, *Gene Transfer and Expression*, 1990, Table of Contents Only, Stockton Press, New York.
Langer, "New Methods of Drug Delivery," *Science*, Sep. 28, 1990, pp. 1527-1533, vol. 249.
Matteucci et al., "The Synthesis of Oligodeoxypyrmidines on a Polymer Support," *Tetrahedron Letters*, 1980, pp. 719-722, vol. 21, Pergamon Press, Ltd. Great Britain.
Messina et al., "Stimulation of In Vitro Murine Lymphoscyte Proliferation by Bacterial DNA," *The Journal of Immunology*, Sep. 15, 1991, pp. 1759-1764, vol. 147, No. 6, The American Association of Immunologists, USA.
Murphey-Corb et al., "A Formalin-Inactivated Whole SIV Vaccine Confers Protection in Macaques," *Science*, Dec. 8, 1989, pp. 1293-1297, vol. 246.
Murray (Ed.), *Gene Transfer and Expression Protocols*, 1991, Table of Contents Only, The Humana Press Inc., Clifton, New Jersey.
Newmark et al., "Preparation and Properties of Adducts of Streptokinase and Streptokinase-Plasmin Complex with Polyethylene Glycol and Pluronic Polyol F38," *Journal of Applied Biochemistry*, 1982, pp. 185-189, vol. 4, Academic Press, Inc.
Nielsen et al., "Peptide Nucleic Acid (PNA). A DNA Mimic with a Peptide Backbone," *Bioconjugate Chem.*, 1994, pp. 3-7, vol. 5, American Chemical Society.
Olmsted et al., "Molecular cloning of feline immunodeficiency virus," *Proc. Natl. Acad. Sci. USA*, Apr. 1989, pp. 2448-2452, vol. 86.
Olmsted et al., "Nucleotide sequence analysis of feline immunodeficiency virus: Genome organization and relationship to other lentiviruses," *Proc. Natl. Acad. Sci. USA*, Oct. 1989, pp. 8088-8092, vol. 86.
Pedersen et al., "Isolation of a T-Lymphotropic Virus from Domestic Cats with an Immunodeficiency-Like Syndrome," *Science*, Feb. 13, 1987, pp. 790-793, vol. 235.

Iyer et al., "3*H*-1,2-Benzodithiole-3-one 1,1-Dioxide as an Improved Sulfurizing Reagent in the Solid-Phase Synthesis of Oligodeoxyribonucleoside Phosphorothioates," *J. Am. Chem. Soc.*, 1990, pp. 1253-1253, vol. 112, American Chemical Society.

Ortiagao et al., "Antisense Effect of Oligodeoxynucleotides with Inverted Terminal Internucleotidic Linkages: A Minimal Modification Protecting against Nucleolytic Degradation," *Antisense Research & Development*, 1992, pp. 129-146, vol. 2, Mary Ann Liebert, Inc.

Rankin et al., "An Essential Role of Th1 Responses and Interferon Gamma in Infection-Mediated Suppression of Neoplastic Growth," *Cancer Biology & Therapy*, Nov./Dec. 2003, pp. 687-693, vol. 2, No. 6, Landes Bioscience.

Ren et al., "Cytokine-Dependent Anti-Viral Role of CD4-Positive T Cells in Therapeuic Vaccination Against Chronic Hepatitis B Viral Infection," *Journal of Medical Virology*, 2003, pp. 376-384, vol. 71, Wiley-Liss, Inc.

Rosenberger et al., "The Isolation and Characterization of Chicken Anemia Agent (CAA) from Broilers in the United States," *Avian Diseases*, 1989, pp. 707-713, vol. 33.

Sambrook et al. (Eds.), *Molecular Cloning: A Laboratory Manual, Second Edition*, 1989, Table of Contents Only, Cold Spring Harbor Laboratory Press.

Seliger et al., "Oligonucleotide Analogues with Terminal 3'-3'- and 5'-5'- Internucleotidic Linkages as Antisense Inhibitors of Viral Gene Expression," *Nucleosides & Nucleotides*, 1991, pp. 469-477, vol. 10, No. 1-3, Marcel Dekker, Inc.

Sergueev et al., "*H*-Phosphonate Approach for Solid-Phase Synthesis of Oligodeoxyribonucleoside Boranophosphates and Their Characterization," *J. Am. Chem. Soc.*, 1998, pp. 9417-9427, vol. 120, American Chemical Society.

Smith et al., "Pulmonary Deposition and Clearance of Aerosolized Alpha-1-Proteinase Inhibitor Administered to Dogs and to Sheep," *J. Clin. Invest.*, Oct. 1989, pp. 1145-1154, vol. 84.

Stirchak et al., "Uncharged stereoregular nucleic acid analogs: 2. Morpholino nucleoside oligomers with carbamate internucleoside linkages," *Nucleic Acids Research*, 1989, pp. 6129-6141, vol. 17, No. 15.

Stott et al., "Preliminary report: protection of cynomolgus macaques against simian immunodeficiency virus by fixed infected-cell vaccine," *The Lancet*, Dec. 22/29, 1990, pp. 1538-1541, vol. 336.

Suri et al., "Non-cytolytic inhibition of hepatitis B virus replication in human hepatocytes," *Journal of Hepatology*, 2001, pp. 790-797, vol. 35, Elsevier Science B.V.

Tarkoy et al., "31. Nucleic-Acid Analogues with Constraint Conformational Flexibility in the Sugar-Phospate Backbone ('Bicyclo-DNA')," *Helvetica Chimica Acta*, 1993, pp. 481-510, vol. 76.

Tokunaga et al., "Antitumor Activity of Deoxyribonucleic Acid Fraction From *Mycobacterium bovis* BCG. I. Isolation, Physicochemical Characterization, and Antitumor Activity," *JNCI*, Apr. 1984, pp. 955-962, vol. 72, No. 4.

Tokunaga et al., "A Synthetic Single-Stranded DNA, Poly(dG,dC), Induces Interferon-$\alpha/\beta$ and -$\gamma$, Augments Natural Killer Activity, and Suppresses Tumor Growth," *Jpn. J. Cancer Res.*, Jun. 1988, pp. 682-686, vol. 79.

Uhlmann et al., "Chapter 16. Oligonucleotide Analogs Containing Dephospho-Internucleoside Linkages," *Methods in Molecular Biology*, vol. 20: *Protocols for Oliqonucleotides and Analogs*, 1993, pp. 355-389, Humana Press Inc.

Uhlmann et al., "Antisense Oligonucleotides: A New Therapeutic Principle," *Chemical Reviews*, Jun. 1990, pp. 544-584, vol. 90, No. 4.

Bulow, "Infectious Anemia," *Diseases of Poultry*, 9th Edition, 1991, pp. 690-699.

Vandendriessche et al., "Acyclic Oligonucleotides: Possibilities and Limitations," *Tetrahedron*, 1993, pp. 7223-7238, vol. 49, No. 33, Pergamon Press Ltd., Great Britain.

Verma et al., "Modified Oligonucleotides: Synthesis and Strategy for Users," *Annu. Rev. Biochem.*, 1998, pp. 99-134, vol. 67, Annual Reviews.

Wagner et al., "Potent and selective inhibition of gene expression by an antisense heptanucleotide," *Nature Biotechnology*, Jul. 1996, pp. 840-844, vol. 14.

Yamamoto et al., "Pathogenesis of experimentally induced feline immunodeficiency virus infection in cats," *Am. J. Vet. Res.*, Aug. 1988, pp. 1246-1258, vol. 49, No. 8.

Yamamoto et al., "Feline Immunodeficiency Syndrome—A Comparison between Feline T-Lymphotropic Lentivirus and Feline Leukemia Virus," *Leukemia*, Dec. 1988, pp. 204S-215S, vol. 2, No. 12 Supplement.

Yamamoto et al., "Unique Palindromic Sequences in Synthetic Oligonucleotides are Required to Induce INF and Augment INF-Mediated Natural Killer Activity," *The Journal of Immunology*, Jun. 15, 1992, pp. 4072-4076, vol. 148, No. 12.

Yuasa et al., "Isolation and Some Characteristics of an Agent Inducing Anemia in Chicks," *Avian Diseases*, Apr.-Jun. 1979, pp. 366-385, vol. 23, No. 2.

Yuasa et al., "Effect of Infectious Bursal Disease Virus Infection on Incidence of Anemia by Chick Anemia Agent," *Avian Diseases*, Jan.-Mar. 1980, pp. 202-209, vol. 24, No. 1.

Cebon et al., *Proc. Am. Soc. Clin. Oncol.*, vol. 21, 2002, p. 86 (abstract).

Supplemental European Search Report for European (EPO) Application No. 04 78 9341 mailed on Nov. 5, 2007, together with forms EPO Form 2901 and EPO PTO form 1507.4.

Busson, Marc et al., "Prediction of CD4+ T Cell Epitopes Restricted to HLA-DP4 Molecules", *Journal of Immunological Method*, Dec. 2006, vol. 317, No. 1-2, pp. 144-151- XP002428277.

Chen, Qiyuan et al., "Immunodominant CD4+ Responses Identified in a Patient Vaccinated with Full-Length NY-ESO-1 Formulated with ISCOMATRIX Adjuvant", *Proceedings of the National Academy of Sciences of the United States of America*, Jun. 22, 2004, vol. 101, No. 25, pp. 9363-9368, XP002428274.

Jackson, Heather et al., "Striking Immunodominance Hierarchy of Naturally Occurring CD8+ and CD4+ T Cell Responses of Tumor Antigen NY-ESO-1", *Journal of Immunology*, 2006, May 2006, vol. 176, No. 10, pp. 5908-5917-XP002428276.

Mandic, Maja et al., "One NY-ESO-1-Derived Epitope that Promiscuously Binds to Multiple HLA-DR and HLA-DP4 Molecules and Stimulates Autologous CD4+ T Cells from Patients with NY-ESO-1-Expressing Melanoma", *Journal of Immunology*, Feb. 2005, vol. 174, No. 3, pp. 1751-1759-XP002428278.

Valmori, Danla et la. "Epitope Clustering in Regions Undergoing Efficient Proteasomal Processing Defines Immunodominant CTL Regions of a Tumor Antigen", *Clinical Immunology*, vol. 122, No. 2, Feb. 2007, pp. 163-172, XP-002428275.

Brett et al., 1993, "Influence of the antigen delivery system on immunoglobulin isotype selection and cytokine production in response to influenza A nucleoprotein," *Immunology*, 80(2):306-12.

Britt et al., 1995, "Forumulation of an immunogenic human cytomegalovirus vaccine: responses in mice," *J. Infect. Dis.*, 171(1): 18-25.

Bomford et al., 1992, "The control of the antibody isotype response to recombinant human immunodeficiency virus gp120 antigen by adjuvants," *AIDS Res. Hum. Retroviruses*, (10): 1765-71.

Helling et al., 1995, "GM2-KLH conjugate vaccine: increased immunogenicity in melanoma patients after administration with immunological adjuvant QS-21," *Cancer Res.*, 55(13):2783-8.

Kandimalla et al., 2001, "Effect of chemical modifications of cytosine and guanine in a CpG-motif of oligonucleotides: structure-immunostimulatory activity relationships," *Bioorg. Med. Chem.*, 9(3):807-13.

Keler et al., 2000, "Differential effect of cytokine treatment on Fc alpha receptor I- and Fc gamma receptor I- mediated tumor cytotoxicity by monocyte-derived macropages," *J. Immunol.*, 64(11):5746-52.

Kensil et al., 1991, "Development of a genetically engineered vaccine against feline leukemia virus infection," *J. Am. Vet. Assoc.* 199(10): 1423-7.

Kensil et al., 1993, "Adjuvant activity of QS-21 isomers," *Ann. N.Y. Acad. Sci.*, 690:392-5.

Lewis et al., 2000, "Evaluation of CD8(+) T-cell frequencies by the Elispot assay in healthy individuals an in patients with metastatic melanoma immunized with tyrosinase peptide," *Int. J. Cancer*, 87(3):391-8.

Livinston et al., 1995, "Impact of Immunological Adkuvants and Administration Route on HAMA Response after Immunization with Murine Monoclonal Antibody MELIMMUNE-1 in Melanoma Patients," *Vaccine Research*, 4(2):87-94.

Marciani et al., 2000, "Development of semisynthetic Triterpenoid saponin derivatives with immune stimulating activity," *Vaccine*, 18(27): 3141-51.

Newman et al., 1994, "Induction of antigen-specific killer T Lymphocyte response using subunit SIVmac251 gag and env vaccines containing QS-21 saponin adjuvant," *AIDS Res. Hum. Retroviruses*, (7):853-61.

Woolridge et al., 1997, "Immunostimulatory Oligodeoxynucleotides Containing CpG Motifs Enhance the Efficacy of Monoclonal Antibody Thereapy of Lymphona," *Blood*, 89:2994-2998.

Office Action issued May 8, 2009 by the Examiner in U.S. Appl. No. 10/622,470 (US 2004/0191270).

Office Action issued Sep. 2, 2008 by the Examiner in U.S. Appl. No. 10/622,470 (US 2004/0191270).

Office Action issued Dec. 14, 2007 by the Examiner in U.S. Appl. No. 10/622,470 (US 2004/0191270).

Office Action issued Jun. 6, 2007 by the Examiner in U.S. Appl. No. 10/622,470 (US 2004/0191270).

Office Action issued Sep. 29, 2006 by the Examiner in U.S. Appl. No. 10/622,470 (US 2004/0191270).

Office Action issued Jan. 17, 2006 by the Examiner in U.S. Appl. No. 10/622,470 (US 2004/0191270).

Office Action issued Sep. 8, 2005 by the Examiner in U.S. Appl. No. 10/622,470 (US 2004/0191270).

Office Action issued Mar. 24, 2005 by the Examiner in U.S. Appl. No. 10/622,470 (US 2004/0191270).

Office Action issued Sep. 16, 2008 by the Examiner in U.S. Appl. No. 11/183,187 (US 2006/0287263).

Advisory Action issued Oct. 15, 2007 by the Examiner in U.S. Appl. No. 11/183,187 (US 2006/0287263).

Office Action issued Jul. 25, 2007 by the Examiner in U.S. Appl. No. 11/183,187 (US 2006/0287263).

Office Action issued Mar. 7, 2007 by the Examiner in U.S. Appl. No. 11/183,187 (US 2006/0287263).

Office Action issued Aug. 25, 2006 by the Examiner in U.S. Appl. No. 11/183,187 (US 2006/0287263).

Office Action issued Feb. 23, 2009 by the Examiner in U.S. Appl. No. 10/573,753 (US 2007/0190072).

Office Action issued Apr. 22, 2009 by the Examiner in U.S. Appl. No. 10/499,890 (US 2006/0210555).

Office Action issued Dec. 31, 2008 by the Examiner in U.S. Appl. No. 10/499,890 (US 2006/0210555).

Office Action issued May 12, 2008 by the Examiner in U.S. Appl. No. 10/499,890 (US 2006/0210555).

Rigby et al., *Vaccine*, vol. 14, No. 12, pp. 1095-1102, 1996.

Database entry : BIOSIS PREV199799800835: A. Ahlumwaliea et al., Modification of delivery system enhances MHC nonrestricted immunogenicity of V3 loop region of HIV-1 gp 120: *Microbiology & Immunology*, 1997, vol. 41, No. 10 (Abstract).

Lipford et al., *Vaccine*, 1994, vol. 12, No. 1, pp. 73-80.

Kersten et al., *Biochimica et Biophyica Acta*, 1062(1991), pp. 165-171.

Gupta et al., *Advanced Drug Delivery Reviews*, vol. 32, pp. 155-172 (1998).

Kuo et al., *Journal of Biochemistry*, 1995; 117(2): 438-442.

Mateu et al., *Journal of General Virology*, 1990; 71(Pt 3); 629-637.

Barr et al., *Immunology and Cell Biology*, (1996), pp. 8-25.

Rimmelzwaan et al., "A Novel Generation of Viral Vaccines Based on the ISCOM Matrix," (1995), pp. 543-558.

Nakanishi et al., *Biochemical and Biophysical Research Communications*; 1997, 240:793-797.

Cox et al., *Vaccine*, 1997, 15(3), pp. 428-456.

Callhan et al., *Pharmaceutical Research*, 1991; 8(7), pp. 851-858.

Offringa et al., *Gann Monogrpahs on Cancer Research*, vol. 48, pp. 73-81, 1999 (Abstract only).

Seeber et al., *Vaccine*, vol. 9, pp. 201-203, 1991.

Al-Shakhshir et al., *Vaccine*, vol. 12(5), pp. 472-474, 1994.

Bradford, *Anal. Biochem.*, 36:248-254 (1976).

Cox et al., *Animal Parasite Control Utilizing Biotechnology*, Ch. 4, Editor : Yong, W.K. CRC Press, 1992.

Cox et al., *BioDrugs*, 12:6, pp. 439-453, 1999.

Edwards et al., *Recent Research Devel. in Biotech. and Bioeng.*, pp. 343-356, 1998.

Elliott et al., *Vaccine*, vol. 17, pp. 2009-1019, 1999.

Friede et al., *Molecular Immun.*, vol. 30, No. 6, pp. 539-547, 1993.

Morein et al., << Immunostimulating complex (ISCOM) in Vaccines: Recent Trends and Progress, pp. 153-161, 1989.

Talsma et al., *BioPharm*, pp. 36-47, 1992.

Valerio et al. "Multiple peptide synthesis on acid-sabile handle derivatized polyethylene supports,", *Int. J. Peptide Protein Research*, pp. 158-165, 1994.

Office Action issued on Jan. 27, 2009, by the Examiner in U.S. Appl. No. 09/506,011.

Office Action issued on Feb. 22, 2008, by the Examiner in U.S. Appl. No. 09/506,011.

Office Action issued on Oct. 18, 2006, by the Examiner in U.S. Appl. No. 09/506,011.

Office Action issued on Mar. 28, 2006, by the Examiner in U.S. Appl. No. 09/506,011.

Office Action issued on May 25, 2005, by the Examiner in U.S. Appl. No. 09/506,011.

Office Action issued on Nov. 17, 2003, by the Examiner in U.S. Appl. No. 09/506,011.

Office Action issued on Feb. 25, 2003, by the Examiner in U.S. Appl. No. 09/506,011.

Office Action issued on Feb. 13, 2002, by the Examiner in U.S. Appl. No. 09/506,011.

Office Action issued on May 23, 2001, by the Examiner in U.S. Appl. No. 09/506,011.

Office Action issued on Jun. 18, 2009, by the Examiner in U.S. Appl. No. 11/183,187 (US 2006/0287263).

Office Action issued on Jun. 3, 2009, by the Examiner in U.S. Appl. No. 10/573,753 (US 2007/0190072).

Oumouna et al., *Developmental and Comparative Immunology*, 26(3):257-269, 2002.

Ho et al., *J. Immunol.*, 171:4920-4926, 2003.

Maraskovsky et al., *Clin. Canc. Res.*, 10:2879-2890, 2004.

Cebon et al., *Proc. Amer. Soc. Clin. Oncol.*, 21:6-2002, ASCO Presentation Slides, 18 pgs.

Van Der Most et al., *J. Immunol.*, 1996, 157:5543-5554.

Karin et al., *J. Exp. Med.*, 180: 2227-2237, 1994.

Chang et al., *J. Immunol.*, 1999, 162:1156-1164.

Van Der Most et al., *Virology*, 1998, 240:158-167.

Bergman et al., *J. Virol.*, 1994, 68(8):5306-5310.

Celis et al., *Molecular Immunol.*, 3 :1423-1430, 1994.

Ochoa-Garay et al., *Molecular Immunol.*, 34:273-281, 1994.

Notice of Allowance issued on Oct. 26, 2009 by the Examiner in U.S. Appl. No. 09/506,011 (US 7,776,343).

Office Action issued on Oct. 29, 2010 by the Examiner in U.S. Appl. No. 11/183,187 (US 2006/0287263).

Office Action issued on May 24, 2010 by the Examiner in U.S. Appl. No. 11/183,187 (US 2006/0287263).

Office Action issued on Nov. 30, 2009 by the Examiner in U.S. Appl. No. 11/183,187 (US 2006/0287263).

Office Action issued on Oct. 5, 2009 by the Examiner in U.S. Appl. No. 11/183,187 (US 2006/0287263).

Office Action issued on Jul. 20, 2010 by the Examiner in U.S. Appl. No. 10/499,890 (US 2006/0210555).

Office Action issued on Dec. 16, 2009 by the Examiner in U.S. Appl. No. 10/499,890 (US 2006/0210555).

Office Action issued on May 12, 2011 by the Examiner in U.S. Appl. No. 12/612,992 (US 2010/0047271).

Office Action issued on Nov. 8, 2010 by the Examiner in U.S. Appl. No. 12/612,992 (US 2010/0047271).

Berzofsky et al., "Progress on new vaccine strategies for the immunotherapy and prevention of cancer," The Journal of Clinical Investigation, vol. 113, No. 11, pp. 1515-1525, Jun. 2004.

"Four Hepatitis C Prevention Tips," Hepatitismagazine.com, Jun. 12, 2010, http:www.hepatitismagazine.com/2010/06/four-hepatitis-c-prevention-tips.

* cited by examiner

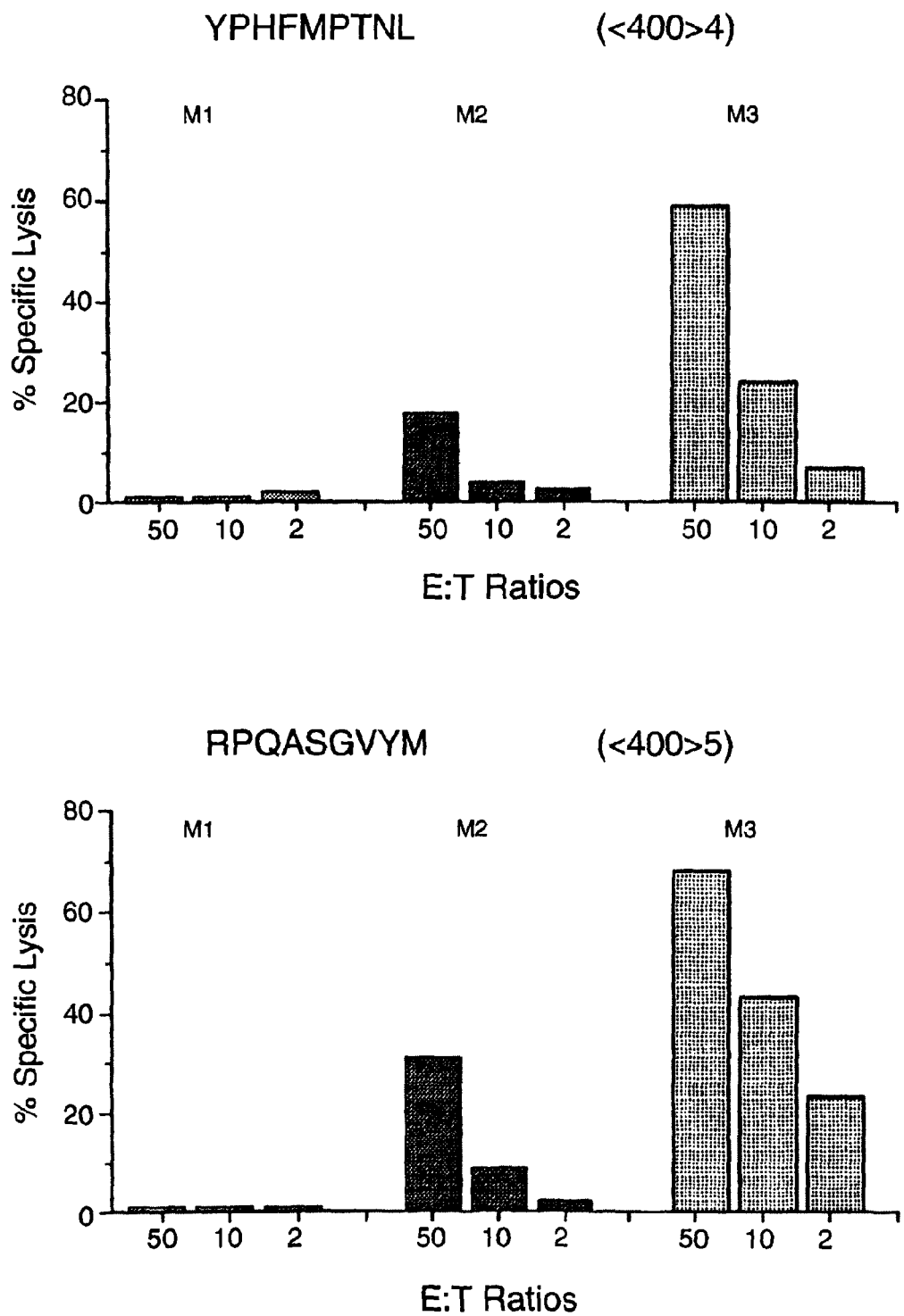
Figure 12a (ii)

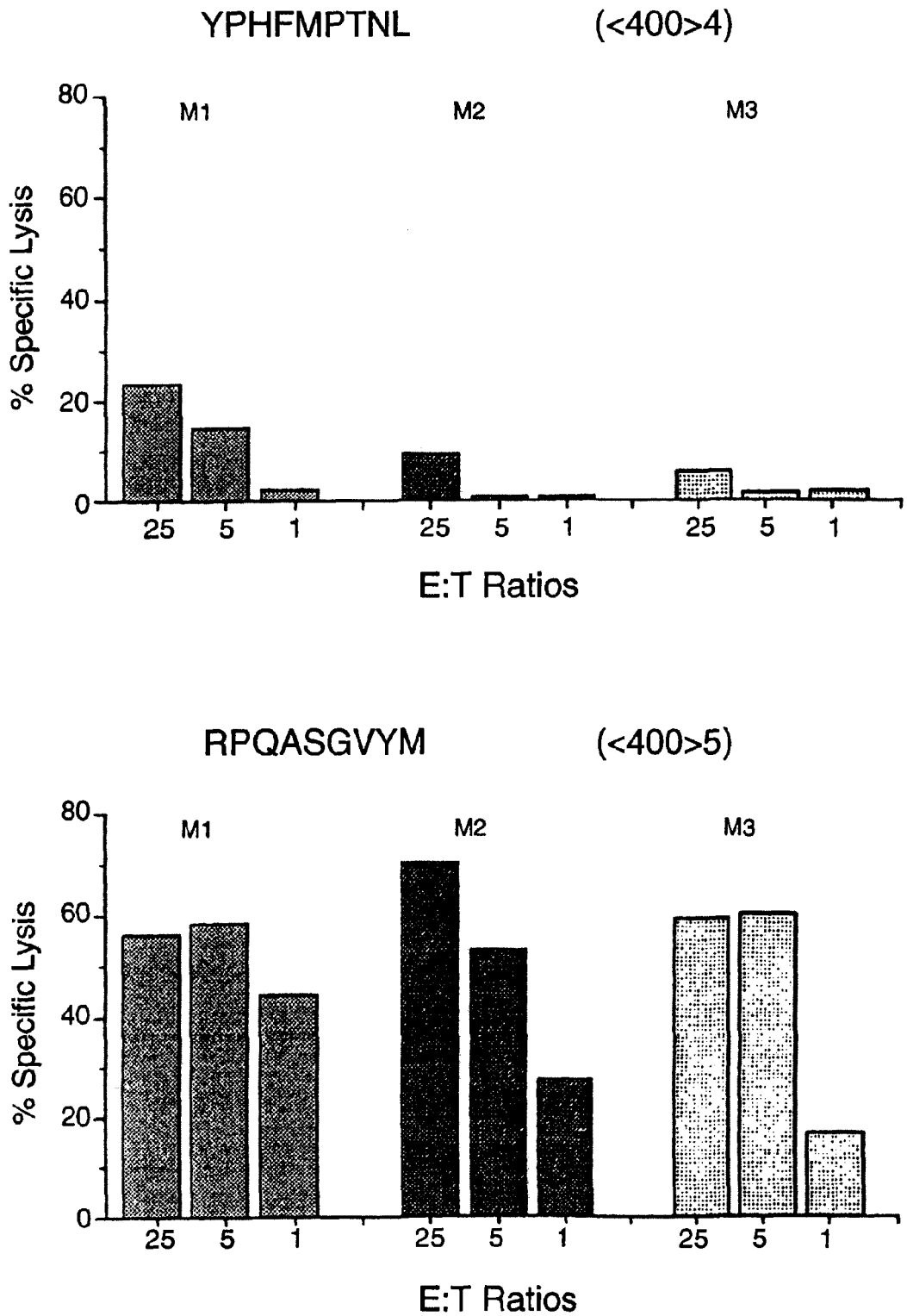
Figure 12b (ii)

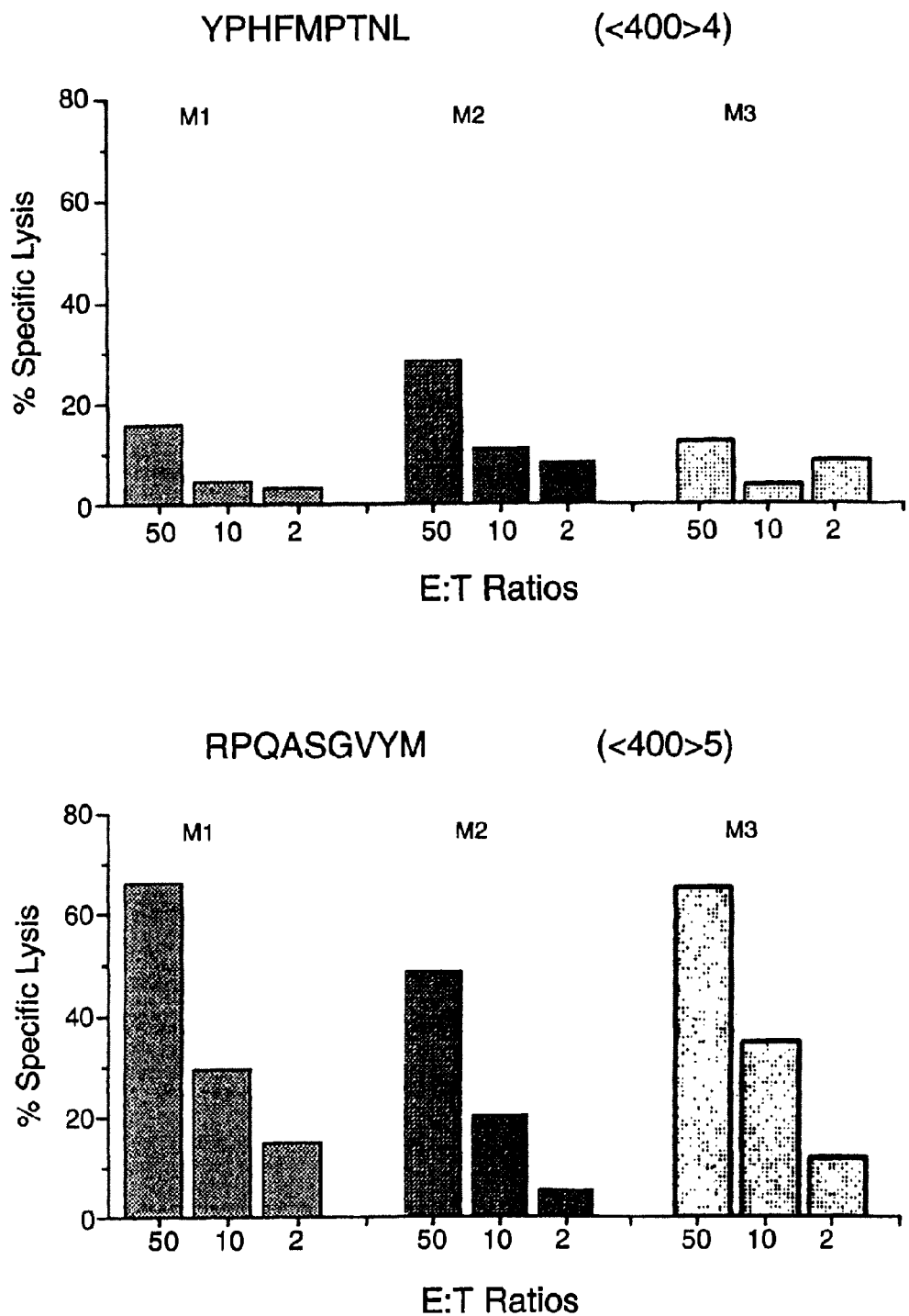
Figure 12c (ii)

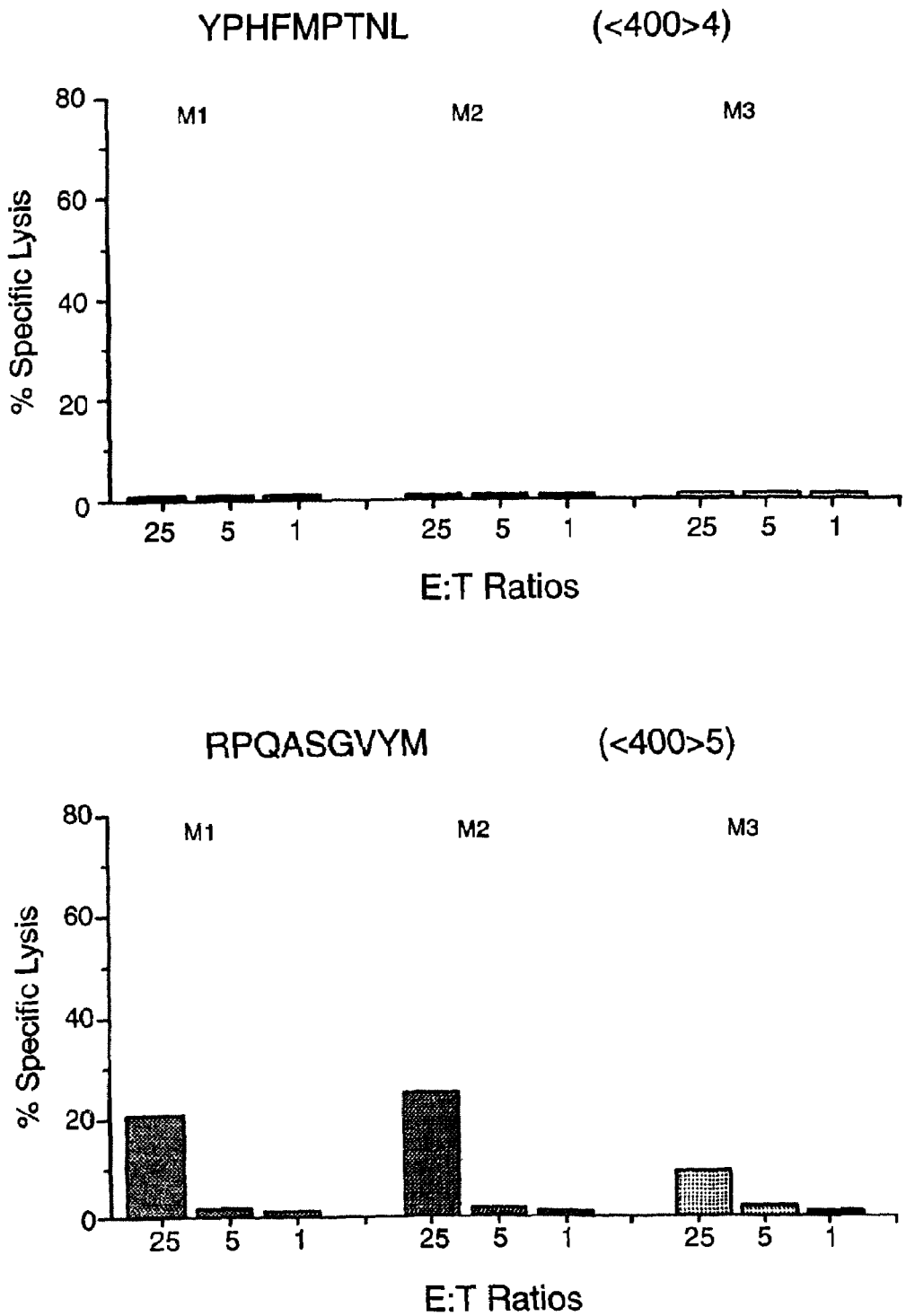
Figure 12d (ii)

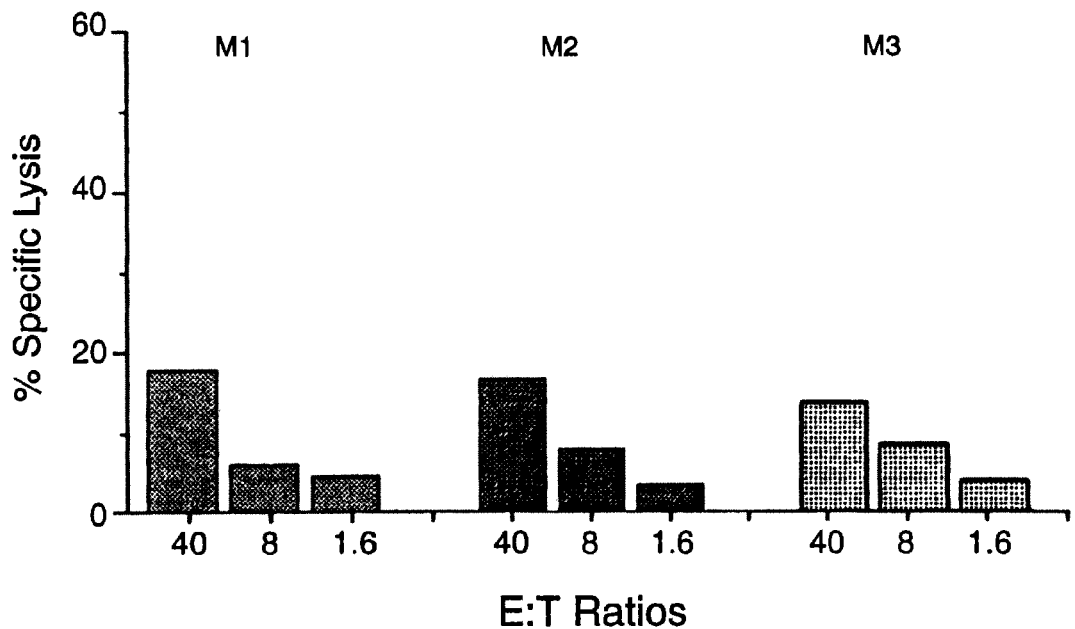
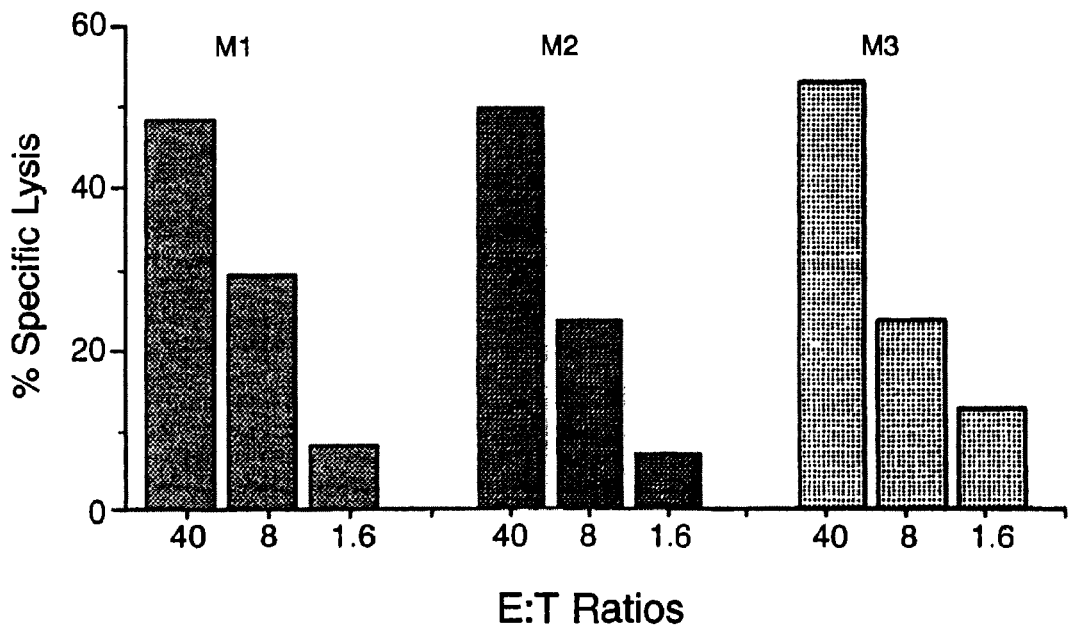
Figure 14a (ii)

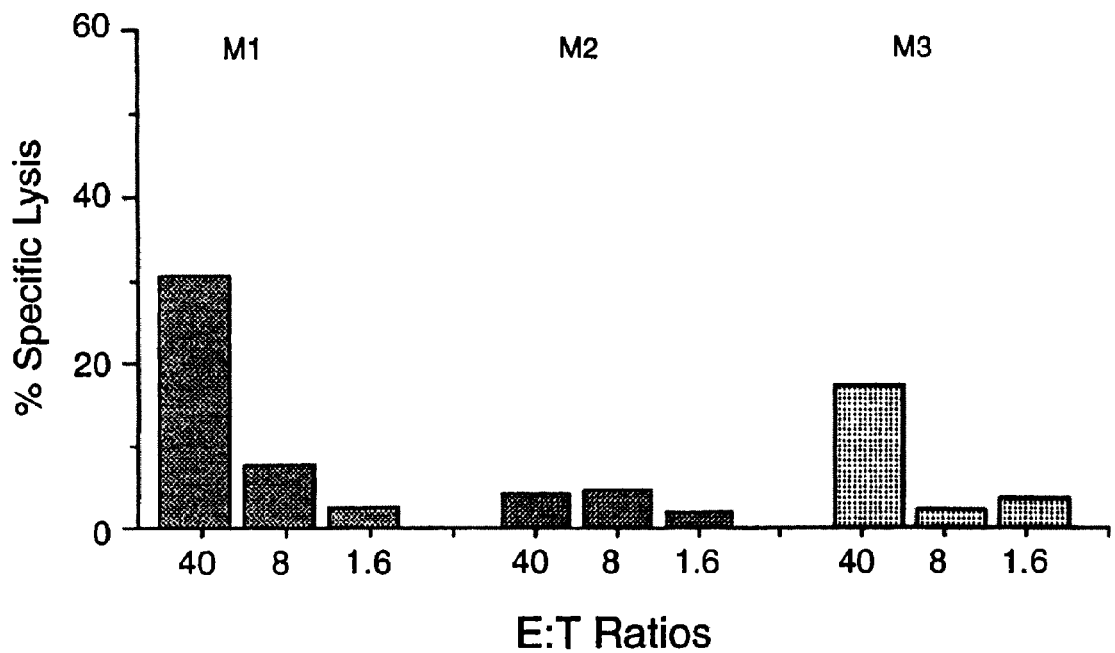
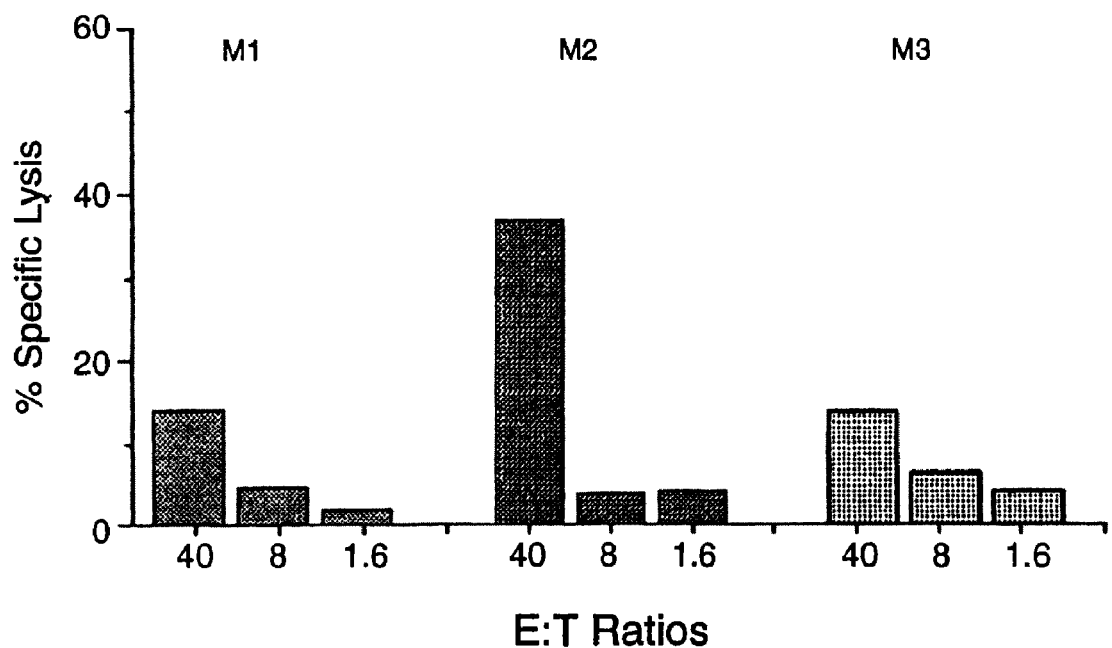
Figure 14b (ii)

under usual circumstances the immunogenic complex or vaccine composition is a therapeutic or prophylactic treatment.

IMMUNOGENIC COMPLEXES AND METHODS RELATING THERETO

This application is a continuation of U.S. application Ser. No. 09/506,011, filed on Feb. 17, 2000, which claims priority to Austalian application number PQ1861/99, filed Jul. 27, 1999, and Australian application number PP8735/99, filed Feb. 17, 1999, all of which are hereby incorporated by reference in their entirety.

FIELD OF THE INVENTION

The present invention relates generally to an immunogenic complex comprising a charged organic carrier and a charged antigen and, more particularly, a negatively charged organic carrier and a positively charged antigen. The complexes of the present invention are useful, inter alia, as therapeutic and/or prophylactic agents for facilitating the induction of a cytotoxic T-lymphocyte response to an antigen.

BACKGROUND OF THE INVENTION

Bibliographic details of the publications referred to by author in this specification are collected at the end of the description.

There is an increasing belief that co-delivery of antigen and adjuvant to the same antigen-presenting-cell (APC) is preferable and sometimes essential for induction of appropriate immune responses. For example, the ability of saponin-based adjuvants to induce $CD_8^+CTL$ responses is attributed to their ability to cause endosomal escape of antigen, a mechanism which requires co-delivery. Particle formation which comprises a stable complex of adjuvant and antigen is the simplest way to achieve co-delivery. The usefulness of ISCOM™ technology derives partly from the immunomodulatory activity of saponins and partly from their ability to form complexes with hydrophobic or amphipathic immunogens. However, many molecules lack hydrophobic regions and in fact such molecules are preferred as recombinant proteins because of their easier expression and purification.

Accordingly, there is a need to develop immunogenic complexes which facilitate the co-delivery of antigens and carriers which otherwise do not usually form sufficiently stable complexes. For example, complexes comprising antigens which lack hydrophobic regions together with adjuvant.

In work leading up to the present invention, the inventors have developed an immunogenic complex based on the electrostatic association of an antigen and an organic carrier, such as an adjuvant. This electrostatic association permits co-delivery of the antigen and the organic carrier to the immune system. Accordingly, by establishing an electrostatic association, antigens of interest (irrespective of their hydrophobicity) can be co-delivered with an organic carrier, for the purpose, for example, of inducing a cytotoxic T-lymphocyte response to the antigen.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The subject specification contains amino acid sequence information prepared using the programme PatentIn Version 2.0, presented herein after the bibliography. Each amino acid sequence is identified in the sequence listing by the numeric indicator <210> followed by the sequence identifier (e.g. <210>1, <210>2, etc.). The length, type of sequence (protein (PRT), etc) and source organism for each amino acid sequence are indicated by information provided in the numeric indicator fields <211>, <212> and <213>, respectively. Amino acid sequences referred to in the specification are defined by the information provided in numeric indicator field <400> followed by the sequence identifier (e.g. <400>1, <400>2, etc).

One aspect of the present invention relates to an immunogenic complex comprising a charged organic carrier and a charged antigen which organic carrier and antigen are electrostatically associated.

Another aspect of the present invention more particularly provides an immunogenic complex comprising a negatively charged organic carrier and a positively charged antigen which organic carrier and antigen are electrostatically associated.

Still another aspect of the present invention provides an immunogenic complex comprising a negatively charged organic carrier and a positively charged protein which organic carrier and protein are electrostatically associated.

Yet another aspect of the present invention provides an immunogenic complex comprising a negatively charged adjuvant and a positively charged protein which adjuvant and protein are electrostatically associated.

Yet still another aspect of the present invention provides an immunogenic complex comprising a negatively charged adjuvant and a positively charged protein, wherein said negatively charged adjuvant is a naturally negatively charged adjuvant which has been modified to increase the degree of its negative charge, which adjuvant and protein are electrostatically associated.

Still another aspect of the present invention provides an immunogenic complex comprising a negatively charged adjuvant and a positively charged protein, wherein said positively charged protein is a naturally positively charged protein which has been modified to increase the degree of its positive charge, which adjuvant and protein are electrostatically associated.

Still yet another aspect of the present invention provides an immunogenic complex comprising a negatively charged adjuvant and a positively charged protein, wherein said negatively charged adjuvant is a naturally negatively charged adjuvant which has been modified to increase the degree of its negative charge and said positively charged protein is a naturally positively charged protein which has been modified to increase the degree of its positive charge, which adjuvant and protein are electrostatically associated.

A further aspect of the present invention relates to a vaccine composition comprising as the active component an immunogenic complex comprising a charged organic carrier and a charged antigen which organic carrier and antigen are electrostatically associated together with one or more pharmaceutically acceptable carriers and/or diluent.

Another further aspect of the present invention relates to a method of eliciting, inducing or otherwise facilitating, in a mammal, an immune response to an antigen said method comprising administering to said mammal an effective amount of an immunogenic complex or a vaccine composition as hereinbefore described.

Yet another further aspect of the present invention relates to a method of treating a disease condition in a mammal said method comprising administering to said mammal an effective amount of an immunogenic complex or a vaccine composition as hereinbefore described wherein administering said composition elicits, induces or otherwise facilitates an immune response which inhibits, halts, delays or prevents the onset or progression of the disease condition.

Still another further aspect the present invention relates to the use an immunogenic complex or vaccine composition as hereinbefore defined in the manufacture of a medicament for inhibiting, halting, delaying or preventing the onset or progression of a disease condition.

Still yet another further aspect of the present invention relates to an agent for use in inhibiting, halting, delaying or preventing the onset or progression of a disease condition. Said agent comprising an immunogenic complex or vaccine composition as hereinbefore defined.

Single and three letter abbreviations used throughout the specification are defined in Table 1.

TABLE 1

Single and three letter amino acid abbreviations

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

BRIEF DESCRIPTION OF THE DRAWINGS

FIG. 4 is a graphical representation of antibody responses to ESO formulations. It can be seen that ESO associated ISCOMATRIX™ includes higher antibody responses than ESO alone especially in the Th1 subtype IgG2a.

DETAILED DESCRIPTION OF THE PREFERRED EMBODIMENTS

Figure 1A:
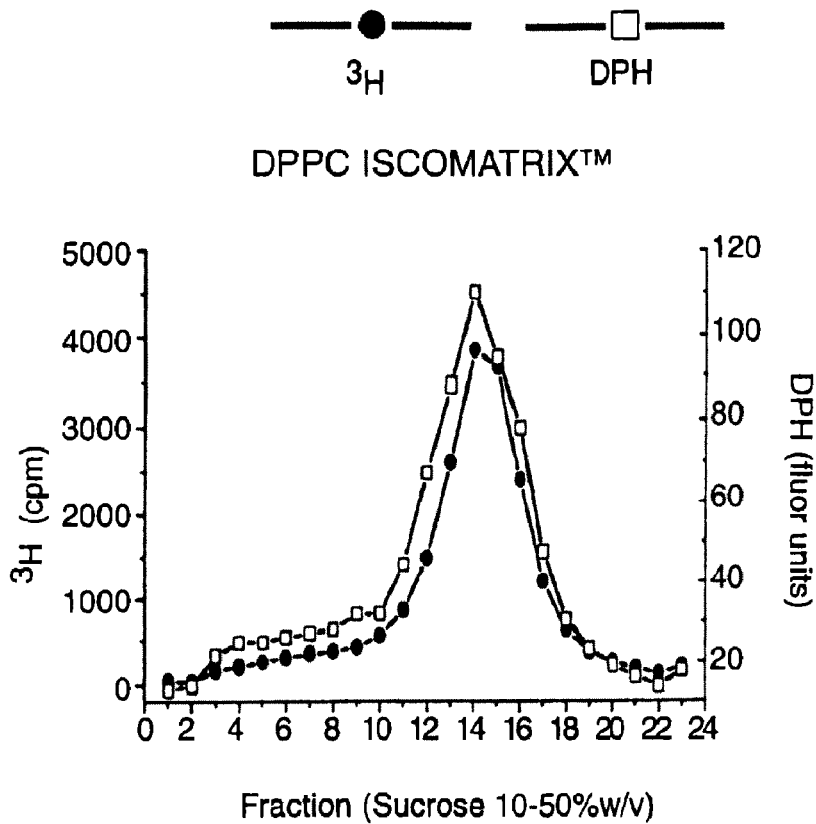
FIG. 1 is a graphical representation of the sucrose gradient analysis of ISCOMATRIX™ formulated with DPPC (FIG. 1A), CDL (FIG. 1B), DPL (FIG. 1C), MPL (FIG. 1D), DPA (FIG. 1E) and DPPG (FIG. 1F). In each case it can be seen that lipid and $^3$H overlap indicating incorporation of each lipid into the ISCOMATRIX™ structure.
Figure 1B:
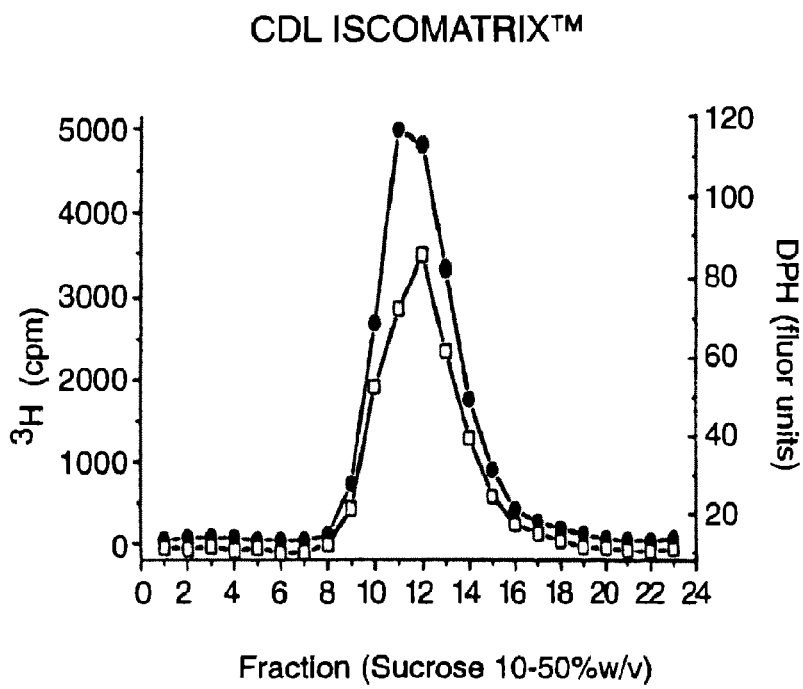
Figure 1C:
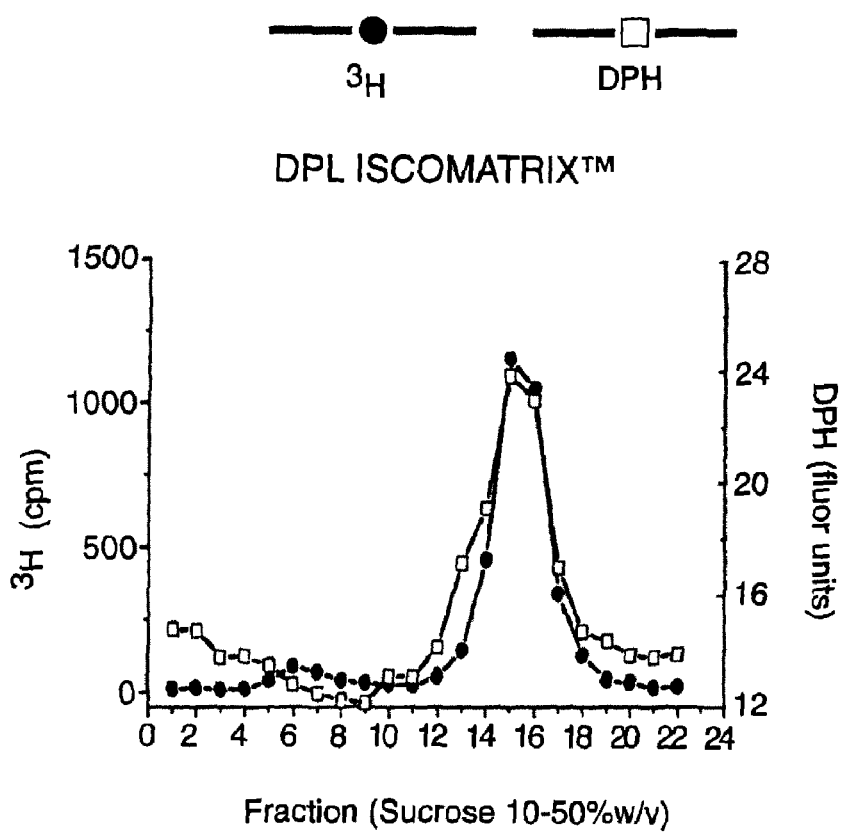
Figure 1D:
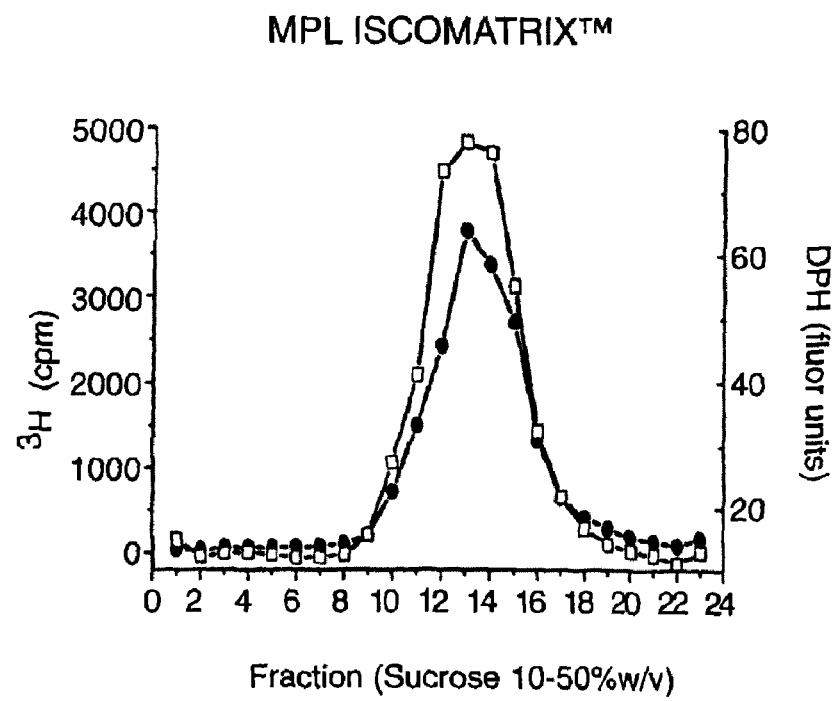
Figure 1E:
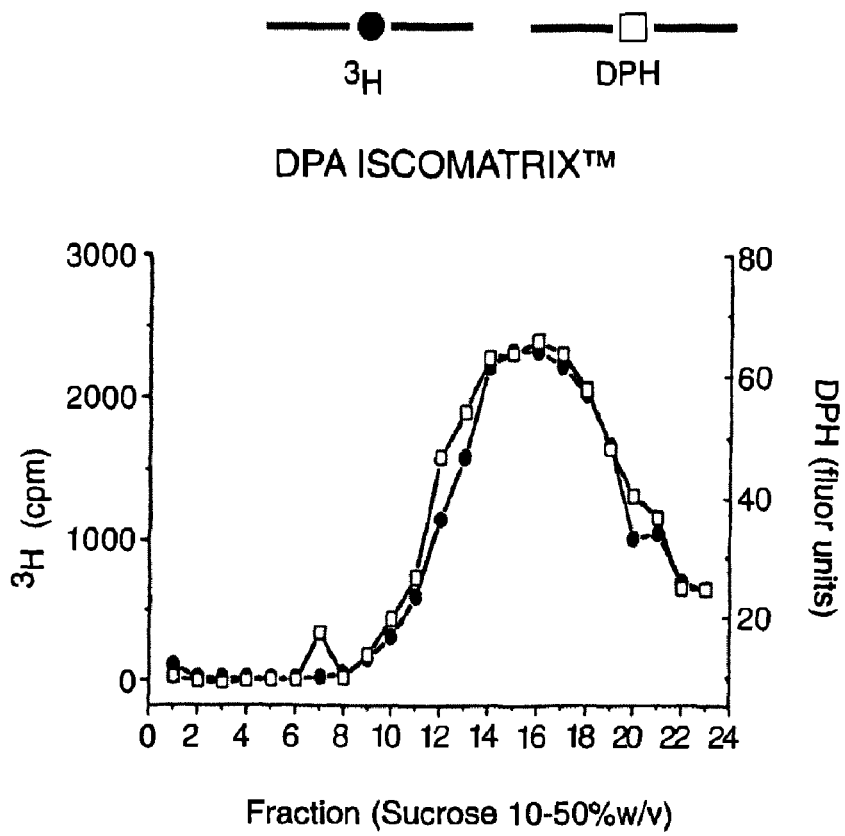
Figure 1F:
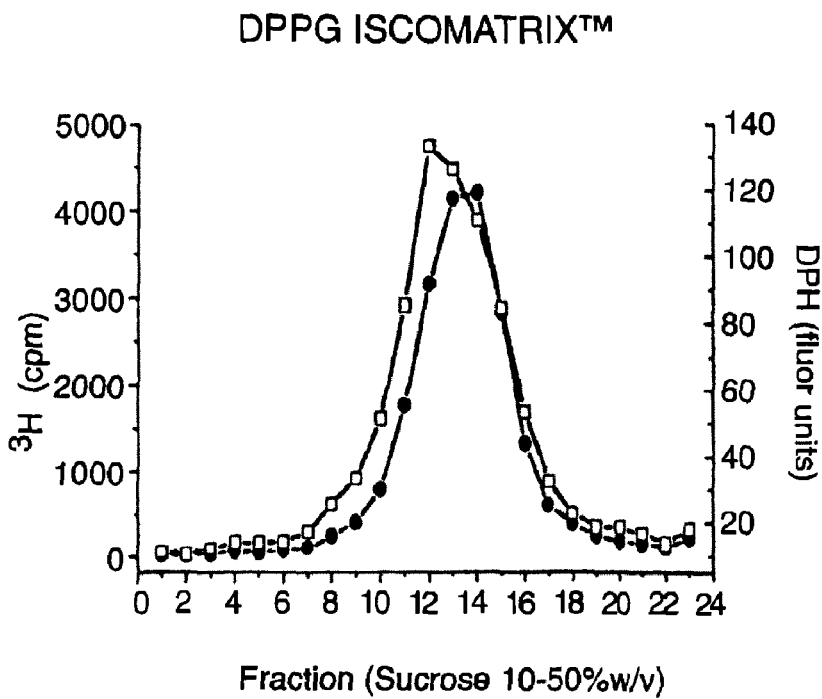

The present invention is predicated, in part, on the development of an immunogenic complex formulation which utilises electrostatic interactions to associate an antigen and a carrier thereby facilitating, inter alia, the co-delivery of these molecules to the immune system. The immunogenic complexes of the present invention are particularly suitable for use in facilitating the stimulation of cytotoxic T-lymphocyte responses to immunogens which do not comprise hydrophobic regions.

Accordingly, one aspect of the present invention relates to an immunogenic complex comprising a charged organic carrier and a charged antigen which organic carrier and antigen are electrostatically associated.

Reference to a "complex" should be understood as describing an entity of two or more different interacting chemical components.

Reference to a "charged" organic carrier of antigen should be understood as a reference to an organic carrier or antigen which exhibits an overall positive electrical charge or an overall negative electrical charge. By "overall" is meant the summation of the individual positive and negative charges which a given molecule comprises. Where the summation of the individual positive and negative charges results in overall electrical neutrality, the molecule is not regarded as "charged" within the context of the present invention. Preferably, the antigen comprises an overall positive charge and the organic carrier comprises an overall negative charge.

Accordingly, the present invention more particularly provides an immunogenic complex comprising a negatively charged organic carrier and a positively charged antigen which organic carrier and antigen are electrostatically associated.

Reference to "electrostatically associated" is a reference to the organic carrier and the antigen being linked, bound or otherwise associated by means which include electrostatic interaction. Accordingly, it should be understood that in some instances the electrostatic interaction will be the only attractive force which results in complexing of the antigen and the organic carrier. However, in other instances the formation of the electrostatic interaction may also lead to, or be associated with, the formation of other interactive forces.

Reference to "antigen" should be understood as a reference to any molecule against which it is sought to induce an immune response, and in particular, a cytotoxic T-lymphocyte response. The antigen may be either a proteinaceous or a non-proteinaceous molecule, which molecule may or may not be immunogenic if it were administered in isolation. The antigen of the present invention may be naturally derived or it may be recombinantly or synthetically produced. Following its isolation or synthesis the antigen may require further modification (for example, structural or sequence modification to improve its antigenicity) prior to use in the present invention. Antigens suitable for use in the present invention include, but are not limited to core proteins or nucleoproteins isolated from viruses, non-core viral proteins such as virus-like particles (VLPs), antigens of malignant and non-malignant cells, bacterial antigens, parasite antigens and synthetic and recombinant polytopes.

Preferably, the antigen is a protein. The term "protein" should be understood to encompass reference to proteins, polypeptides and peptides and derivatives and equivalents thereof. The protein may be glycosylated or unglycosylated, phosphorylated or dephosphorylated to various degrees and/or may contain a range of other molecules fused, linked, bound or otherwise associated to the protein such as amino acids, lipids, carbohydrates or other peptides, polypeptides or proteins. Reference hereinafter to a "protein" includes a protein comprising a sequence of amino acids as well as a protein associated with other molecules such as amino acids, lipids, carbohydrates or other peptides, polypeptides or proteins.

As hereinbefore defined, the antigen of the present invention may also be a polytope. The subject polytope may be produced by synthetic or recombinant means (for example refer International Patent Publication No. WO 96/03144).

According to this preferred embodiment, there is provided an immunogenic complex comprising a negatively charged organic carrier and a positively charged protein which organic carrier and protein are electrostatically associated.

In this regard, the antigen which is included in the immunogenic complex of the present invention may be, in its initial or natural form, positively charged, negatively charged or of neutral charge. Where an antigen is positively charged, it may nevertheless be weakly positively charged and may therefore require modification to increase its degree of positive charge such that complex formation with the negatively charged organic carrier is better facilitated. For example, wherein an antigen is weakly positively charged, increasing the degree of its positive charge may be achieved by any one of a number of methods known to those skilled in the art including, but not limited to, chemically adding further positive charge to the antigen or recombinant adding positive charge such as by adding polylysine to the antigen. This is of particular use where the antigen is a protein. Other methods which may be utilised to increase the degree of an antigen's positive charge include, but are not limited to, pH modification, chemical modifications or neutralisation of an antigen's negative charges with positively charged molecules such as arginine. Similarly, where an antigen is neutral or negatively charged, its overall charge can be converted to an overall positive charge by utilising such methodology. Conversion of a negatively charged antigen to express an overall positive charge may be of particular importance where the antigen is a protein, since most proteins are naturally negatively charged.

Once the charge of the antigen of interest is sufficiently positive, it becomes necessary to ensure that precipitation of the positively charged antigen does not occur prior to complex formation with the organic carrier. In this regard, any suitable method for preventing antigen precipitation may be utilised. For example, antigen solubility may be maintained by disrupting the forces that cause antigen aggregation. Disruption of these forces can be achieved, for example, by incorporating into the antigen solution chaotrophic agents such as urea and guanidine, solvents such as DMSO (dimethyl sulfoxide) and acetonitrile, intermediates such as zwitterions, detergents such as Triton X-100 and CHAPS (3-[(3-cholamidopropyl)-dimethylammonio]-2-hydroxy-1-propanesulfonate), reducing agents such as DTT (dithiothreitol) and cysteine and chelating agents such as EDTA (ethylene diaminetetraacetic acid). Solubility can also be maintained by altering the pH of the antigen solution or by chemical modification of the antigen to introduce polar or ionic molecules such as by alkylation or acetylation. A gradual or phased removal of these solubilising agents when the antigen has been brought into contact with the "organic carrier" or mild denaturation of the antigen can lead to a controlled precipitation of antigen with concomitant increased association with the organic carrier.

Reference to "organic carrier" should be understood as a reference to any molecule, aggregate or complex of molecules, compound or other entity which, when an antigen is associated with it, facilitates the induction of an immune response, and in particular a cytotoxic T-lymphocyte response, to the antigen. The subject carrier is "organic" and, in this regard, "organic" should be understood as a compound of carbon whether naturally, recombinantly or synthetically obtained or derived. In a particularly preferred embodiment the organic carrier is an adjuvant. By "adjuvant" is meant any organic molecule, aggregate or complex of organic molecules, compound or other entity which functions to stimulate, enhance or otherwise up-regulate any one or more aspects of the immune response. For example, the adjuvant may induce inflammation thereby attracting immune response cells to die site of antigen localisation. Alternatively, the adjuvant may slowly release the antigen thereby providing on-going stimulation of the immune system. Examples of adjuvants suitable for use in the present invention include, but are not limited to, saponin, saponin complexes, any one or more components of the immunostimulating complex of saponin, cholesterol and lipid known as ISCOMATRIX™ (for example the saponin component and/or the phospholipid component), liposomes or oil-in-water emulsions. [The composition and preparation of ISCOMATRIX™ is described in detail in International Patent Application Number PCT/SE86/00480, Australian Patent Numbers 558258 and 632067 and European Patent Publication No. 0 180 564, the disclosures of which are incorporated herein by reference]. Further examples of adjuvants include, but are not limited to, those detailed in the publication of Cox and Coulter, 1992, 1997 and 1999. It should be understood that the subject organic carrier may be naturally occurring or it may be synthetically or recombinantly derived.

Accordingly, the present invention still more preferably provides an immunogenic complex comprising a negatively charged adjuvant and a positively charged protein which adjuvant and protein are electrostatically associated.

Preferably, said adjuvant comprises saponin or a saponin complex. More preferably, said saponin complex is ISCOMATRIX™.

The organic carrier of the present invention may also be, in its initial or natural form, negatively charged, positively charged or neutral. Increasing the degree of negative charge (for example, where the organic carrier is only weakly negatively charged) or converting a neutral or positively charged organic carrier to a negatively charged organic carrier may also be achieved by any suitable method known to those skilled in the art. For example, where the organic carrier is an oil-in-water emulsion, incorporation of any anionic surfactant with a non-polar tail will impart an overall negative charge to the emulsion due to insertion of the tail of the surfactant into the oil droplet which thereby leaves the negatively charged head group exposed. The negative charge of a saponin complex adjuvant may be increased, for example, by the addition of negatively charged lipid during complex formation.

Examples of detergents which can increase the negative charge of a carrier include, but are not limited to cholic acid, deoxycholic acid, taurocholic acid and taurodeoxycholic acid. Examples of lipids which can increase the negative charge of a carrier include, but are not limited to, phospholipids (preferably phosphatidyl inositol, phosphatidyl serine, phosphatidyl glycerol and phosphatide acid and most preferably cardiolipin) and bacterial lipids (preferably monophosphoryl lipid A(MPL) and most preferably diphosphoryl lipid A such as OM174 as described in International Patent Publication No. WO 95/14026).

Without limiting the present invention in any way, the inventors have determined that where the subject charged organic carrier and charged antigen are naturally negatively and positively charged, respectively, the object of the invention can be achieved. However, a still more effective immunogenic complex is achieved if the subject naturally negatively charged organic carrier is rendered more negatively charged (preferably by addition of cardiolipin or diphosphory lipid A) and/or the subject naturally positively charged antigen is rendered more positively charged (preferably by addition of a polylysine tail). Preferably, both the naturally negatively charged organic carrier is rendered more negatively charged and the naturally positively charged antigen is rendered more positively charged.

Accordingly, in one preferred embodiment there is provided an immunogenic complex comprising a negatively charged adjuvant and a positively charged protein, wherein said negatively charged adjuvant is a naturally negatively charged adjuvant which has been modified to increase the degree of its negative charge, which adjuvant and protein are electrostatically associated.

In another preferred embodiment there is provided an immunogenic complex comprising a negatively charged adjuvant and a positively charged protein, wherein said positively charged protein is a naturally positively charged protein which has been modified to increase the degree of its positive charge, which adjuvant and protein are electrostatically associated.

In a most preferred embodiment that is provided an immunogenic complex comprising a negatively charged adjuvant and a positively charged protein, wherein said negatively charged adjuvant is a naturally negatively charged adjuvant which has been modified to increase the degree of its negative charge and said positively charged protein is a naturally positively charged protein which has been modified to increase the degree of its positive charge, which adjuvant and protein are electrostatically associated.

Reference to an adjuvant or protein being "naturally" negatively or positively charged, respectively, should be understood as a reference to the charge which the molecule bears upon its creation—whether that be by natural, recombinant or synthetic means. Modification to increase the degree of charge can be achieved by any suitable technique as hereinbefore discussed. Preferably, the subject protein is rendered more positively charged via the addition of a polylysine tail and the subject adjuvant is rendered more negative via the addition of cardiolipin or diphosphoryl lipid A.

Reference to "derivative and equivalents" should be understood as a reference to fragments, parts, portions, chemical equivalents, mutants, homologs and analogs from natural, synthetic or recombinant sources. Where the subject antigen or carrier is a protein, derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence.

Substitutional amino acid variants are those in which one residue in the sequence has been removed and a different residue inserted in its place. Additions to amino acid sequences include fusions with other peptides, polypeptides or proteins. "Equivalents" can act as a functional analog of the subject carrier or antigen. Chemical equivalents may not necessarily be derived from the subject carrier of antigen but may share certain conformational similarities. Alternatively, chemical equivalents may be designed to mimic certain physiochemical properties of the subject carrier or antigen. Equivalents may be chemically synthesized or may be detected following, for example, natural product screening. Homologs contemplated herein include, but are not limited to, molecules derived from different species.

The present invention is predicated, in part, on the formation of immunogenic complexes via the electrostatic association, preferably, of a negatively charged organic carrier with a positively charged antigen. The administration of such a complex to a subject facilitates the induction of a significantly better immune response than would be achieved were the adjuvant and antigen administered simultaneously but in a non-associated form. In particular, the administration of an antigen associated with an adjuvant, according to the present invention, facilitates the induction of a cytotoxic T-lymphocyte response to the antigen. However, humoral and other cellular responses can also be enhanced.

Without limiting the present invention to any one theory or mode of action, it is thought that the complexing of the adjuvant with the antigen facilitates co-delivery of the adjuvant and the antigen to the same antigen presenting cell thereby facilitating the induction of immune responses which either would not occur or would not occur as effectively were these molecules not co-delivered. For example, the induction of some CD8+ cytotoxic T-lymphyocyte responses are thought to occur where the adjuvant induces endosomal escape of the antigen in the antigen presenting cell. This necessarily requires co-delivery of the antigen and the adjuvant to the antigen presenting cell.

A further aspect of the present invention therefore relates to the use of the invention to induce an immune response in a mammal including, but not limited to, a humoral and/or cell mediated immune response.

Accordingly, another aspect of the present invention relates to a vaccine composition comprising as the active component an immunogenic complex comprising a charged organic carrier and a charged antigen which organic carrier and antigen are electrostatically associated together with one or more pharmaceutically acceptable carriers and/or diluent.

Preferably, said organic carrier is an adjuvant, and even more preferably a saponin or a saponin complex. Preferably said saponin complex is ISCOMATRIX™.

Still more preferably, said antigen is a protein.

Preferably said organic carrier is negatively charged and said antigen is positively charged.

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The organic carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filter sterilisation. Generally, dispersions are prepared by incorporating the various sterilised active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated, directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 2000 mg of active compound.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

Without limiting the operation of the present invention in any way, the co-delivery of the immunogenic complex of the present invention is particularly useful for inducing an immune response and, in particular, a cytotoxic T-lymphocyte response to an antigen said immune response may be a specific (T cell and/or B cell) and/or non-specific immune response.

Accordingly, still another aspect of the present invention relates to a method of eliciting, inducing or otherwise facilitating, in a mammal, an immune response to an antigen said method comprising administering to said mammal an effective amount of an immunogenic complex or a vaccine composition as hereinbefore described.

Preferably said immune response is a cytotoxic T-lymphocyte response.

It should be understood mat the subject cytotoxic lymphocyte response may occur either in isolation or together with a helper T cell response, a humoral response or other specific or non-specific immune response.

A further aspect of the present invention relates to the use of the immunogenic complex of the invention in relation to the therapeutic and/or prophylactic treatment of disease conditions. Examples of disease conditions which can be treated in accordance with the method of the present invention include, but are not limited to, any disease condition which results from a microbial Infection or a cancer. Examples include HTV, Hepatitis B, Hepatitis C, melanoma, prostate cancer, breast cancer, tuberculosis and parasitic conditions.

Accordingly, yet another aspect of the present invention relates to a method of treating a disease condition in a mammal said method comprising administering to said mammal an effective amount of an immunogenic complex or a vaccine composition as hereinbefore described wherein administering said composition elicits, induces or otherwise facilitates an immune response which inhibits, halts, delays or prevents the onset or progression of the disease condition.

An "effective amount" means an amount necessary at least partly to attain the desired immune response, or to delay the onset or inhibit progression or halt altogether, the onset or progression of a particular condition being treated. This amount varies depending upon the health and physical condition of the individual to be treated, the taxonomic group of individual to be treated, the capacity of the individual's immune system to synthesize antibodies, the degree of protection desired, the formulation of the vaccine, the assessment of the medical situation, and other relevant factors. It is expected that the amount will fall in a relatively broad range that can be determined through routine trials.

The term "mammal" includes humans, primates, livestock animals (eg. horses, cattle, sheep, pigs, donkeys), laboratory test animals (eg. mice, rats, rabbits, guinea pigs), companion animals (eg. dogs, cats) and captive wild animals (eg. kangaroos, deer, foxes). Preferably, the mammal is a human or laboratory test animal. Even more preferably, the mammal is a human.

The mammal undergoing treatment may be human or an animal in need of therapeutic or prophylactic treatment of a disease condition or a potential disease condition.

In yet another aspect the present invention relates to the use an immunogenic complex or vaccine composition as hereinbefore defined in the manufacture of a medicament for inhibiting, halting, delaying or preventing the onset or progression of a disease condition.

Yet another aspect of the present invention relates to an agent for use in inhibiting, halting, delaying or preventing the onset or progression of a disease condition. Said agent comprising an immunogenic complex or vaccine composition as hereinbefore defined.

Further features of the present invention are more fully described in the following non-limiting Examples.

Reference to "ISCOPREP™ 703" should be understood as a reference to a saponin preparation comprising from 50-90% by weight of Fraction A of Quil A and 50% to 10% by weight of Fraction C of Quil A. Fractions A and C are prepared from the lipophilic fraction of Quil A. Fractions "A" and "C", (heir method of preparation and the method of preparing 703 are detailed in International Patent Publication No. WO96/11711, which is incorporated herein by reference.

EXAMPLE 1

Preparation of Standard and Modified ISCOMATRIX™

ISCOMATRIX™ (Immunostimulating complex without antigen) was prepared essentially by the method of Morein et al. (1989). Briefly, to 1.76 ml PBS pH 7.2 was added 0.16 ml of a solution containing 10 mg/ml tritiated ($^3$H) cholesterol and 10 mg/ml lipid in 20% MEGA-10 detergent (w/v) then 0.08 ml of a solution containing 100 mg/ml ISCOPREP™ 703 in PBS. The solution was held at 25° C. for 1 hour with gentle mixing. During subsequent dialysis against PBS/azide, ISCOMATRIX™ containing cholesterol, DPPC and ISCOPREP™ was formed. All the ISCOMATRIX™ formulations were of typical appearance by electron microscopy.

| | Lipids: |
|---|---|
| Standard DPPC | dipalmitoylphosphatidylcholine |
| CDL modified | cardiolipin |
| DPL modified | diphosphoryl lipid A |
| MPL modified | monophosphoryl lipid A |
| DPA modified | phosphatidic acid |
| DPPG modified | dipalmitoylphosphatidyl glycerol |

DPPG modified dipalmitoylphosphatidyl glycerol

After formulation, preparations were purified on a sucrose gradient (10 to 50% w/v) and fractions analysed for lipid and cholesterol. Cholesterol was detected by $^3$H cpm of 100 μl sample in 1 ml scintillant and lipid was detected using diphenylhexatriene (DPH) which fluoresces when associated with lipid. Briefly, DPH was dissolved at 1 mg/ml in acetone then diluted 1 in 50 in PBS pH7.2, then 50 μl mixed with 50 μl of each fraction in a microtitre plate. Following incubation for 150 mins at 20-25° C. the plate was read in a fluorometer using excitation 355 nm and emission 460 nm. The DPH and $^3$H peaks coincided for all formulations and the gradient profiles of the modified formulations were similar to the standard formulation indicating incorporation of the lipid into the ISCOMATRIX™ (FIG. 1).

EXAMPLE 2

Preparation of Antigen Associated ISCOMATRIX™ with a Naturally Positively Charged Protein: *H. pylori* Family E Protein(HpE)

The HpE protein has a pI of 9.24 making it a postively charged protein at pH8. Solubility of the HpE was maintained using 0.5M Tris, 0.5M NaCl, 0.1% 1,2-Diheptanoyl-sn-Glycero-3-phosphocholine (DHPC) pH8. The HpE associated ISCOMATRIX™ formulations were prepared by mixing at a 1:5 ratio of protein to ISCOPREP™ as ISCOMATRIX™ for 60 minutes at 20-25° C. The ISCOMATRIX™ formulations used were DPPC, CDL, DPL and DPPG.

After formulation, preparations were purified on a sucrose gradient (10 to 50% sucrose w/v) and fractions analysed for HpE, association between HpE and ISCOMATRIX™ and ISCOMATRIX™ (FIG. 2). HpE was detected by adsorbing fractions diluted 1 in 10 in PBS to wells of an EIA plate then detecting with a Horse radish peroxidase (HRP) conjugated monoclonal antibody to HpE. Association was determined by EIA using a monoclonal antibody to HpE to capture and a HRP conjugated monoclonal antibody to ISCOPREP™ to detect. ISCOMATRIX™ was determined by detecting 3H cholesterol.

Figure 2A:
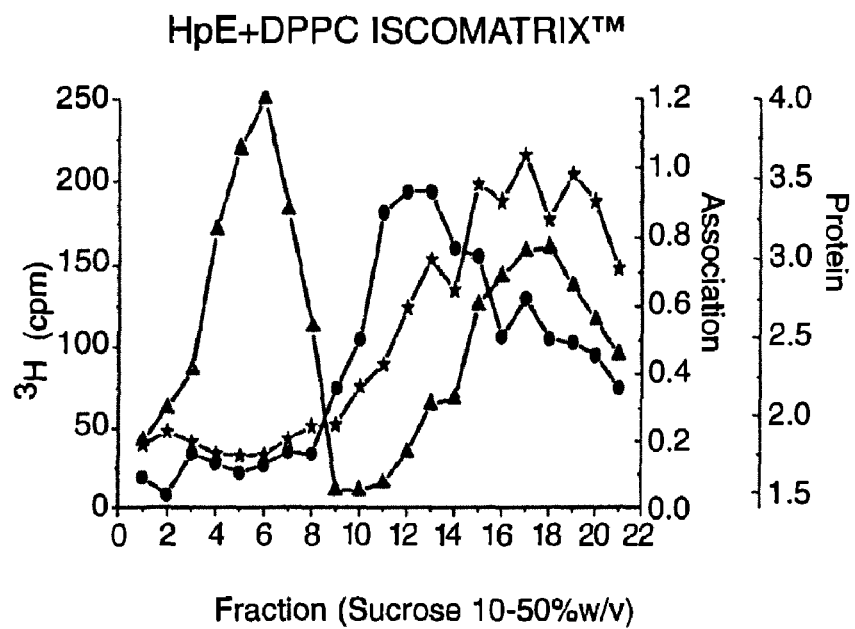
FIG. 2 is a graphical representation of the sucrose gradient analysis of four of the ISCOMATRIX™ formulations of Example 1 after mixing with HpE. It can be seen that most of the HpE is with CDL and DPL ISCOMATRIX™ but only part is associated with DPPC and DPPG ISCOMATRIX™.
Figure 2B:
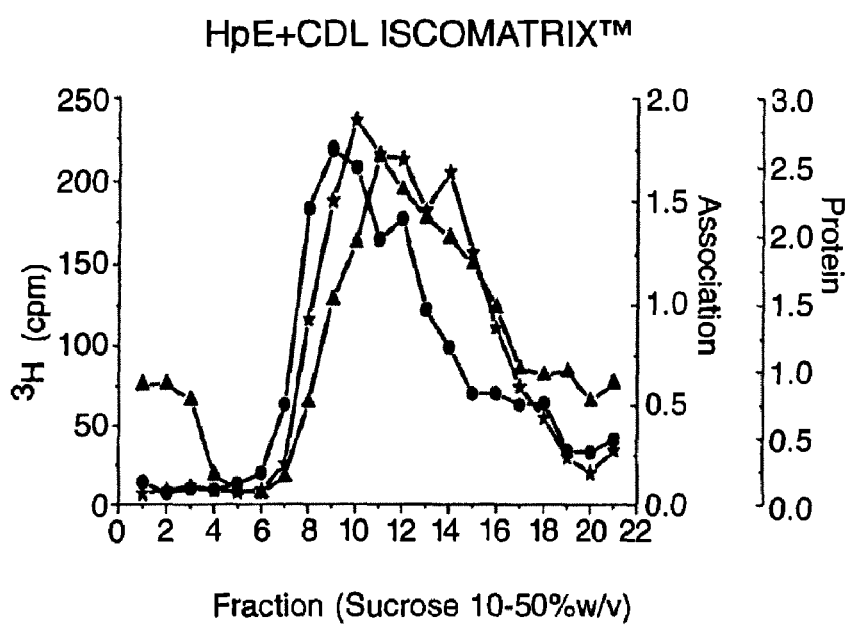
Figure 2C:
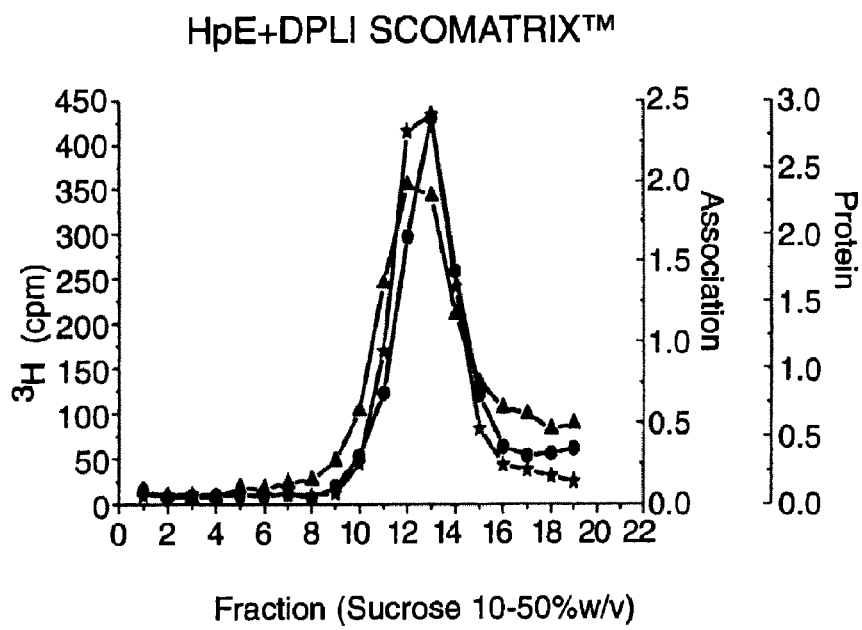
Figure 2D:
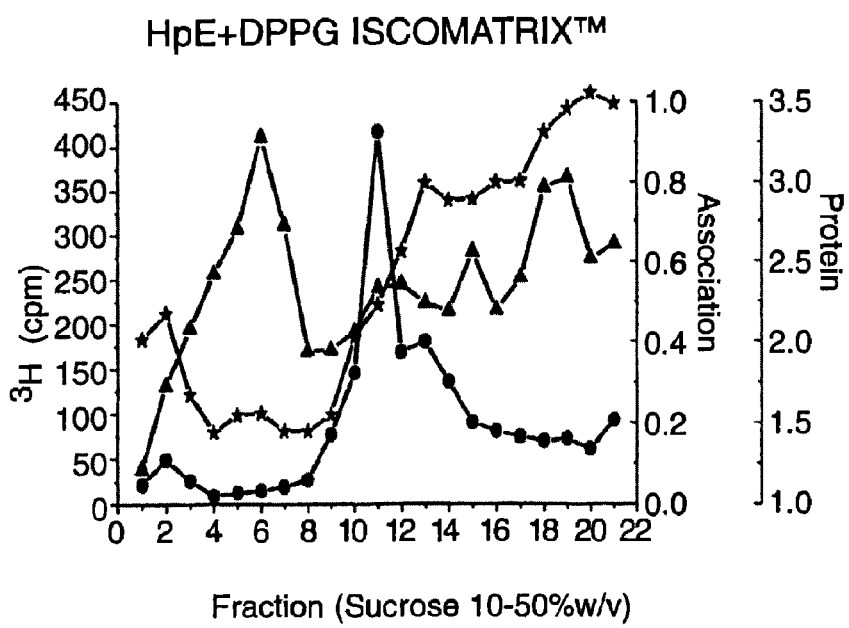
Figure 2E:
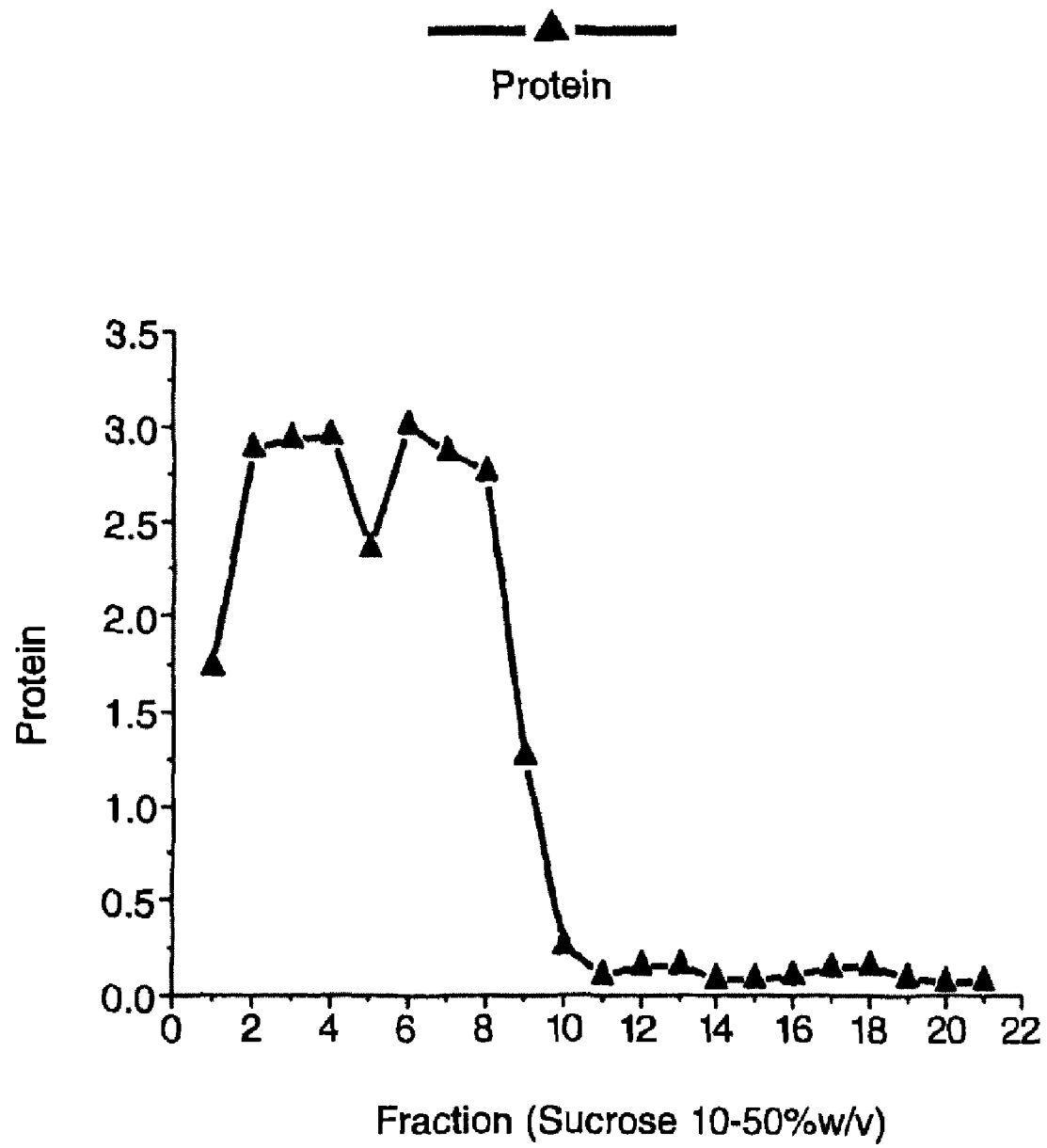

The HpE protein, when not mixed with ISCOMATRIX™, was found in fractions 3-10 by EIA. (FIG. 2E). When mixed with DPPC ISCOMATRIX™ the HpE was found predominantly in fractions 2-8 but some was found in fractions 12-20 coinciding with the ISCOMATRIX™ and association peaks which indicates that association occurred (FIG. 2A). When mixed with CDL or DPL ISCOMATRIX™ the HpE was found predominantly in fractions 7-16 coinciding with the ISCOMATRIX™ and association peaks which indicates that almost complete association occurred (FIGS. 2B&C). There was very little, if any, free HpE found in fractions 2-8. When mixed with DPPG ISCOMATRIX™ the results were similar to the DPPC ISCOMATRIX™ (FIG. 2D).

These results indicate that DPPG and standard DPPC ISCOMATRIX™ can associate weakly with antigens that are positively charged and the capacity to associate can be substantially increased by using CDL or DPL ISCOMATRIX™.

EXAMPLE 3

Preparation of Antigen Associated ISCOMATRIX™ with a Naturally Positively Charged Protein: NY-ESO-1 (ESO)

The ESO protein has a pI of 9.1 making it a positively charged protein at pH7. Solubility of the ESO was maintained using 8M Urea, 50 mM Tris, 50 mM $NaH_2PO_4.2H_2O$, 0.15M NaCl pH7. The ESO associated ISCOMATRIX™ formulations were prepared by mixing at a 1:5 ratio of protein to ISCOPREP™ as ISCOMATRIX™ for 60 minutes at 20-25° C. The ISCOMATRIX™ formulations used were DPPC and DPL.

After formulation, preparations were purified on a sucrose gradient (10 to 50% sucrose w/v) and fractions analysed for ESO, association between ESO and ISCOMATRIX™ and ISCOMATRIX™ (FIG. 3). ESO was detected by adsorbing fractions diluted 1 in 10 in PBS to wells of a EIA plate then detecting with a HRP conjugated monoclonal antibody to ESO. Association was determined by EIA using a monoclonal antibody to ESO to capture and a HRP conjugated monoclonal antibody to ISCOPREP™ to detect. ISCOMATRIX™ was determined by detecting $^3H$ cholesterol.

Figure 3A:
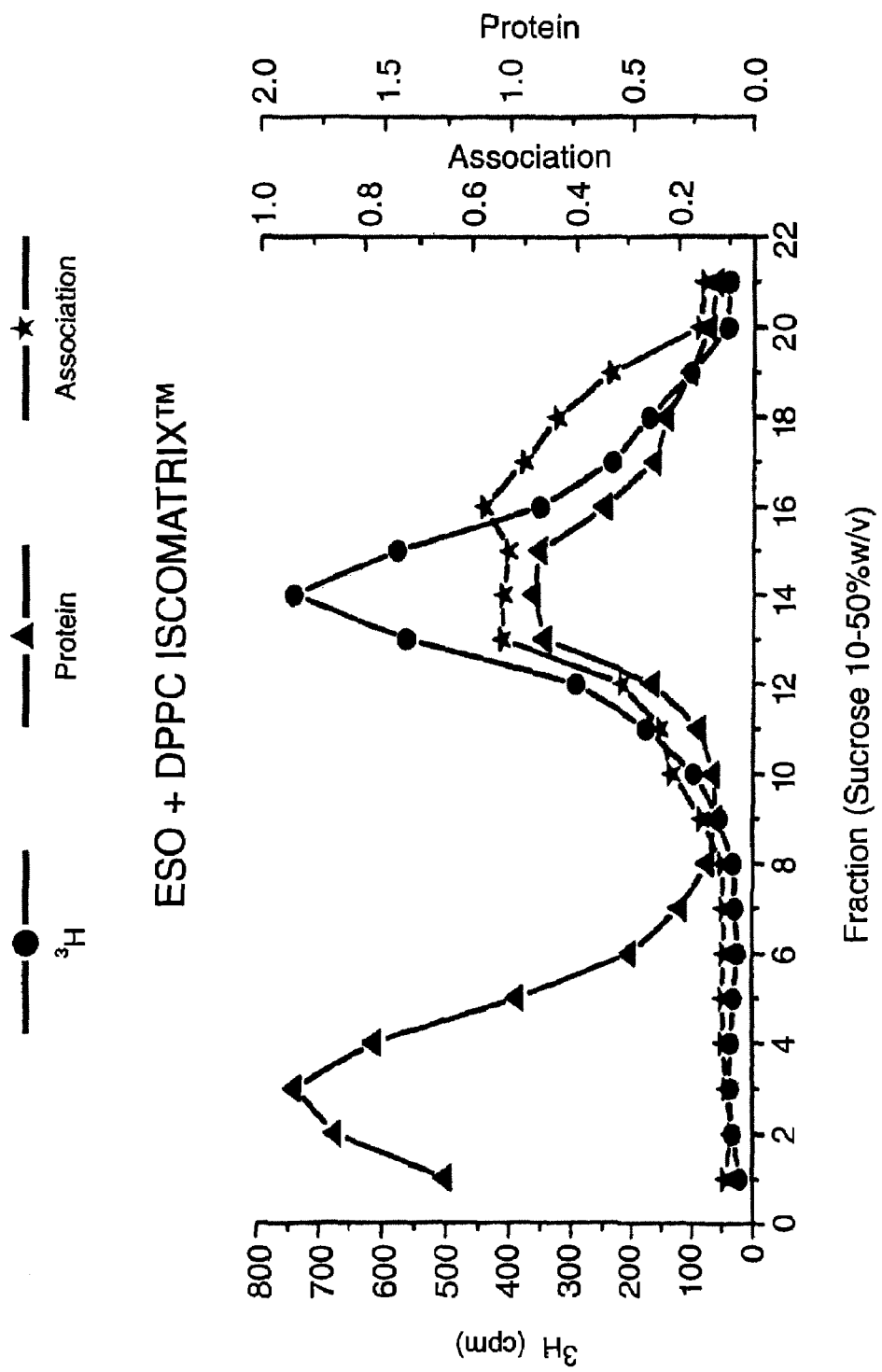
FIG. 3 is a graphical representation of the sucrose gradient analysis of two of the ISCOMATRIX™ formulations of Example 1 after mixing with ESO. It can be seen that most of the ESO is associated with DPL ISCOMATRIX™ but only part is associated with DPPC ISCOMATRIX™.
Figure 3B:
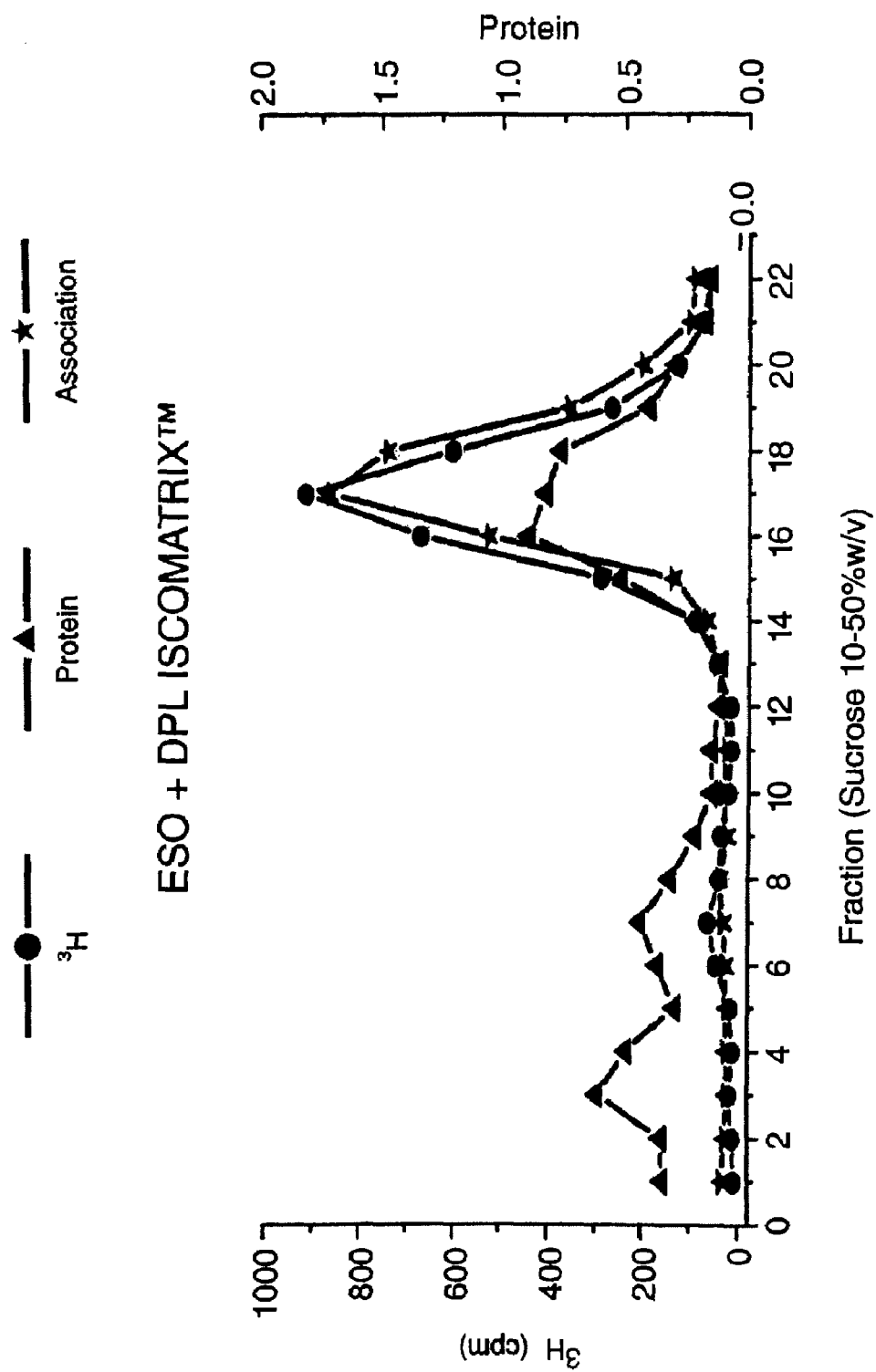
Figure 3C:
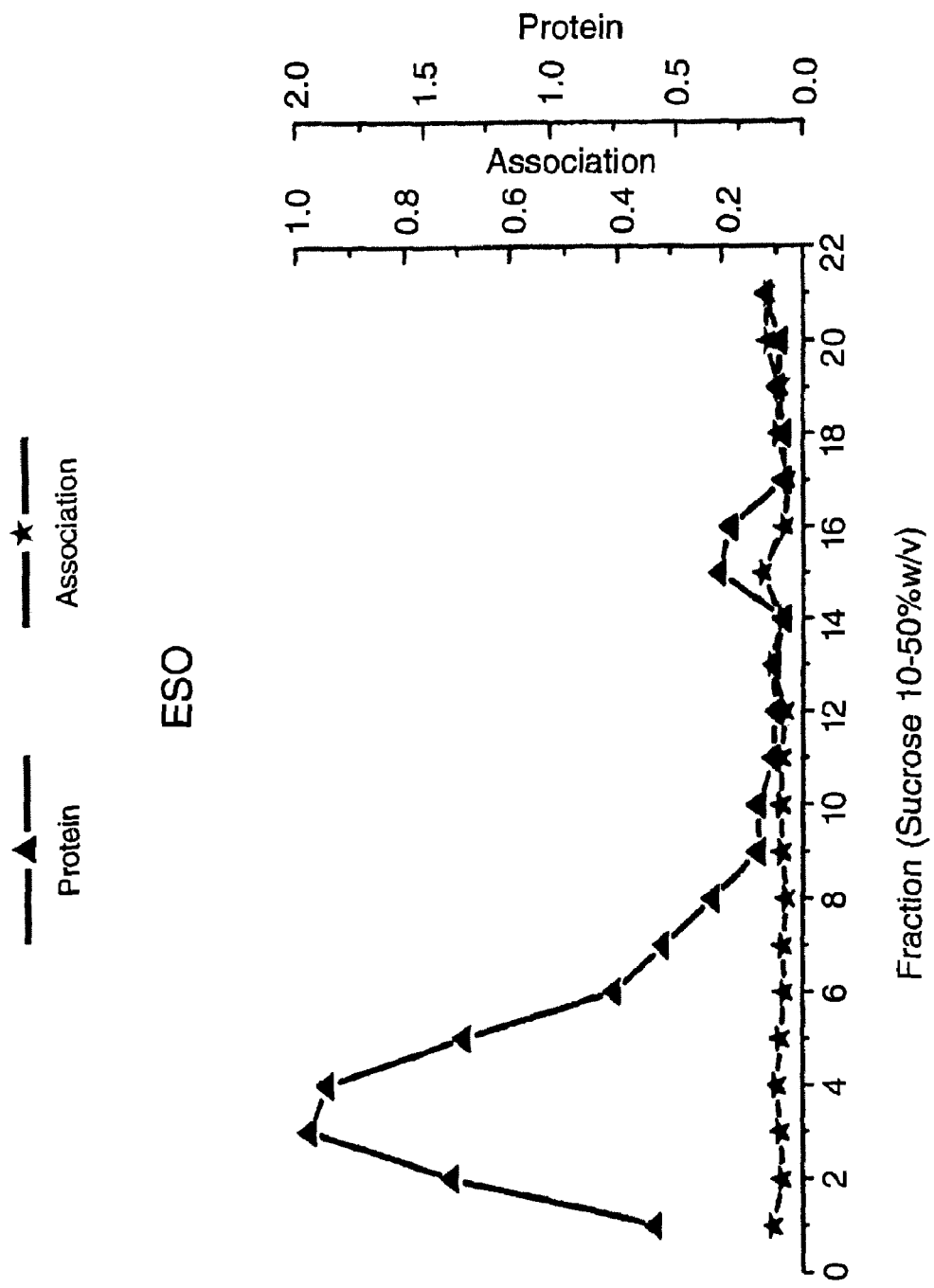

The ESO protein, when not mixed with ISCOMATRIX™, was found in fractions 1-6 by EIA. (FIG. 3C). When mixed with standard DPPC ISCOMATRIX™ ESO was found in fractions 1-6 and 12-16 (FIG. 3A). The presence in fractions 12-16 coincided with the ISCOMATRIX™ and association peaks indicating there was association but a large proportion of the ESO was not associated as indicated by the presence in fractions 1-6. When mixed with DPL ISCOMATRIX™ the ESO was found predominantly in fractions 12 to 16 coinciding with the ISCOMATRIX™ and association peaks which indicates that association occurred (FIG. 3B).

These results show there was some association of a positively charged protein with standard DPPC ISCOMATRIX™ but the capacity to associate was substantially increased by use of DPL ISCOMATRIX™.

EXAMPLE 4

Immunisation of Mice with ESO Associated Standard ISCOMATRIX™

Antibody Responses:

Ten BALB/c mice were immunised, on days 0 and 28, subcutaneously in the scruff of the neck with 0.1 ml of ESO containing 5 µg protein or ESO associated ISCOMATRIX™ containing 5 µg protein and 5 µg ISCOPREP™. The mice were bled on day 35 and the sera analysed for antibodies to ESO by indirect EIA. Briefly, ESO was adsorbed to a microtitre plate in PBS pH7.2 then the plate blocked with a 0.1% casein solution and dried. Dilutions of sera were incubated for 1 hour at 20-25° C. then the plates washed. HRP conjugated goat anti mouse IgG, $IgG_1$ or $IgG_{2a}$ was added and plates incubated for 1 hour at 20-25° C. then washed. TMB substrate was added and incubated for 10 mins at 20-25° C. followed by addition of 0.5M $H_2SO_4$ to stop the reaction. Plates were read at OD450 nm and end point titres calculated.

Figure 4:
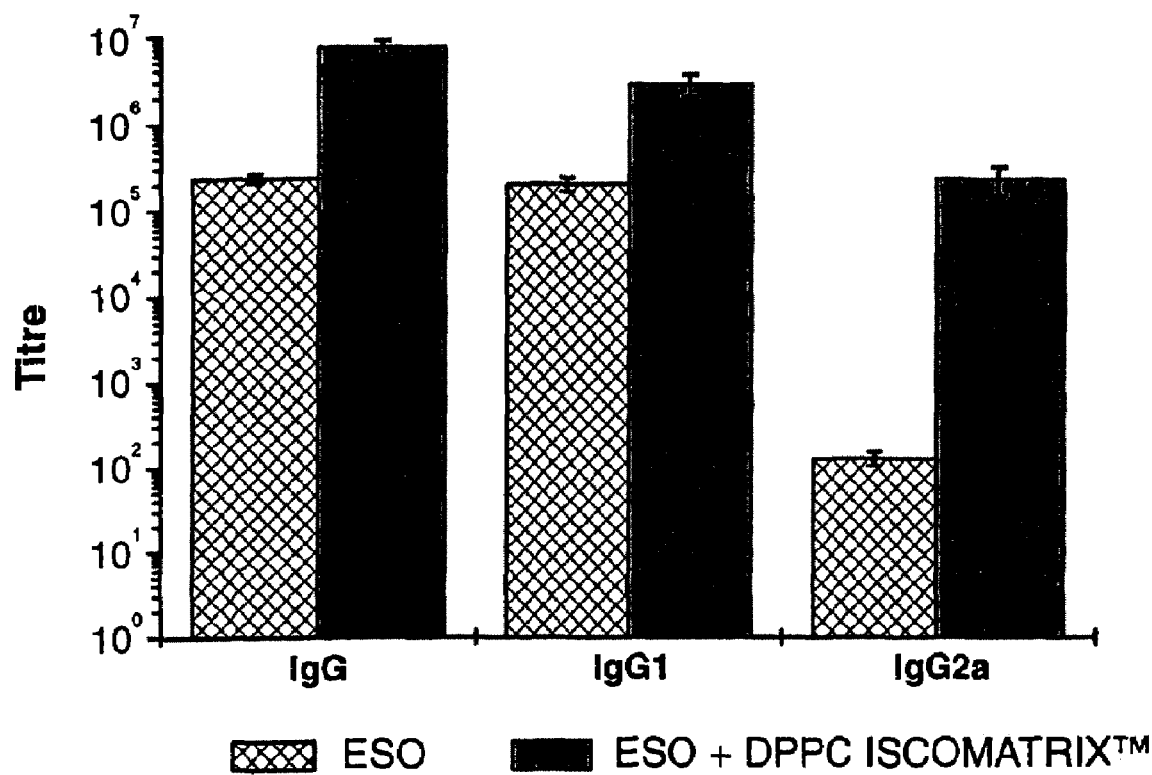
Figure 5A:
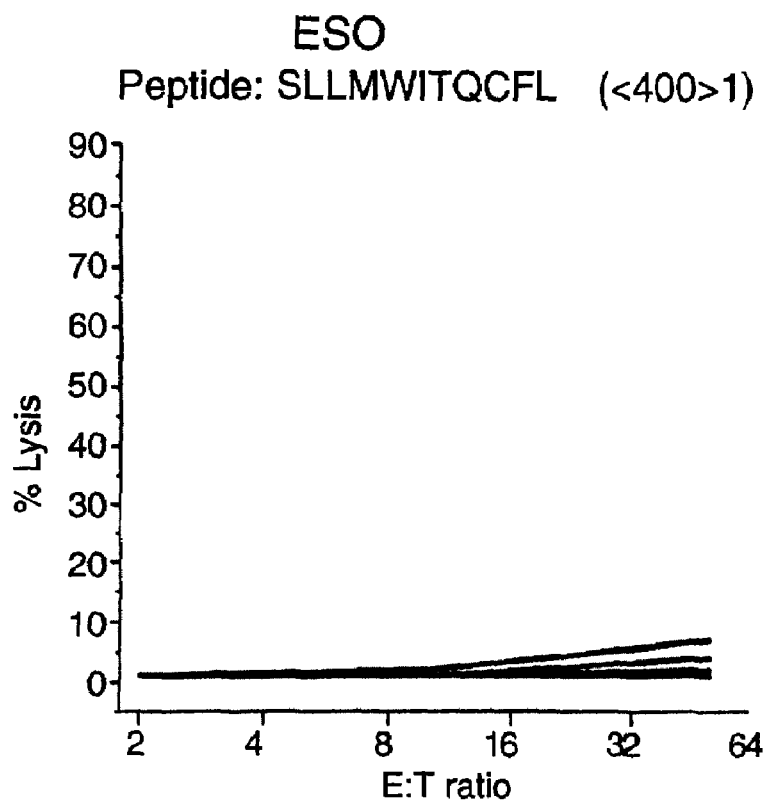
FIG. 5 is a graphical representation of CTL analysis of mice immunised with ESO (FIGS. 5A, 5C) and ESO associated ISCOMATRIX™ (FIGS. 5B, 5D) using SLLM-WITQCFL (<400>1)(FIGS. 5A, 5B) and SLLMWITQC (<400>2) (FIGS. 5C, 5D) peptides for stimulation and targets. It can be seen that ESO associated ISCOMATRIX™ induces a CTL response but ESO alone does not.
Figure 5B:
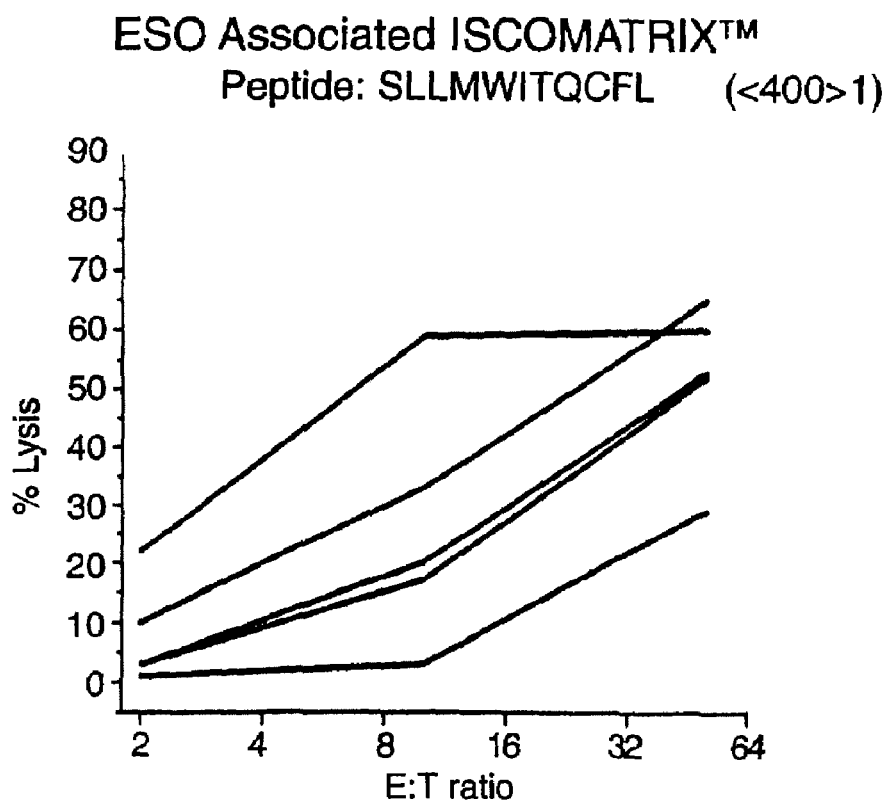
Figure 5C:
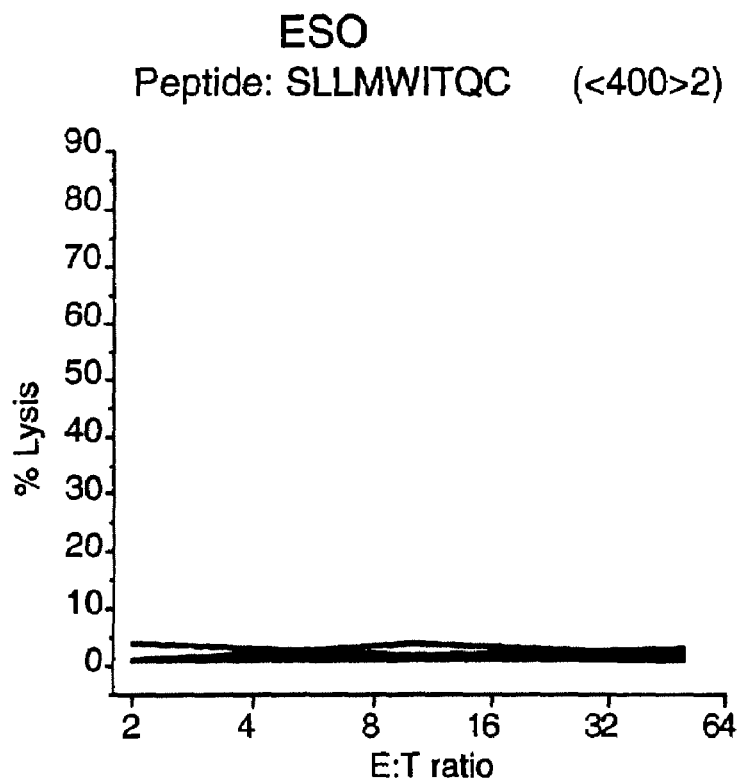
Figure 5D:
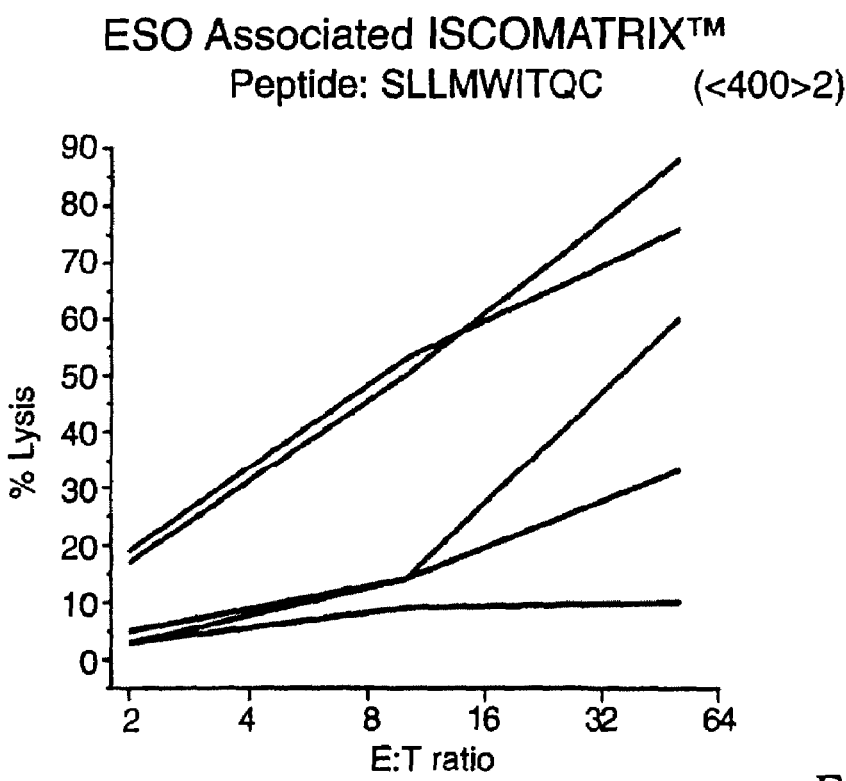

There was a greater than 20 fold increase in the IgG and $IgG_1$ responses to ESO when associated with ISCOMATRIX™ and a thousand fold increase in $IgG_{2a}$ litre (FIG. 4).

Cytotoxic T Lymphocyte (CTL) Responses:

Five HLA A2 transgenic HHD mice were immunised subcutaneously at the base of the tail with 0.1 ml of ESO containing 5 µg protein or ESO associated ISCOMATRIX™ containing 5 µg protein and 5 µg ISCOPREP™. After 14 days splenocytes were harvested and $5\times10^6$ cells restimulated in 24-well plates with EL4HHD cells sensitised with ESO peptide (10 µg/ml for 1 hour 37° C.), irradiated and washed twice. Cells were cultured in RPMI media supplemented with 10% foetal calf serum, 2 mM glutamine, $5\times10^{-5}$ Mβ-mercaptoethanol, 100 µg/ml strepomycin and 100IU/ml pencillin and incubated at 37° C. for 6 days in 5% $CO_2$. On day 4 1 ml of medium was added containing 5 U/ml recombinant human IL-2. On day 6 the cultures were used as effectors in standard 6 hour $^{31}Cr$ release assays against EL4HHD cells sensitised as for restimulation.

CTL were not detected in mice immunised with ESO alone but when associated with ISCOMATRIX™, CTL was detected in all mice (FIG. 5).

These results indicate that association is required for optimal induction of cellular immune responses.

EXAMPLE 5

Preparation of Antigen Associated Iscomatrix™ with a Naturally Negatively Charged Protein: HPV E6E7 (E6E7)

The E6E7 protein has a pi of 5.9 making it a negatively charged protein at pH6.9. Solubility of the E6E7 was maintained using 8M Urea. 50 mM Tris, 50 mM $NaH_2PO_4.2H_2O$, 150 mM NaCl pH6.9. The E6E7 associated ISCOMATRIX™ formulations were prepared by mixing at a 1:5 ratio of protein to ISCOPREP™ as ISCOMATRIX™ for 60 minutes at 20-25° C. The ISCOMATRIX™ formulations used were DPPC, CDL, DPL, MPL, DPA and DPPG.

Figure 8A:
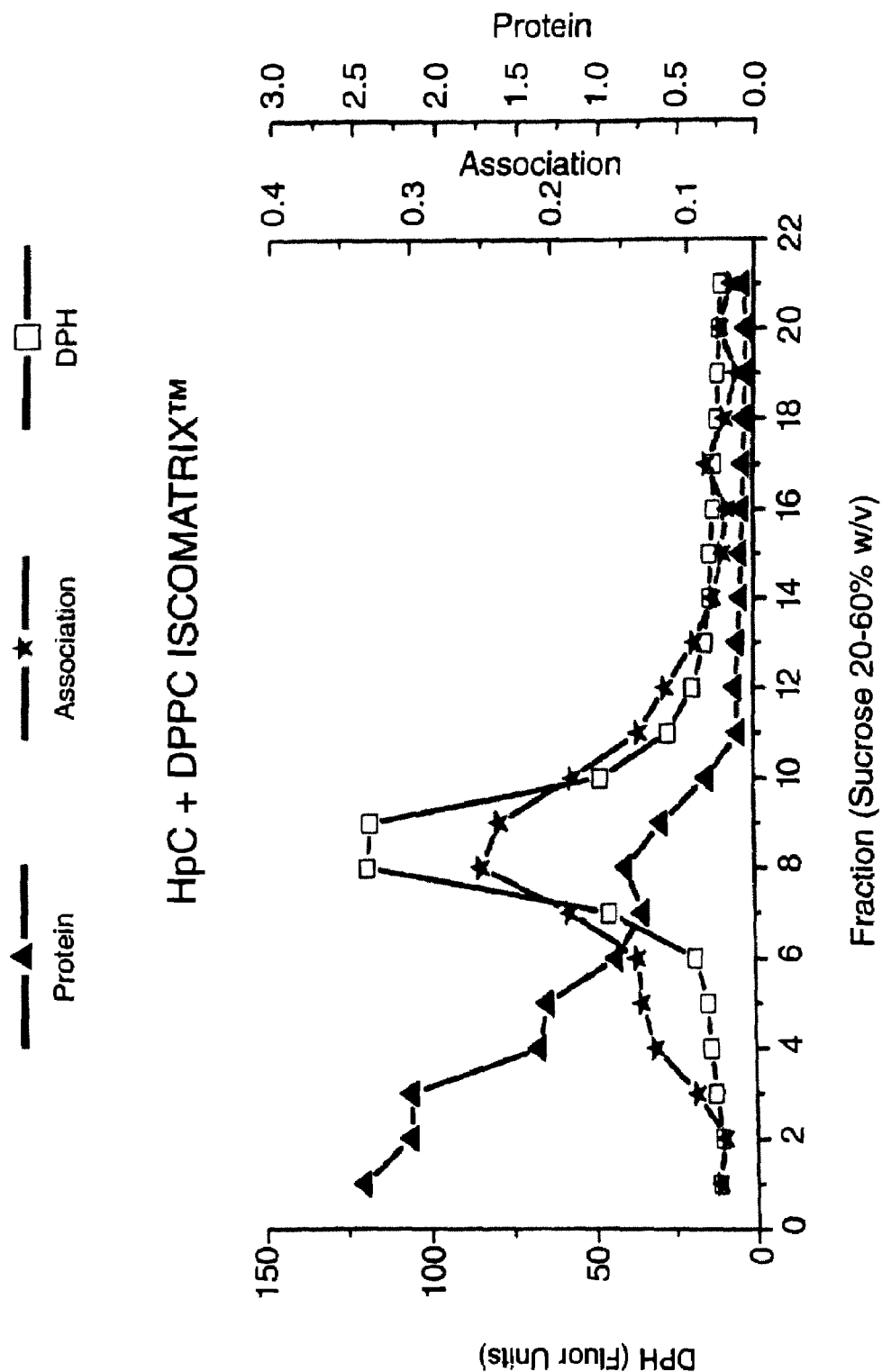
FIG. 8 is a graphical representation of the sucrose gradient analysis of two of the ISCOMATRIX™ formulations from Example 1 after mixing with HpC. It can be seen that more HpC is associated with DPL ISCOMATRIX™ than with DPPC ISCOMATRIX™ where there is very little association.
Figure 8B:
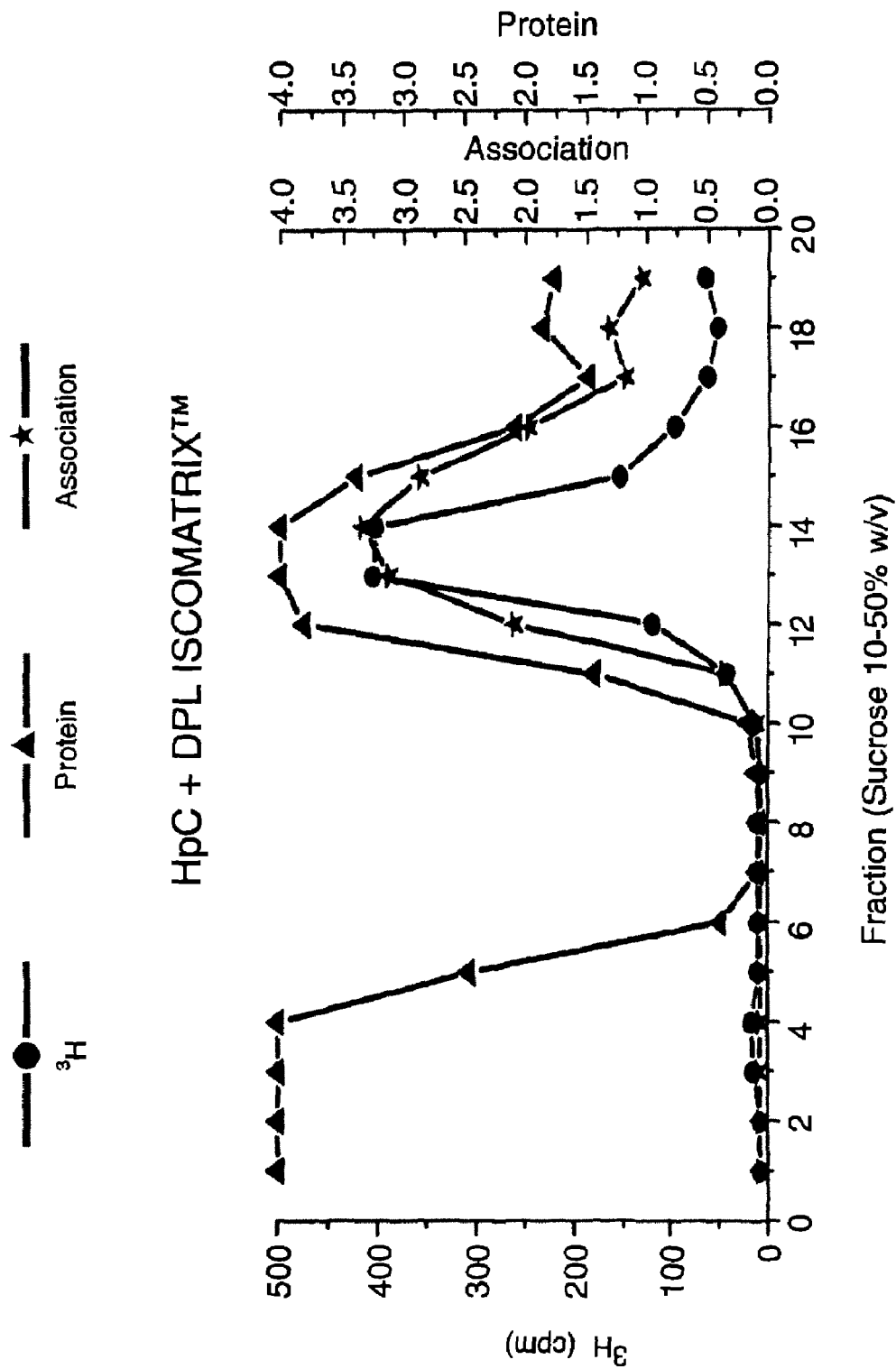
Figure 8C:
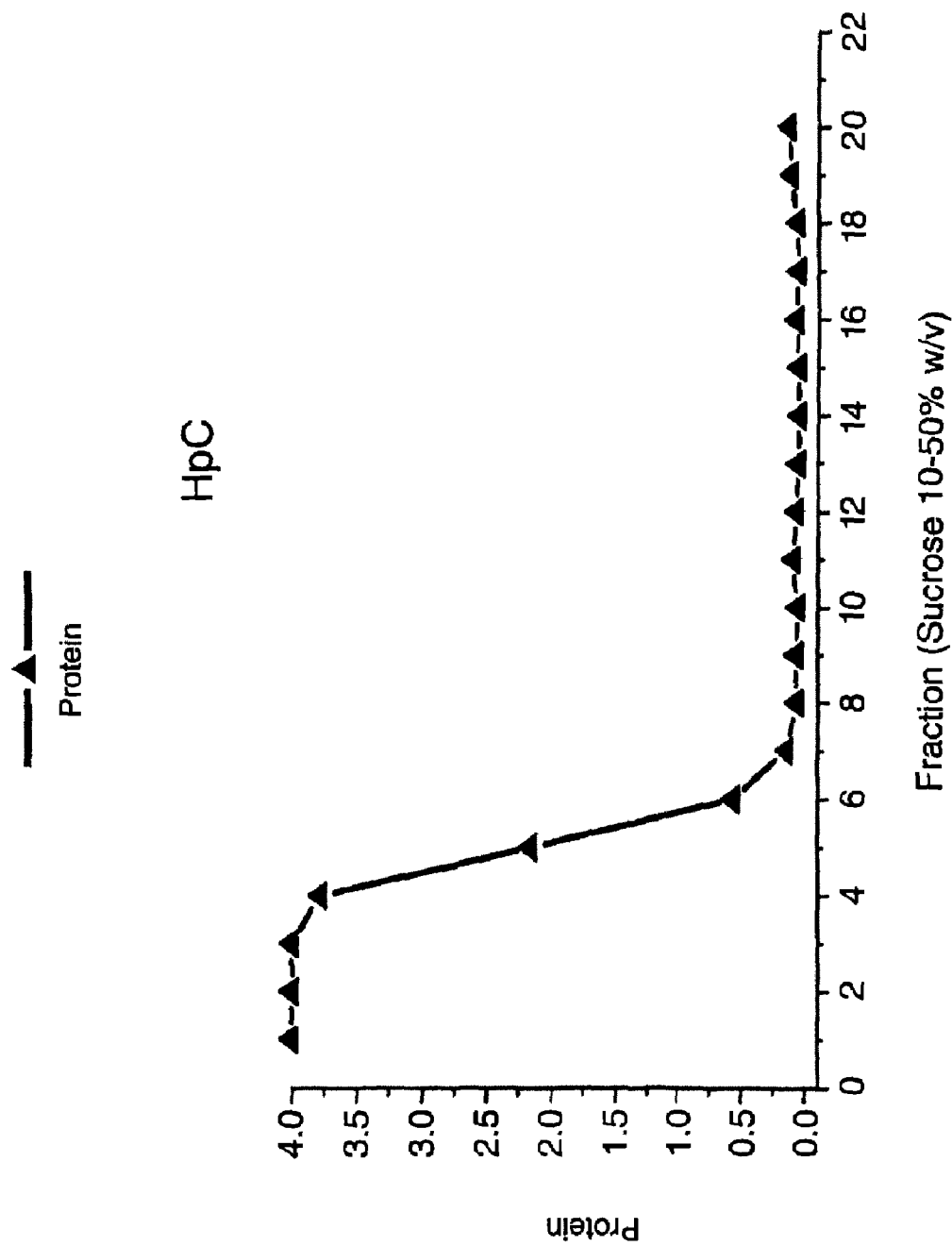

After formulation, preparations were purified on a sucrose gradient (10 to 50% sucrose w/v) and fractions analysed for E6E7, association between E6E7 and ISCOMATRIX™ and ISCOMATRIX™ (FIG. 8). E6E7 was detected by EIA using two non-competing monoclonal antibodies to 7. Association was determined by EIA using a monoclonal antibody to E7 to capture and a HRP conjugated monoclonal antibody to ISCOPREP™ 703 to detect. ISCOMATRIX™ was determined by detection of $^3$H cholesterol.

Figure 6A:
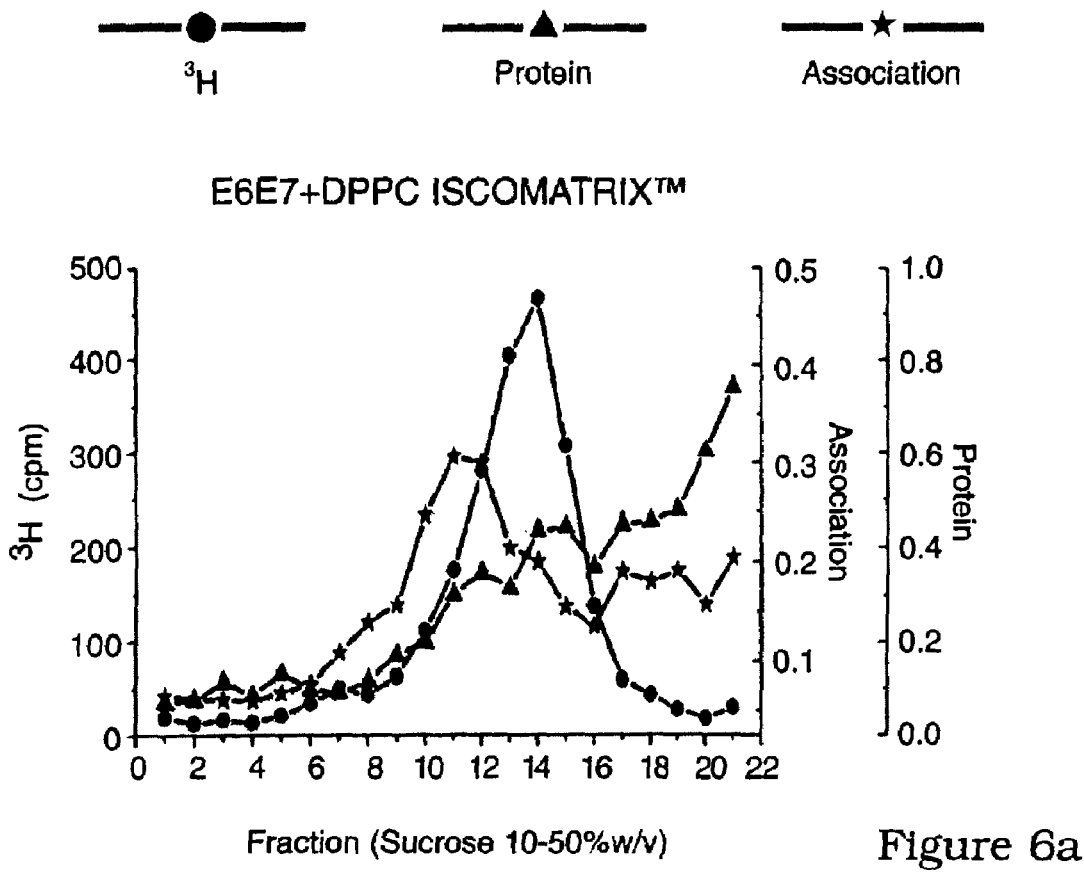
FIG. 6 is a graphical representation of the sucrose gradient analysis of six of the ISCOMATRIX™ formulations of Example 1 after mixing with E6E7. It can be seen that most of the E6E7 is associated with CDL, DPL and DPA ISCOMATRIX™, less associated with the MPL and DPPG ISCOMATRIX™ and even less again with the DPPC ISCOMATRIX™.
Figure 6B:
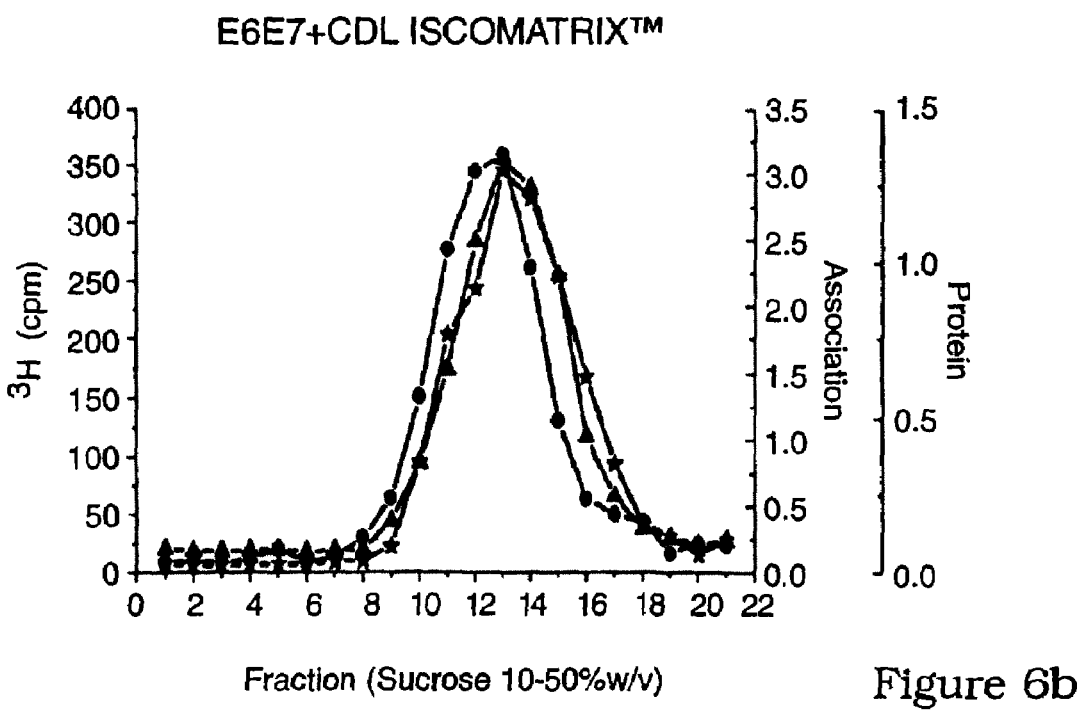
Figure 6C:
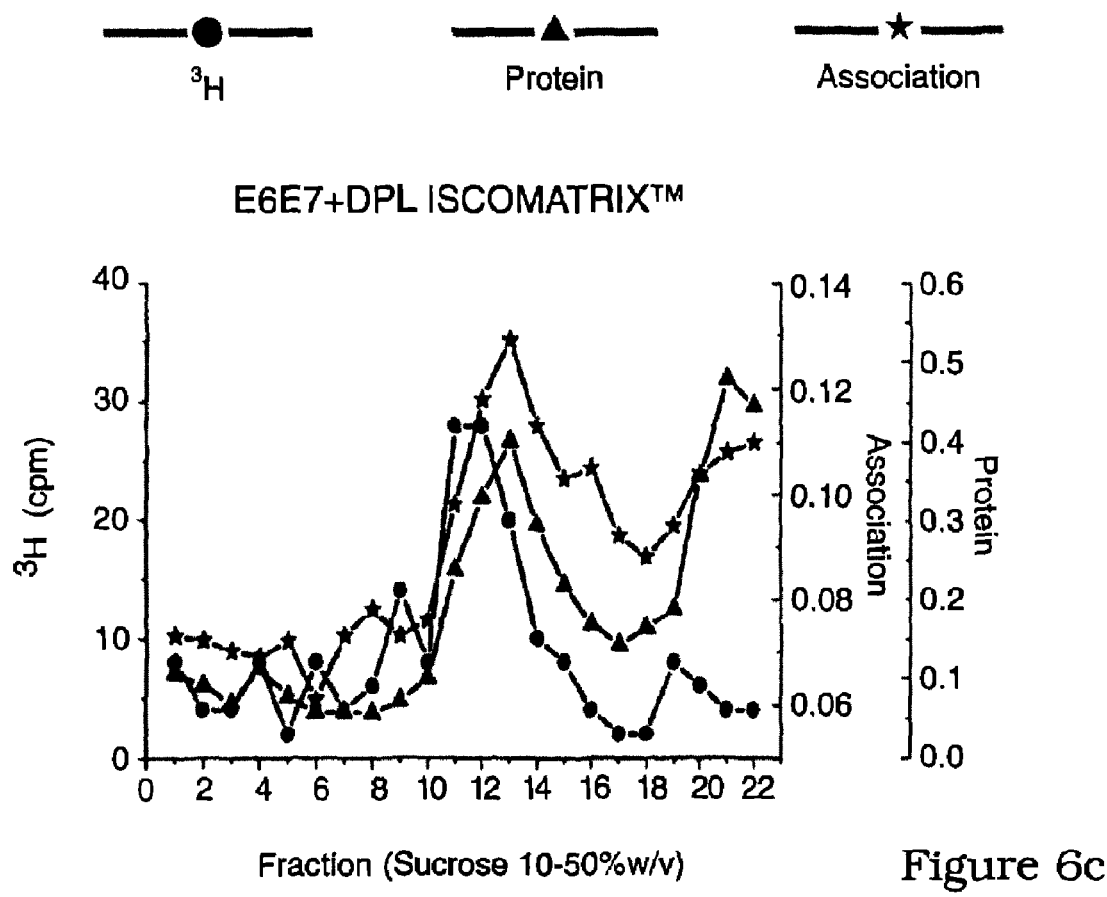
Figure 6D:
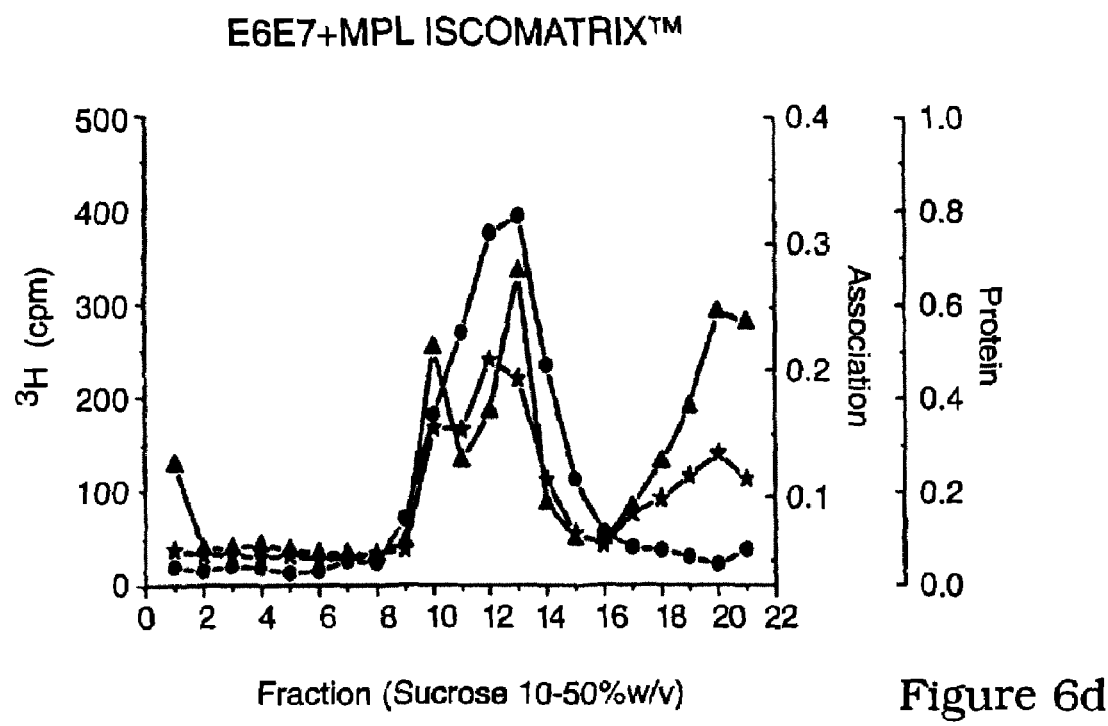
Figure 6E:
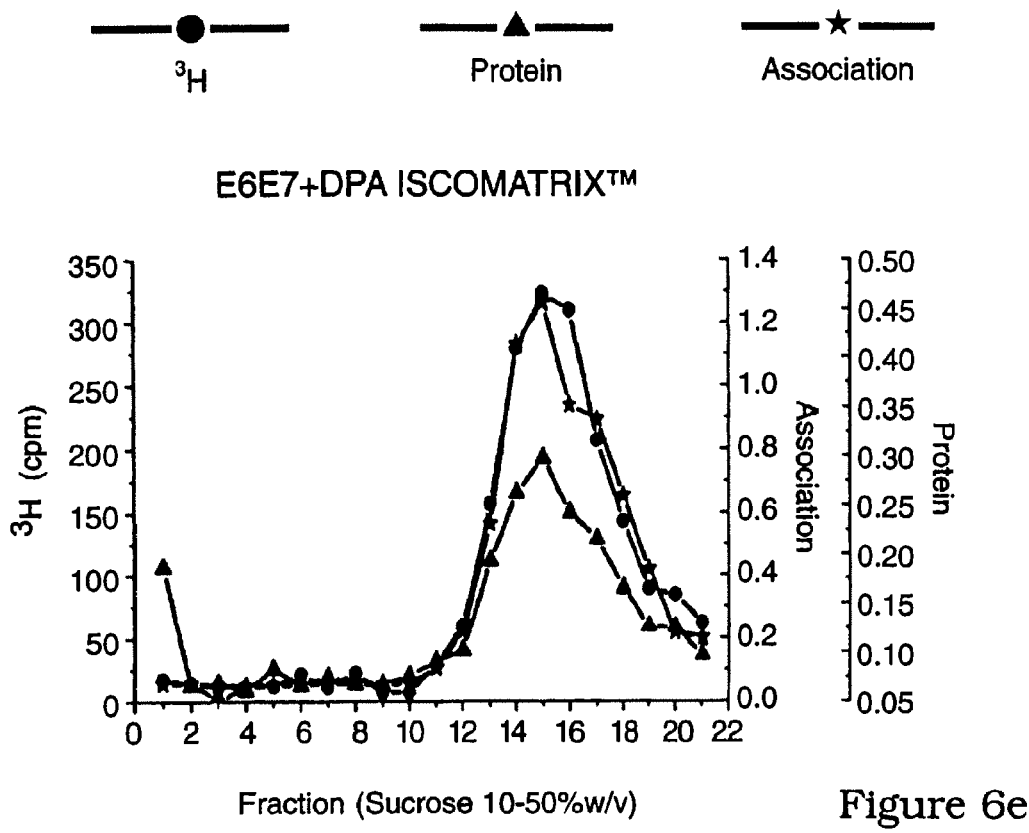
Figure 6F:
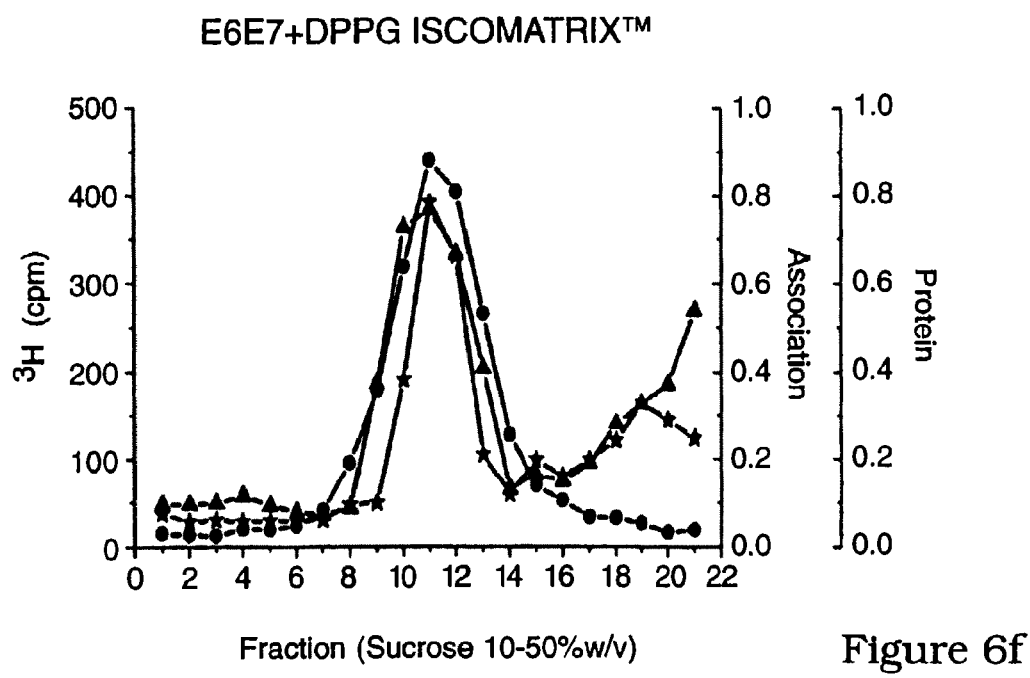
Figure 6G:
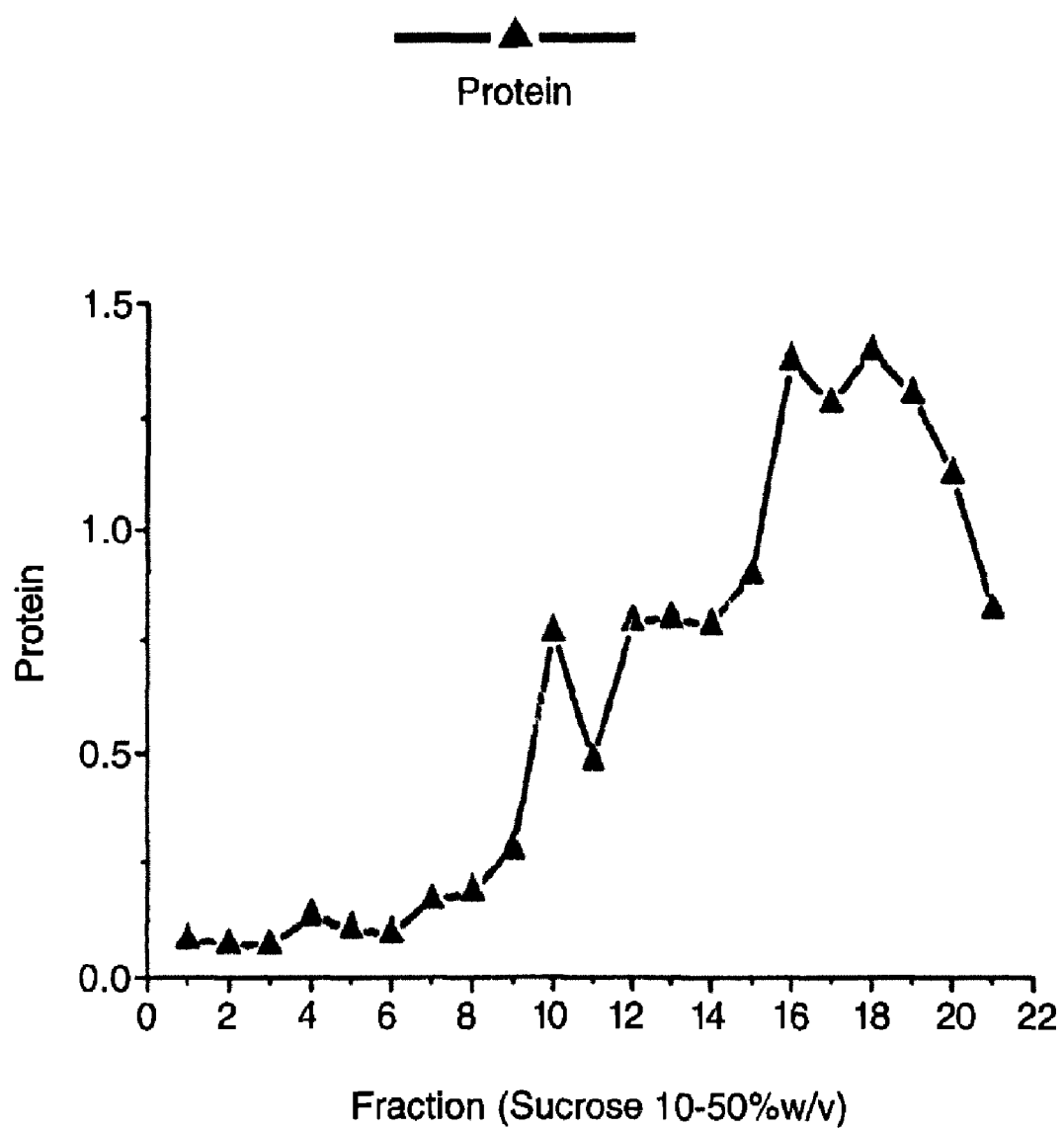

The E6E7 protein alone was found in fractions 10-22 by EIA (FIG. 6G). When mixed with standard DPPC ISCOMATRIX™ most of the E6E7 found in fractions 14-20 with little association detected (FIG. 6A). When mixed with CDL, DPL and DPA ISCOMATRIX™ the E6E7 was found predominantly in fractions which coincided with the association and the ISCOMATRIX™ peaks which indicated that almost complete association occurred (FIGS. 6B,C, E). When mixed with MPL and DPPG ISCOMATRIX™ the protein was found in fractions 9-14 coinciding with the association and ISCOMATRIX™ peaks indicating association but a significant amount found not associated in fractions 17-22 (FIGS. 6D,F).

These results indicate that a negatively charged protein binds poorly to standard DPPC ISCOMATRIX™ and the capacity to associate increases by using CDL, DPL, MPL, DPA or DPPG to varying degrees.

EXAMPLE 6

Immunisation of Mice with E6E7 Associated Standard and Modified ISCOMATRIX™

Three C57BL/6 mice were immunised, on day 0 and day 21, subcutaneously with 0.1 ml of E6E7 associated ISCOMATRIX™ containing 10 µg protein and 6 µg ISCOPREP™. After 7 days splenocytes were harvested and 20×10$^6$ cells restimulated in 8 mL in a T25 tissue culture flask with E7 transfected EL4 cells (C2) mytomycin-C treated and washed three times. Cells were cultured in RPMI media supplemented with 10% foetal calf serum, 2 mM glutamine, 5.5× 10$^{-5}$ Mβ-mercaptoethanol, 50 µg/ml gentamicin and incubated at 37° C. for 5 days in 5% $CO_2$. On day 6 the cultures were used as effectors in a standard 4 hour $^{51}$Cr release assays against C2 cells.

Figure 7:
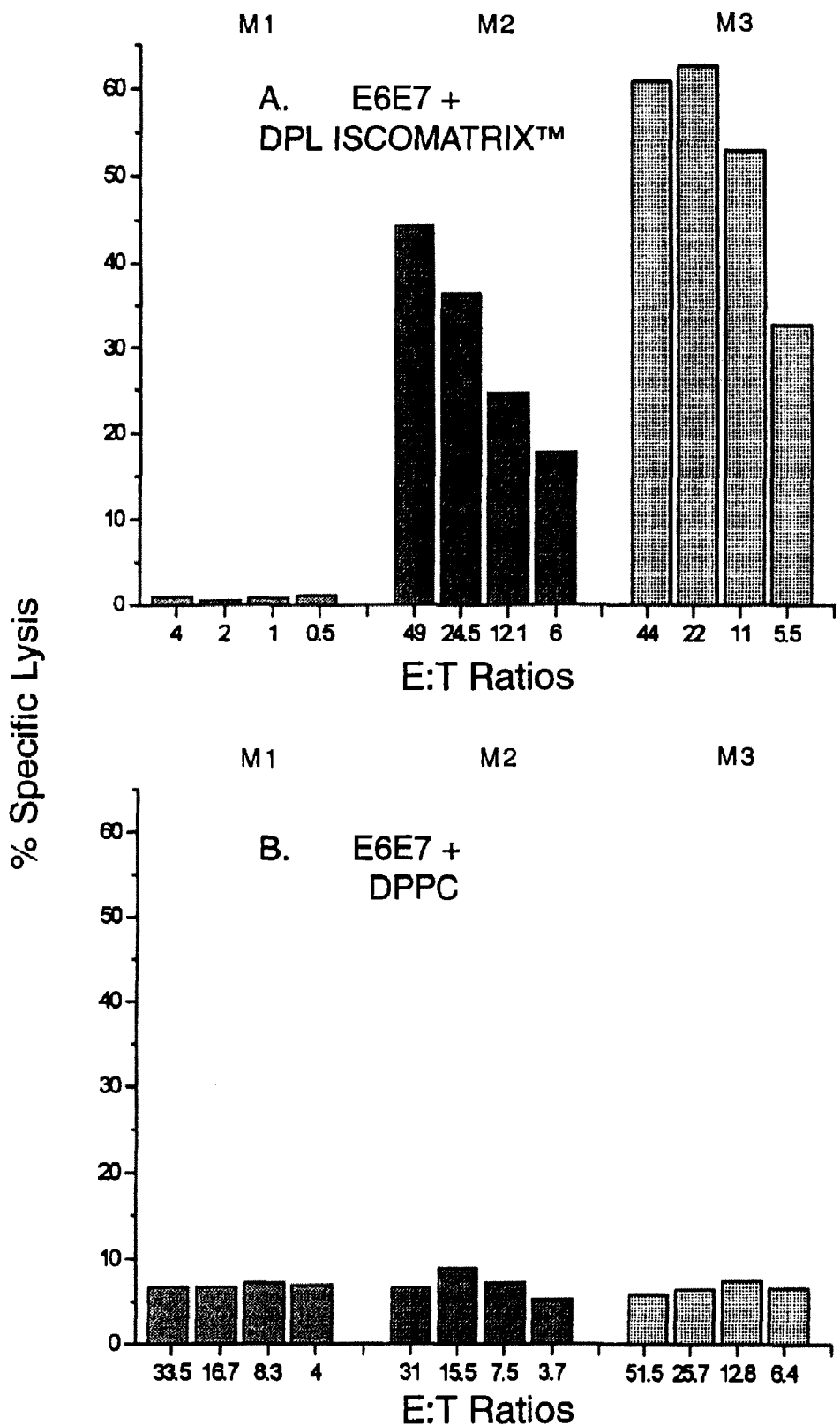
FIG. 7 is a graphical representation of CTL analysis in mice immunised with E6E7 DPL ISCOMATRIX™ (FIG. 7A) and E6E7 DPPC ISCOMATRIX™ (FIG. 7B). It can be seen that E6E7 DPL ISCOMATRIX™ induces CTL responses but E6E7 DPPC ISCOMATRIX™ does not.

The E6E7 associated DPL ISCOMATRIX™ induced a CTL response in 2 out of 3 mice (FIG. 7A). The E6E7 associated with standard DPPC ISCOMATRIX™ failed to induce a CTL response in any mice (FIG. 7B). The negative mouse in the DPL ISCOMATRIX™ group had insufficient cells for optimal readout and would not comply with criteria for a valid response. All other mice fulfilled criteria for valid responses.

These results show that the greater the association the better the CTL response.

EXAMPLE 7

Preparation of Antigen Associated ISCOMATRIX™ with a Naturally Negatively Charged Protein: *H. pylori* Family C Protein (HpC)

The HpC protein has a pi of 5.05 making it negatively charged at pH7.2. The protein was soluble in PBS pH7.2. The HpC associated ISCOMATRIX™ formulations were prepared by mixing at a 1:5 ratio of protein to ISCOPREP™ as ISCOMATRIX™ for 60 minutes at 20-25° C. The ISCOMATRIX™ formulations used were DPPC and DPL.

After formulation, preparations were purified on a sucrose gradient (10 to 50% sucrose w/v) and fractions analysed for HpC, association between HpC and ISCOMATRIX™ and ISCOMATRIX™ (FIG. 8). HpC was detected by adsorbing fractions diluted 1 in 10 in PBS to wells of an EIA plate then detecting with a HRP conjugated monoclonal antibody to HpC. Association was determined by EIA using a monoclonal antibody to HpC to capture and a HRP conjugated monoclonal antibody to ISCOPREP™ to detect ISCOMATRIX™ was determined by either detection of 3H cholesterol or DPH as described in example 1.

HpC alone was found in fractions 1-5 and when mixed with standard DPPC ISCOMATRIX™ the HpC was found predominantly in fractions 1-5 and not associated. When mixed with DPL ISCOMATRIX™ a significant proportion of the HpC was found in fractions 11-17 coinciding with the ISCOMATRIX™ and association peaks indicating association.

These results indicate that a negatively charged protein binds poorly to standard DPPC ISCOMATRIX™ and the capacity to associate increases by using DPL ISCOMATRIX™.

EXAMPLE 8

Preparation of Antigen Associated ISCOMATRIX™ with a Naturally Positively Charged Protein Utilising pH to Give a Positive Charge: E6E7

The E6E7 protein has a pI of 5.9 making it a negatively charged protein at pH7.2. It contains a hexa histidine sequence at the N terminus which will be positively charged at pH6. Solubility of the E6E7 was maintained using 8M urea, 50 mM Bis Tris, 0.15M NaCl pH6. The E6E7 associated ISCOMATRIX™ formulation was prepared by mixing equal mass of E6E7 with ISCOPREP™ as ISCOMATRIX™ for 60 minutes at 20-25° C., dialysing against 50 mM Bis Tris, 0.15M NaCl pH6 to remove the urea then centrifugation at 10,000 g for 5 mins to remove any precipitate.

Figure 9A:
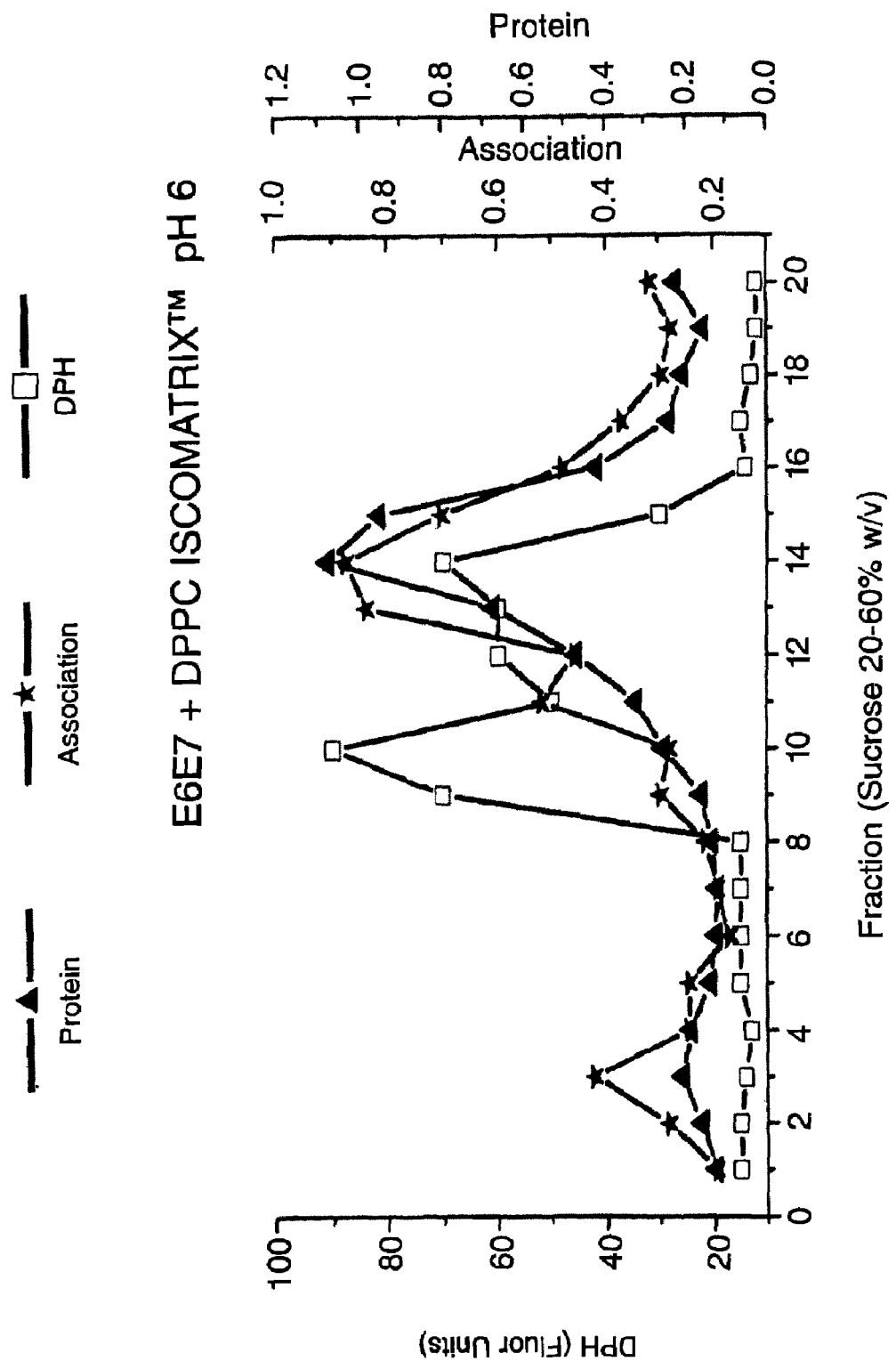
FIG. 9 is a graphical representation of the sucrose gradient analysis of two DPPC ISCOMATRIX™ formulations after mixing with E6E7 at pH6 (FIG. 6A) and pH7.2 (FIG. 6B). It can be seen that more E6E7 associates with DPPC ISCOMATRIX™ at pH6 than at pH7.2.
Figure 9B:
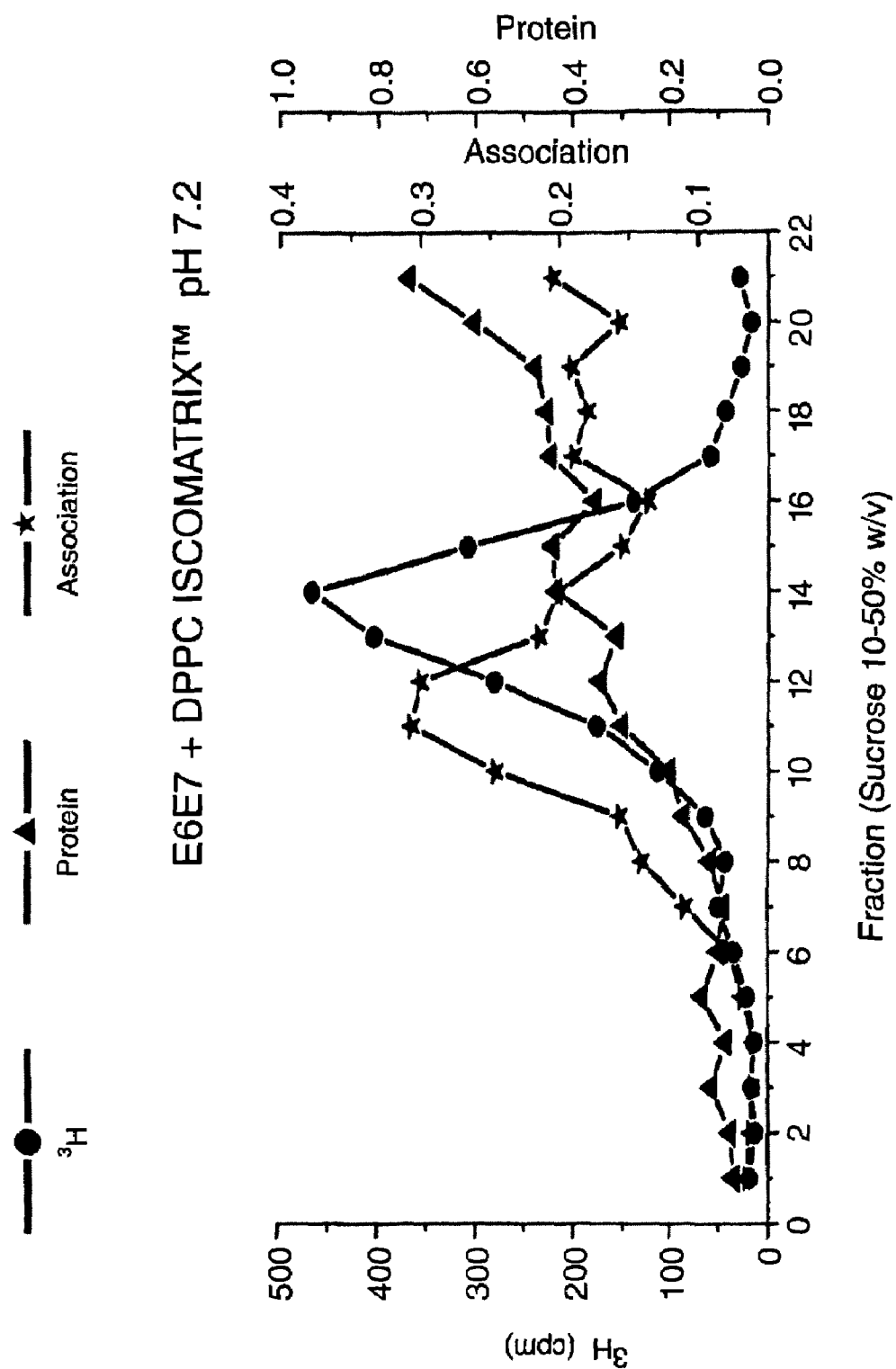
Figure 9C:
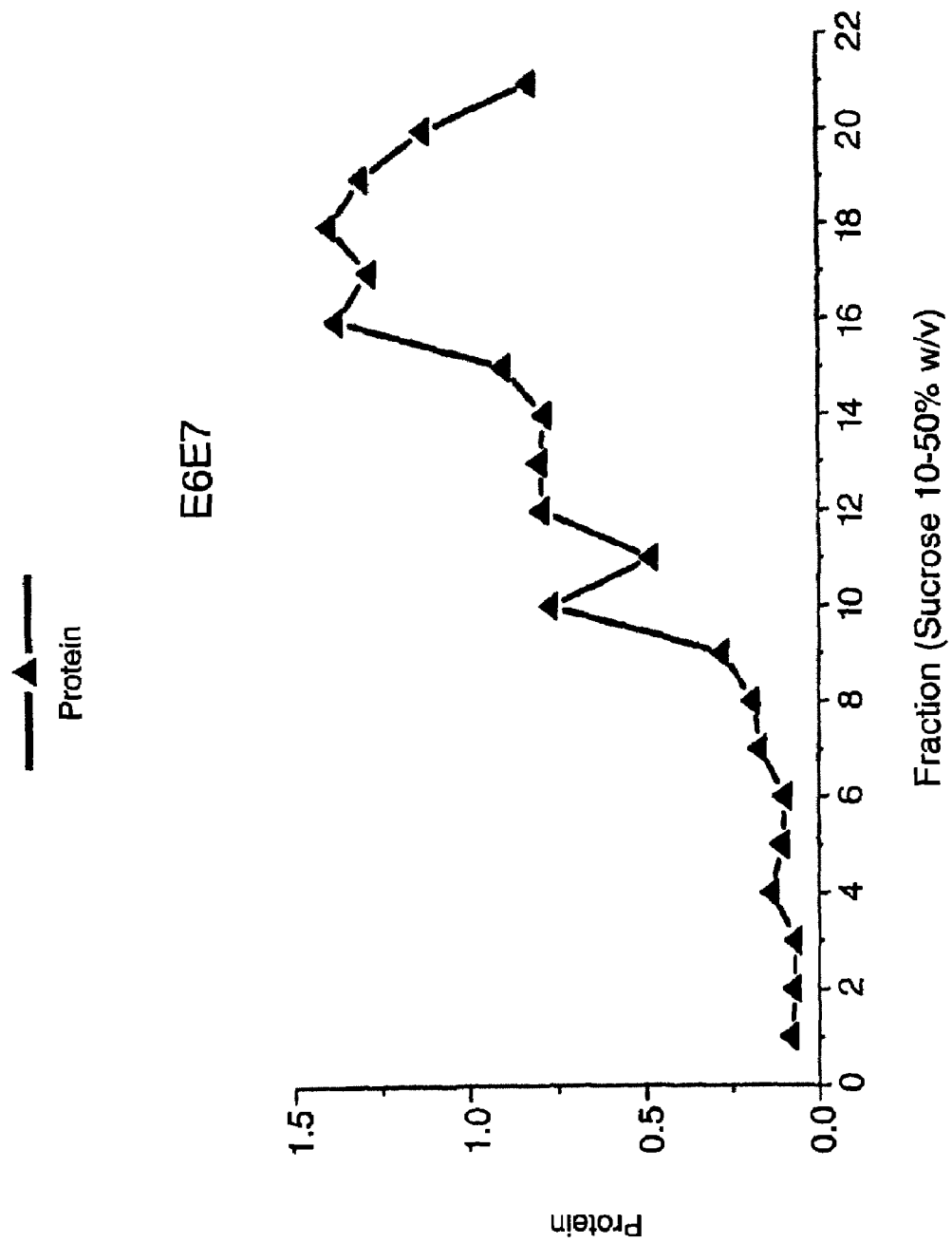

After formulation, preparations were purified on a sucrose gradient (50 to 10% sucrose w/v) and fractions analysed for protein, association between E6E7 and ISCOMATRIX™ and ISCOMATRIX™ (FIG. 9). Protein was detected using a sandwich EIA for E7. Association was determined by EIA using a monoclonal antibody to E7 to capture and a HRP conjugated monoclonal antibody to ISCOPREP™ to detect. ISCOMATRIX™ was determined by detection of 3H cholesterol or DPH as described in example 1. E6E7 was found in fractions 10-22 when run alone (FIG. 9C). When mixed with DPPC ISCOMATRIX™ at pH7.2 the E6E7 was predominantly found in fractions 16-22 with little evidence of association (FIG. 9B). When mixed with standard DPPC ISCOMATRIX™ at pH6 the E6E7 was predominantly found in fractions 12-16 coinciding with the ISCOMATRIX™ and association peaks which indicates association(FIG. 9A).

These results show that pH can be used to increase the capacity of standard DPPC ISCOMATRIX™ to associate with naturally negatively charged proteins.

EXAMPLE 9

Immunisation of Mice with pH Modified E6E7 Associated DPPC ISCOMATRIX™

Six C57BL/6 mice were immunized, on days 0 and 21, subcutaneously in the scruff of the neck with 0.1 ml of E6E7 associated ISCOMATRIX™ containing 6 µg ISCOPREP™ and 6 µg E6E7.

Antibody Responses:

Mice were bled on day 26 and sera analysed for antibodies to E7 by indirect EIA. Purified GSTE7 was adsorbed to a microtitre plate in 0.1M Carbonate pH9.6 then the plate blocked with a 0.1% casein solution and dried. Dilutions of sera were incubated for 1 hour at 20-25° C. then the plates washed. HRP conjugated goat anti mouse IgG was added and plates incubated for 1 hour at 20-25° C. then washed. TMB substrate was added and incubated for 10 mins at 20-25° C. followed by addition of 0.5M $H_2SO_4$ to stop the reaction. Plates were read at OD430 nm and end point titres calculated.

The E6E7 associated ISCOMATRIX™ group had a GMT of 949. Typically E6E7 with $Al(OH)_3$ gives GMT of approximately 100.

Cytokine Responses:

On day 27 splenocytes from each of 3 mice were harvested and pooled and $2.5\times10^6$ cells restimulated in 48-well plates with GSTE7 at 1 and 5 μg with ConA and RPMI as controls. Cells were cultured in RPMI media supplemented with 10% foetal calf serum, 2 mM glutamine. $5\times10^{-5}$ Mβ-mercaptoethanol. 100 μg/ml streptomycin and 100IU/ml pencillin and incubated at 37° C. for 2 days in 5% $CO_2$. The supernatant was harvested and γIFN and IL5 detected by EL using reagents from Endogen.

The E6E7 associated ISCOMATRIX™ induced up to 7.4 ng/ml γIFN and 140 pg/ml IL5 (Table 2). Typically E6E7 with $Al(OH)_3$ induces no detectable γIFN (<30 pg/ml) or IL5 (<4 pg/ml).

These results show that pH modified E6E7 associated ISCOMATRIX™ were immunogenic in mice and induced a Th1 type response.

EXAMPLE 10

Preparation of Chelating (CHL) ISCOMATRIX™

CHL ISCOMATRIX™ was prepared by the method of Macfarlan and Malliaros. (1998) International Patent Publication No. WO 98/36772). Briefly, to 1.6 ml 50 mM Tris, 150 mM NaCl, 0.6 mM $CuCl_2$ pH 7.2 (Buffer A) was added 0.2 ml of a solution containing 10 mg/ml cholesterol, 9 mg/ml DPPC. 1.074 mg/ml dipalmitoyl-rac-glycerol-3(8-(3,6-dioxy) octyl-1-amino-N,N-diacetic acid) (DPIDA) in 20% MEGA-10 detergent (w/v) then 0.2 ml of a solution containing 50 mg/ml ISCOPREP™ 703 in Buffer A. The solution was held at 25° C. for 90 mins with gentle mixing. Dialysis was then performed firstly against Buffer A overnight with 2 changes of buffer then against 50 mMTris, 50 mM $NaHaPO_4.2H_2O$, 150 mM NaCl pH6.9 for 2 days with two changes of buffer. During dialysis CHL ISCOMATRIX™ containing cholesterol. DPPC, DPIDA and ISCOPREP™ was formed. The CHL ISCOMATRIX™ formulation was of typical appearance by electron microscopy.

EXAMPLE 11

Generation, Expression and Purification of Hexahistidine (6H) ±Hexalysine (6K) HpC The HpC protein has a pi of 5.05 making it negatively charged at pH7.2. Addition of 6K would change the pi to 7.68 and give a positively charged tail. Two clones were constructed to give HpC plus 6H, for purification, and with and without 6K. CSL 694 DNA (HpC13 with a C-terminal 6H in the vector pGexStop as described in Edwards et al. 1998) was used as the template for PCR amplification to generate a C-terminal 6K. The PCR product was cloned into the EcoRI-BglII sites of the expression vector pGexStopIV, creating tandem C-terminal 6K followed by 6H tags. This was generated in the *E. coli* strain ER1793 and designated CSL 1424.

One litre cultures were induced at $A_{600}=2$ with 0.5 mM BPTG and harvested 5 hours post induction. Soluble recombinant protein was purified utilising the C-terminal 6H tag for metal (nickel) affinity chromatography. Eluted protein was dialysed against PBS.

EXAMPLE 12

Preparation of Antigen Associated ISCOMATRIX™ With 6H and 6K Tags:HpC

The HpC protein with 6H has a pI of 5.85 making it negatively charged at pH7.2. Addition of a 6K to this protein gives a pI of 7.68 making it positively charged at pH7.2. Both forms of the protein were soluble in PBS pH7.2. The HpC associated ISCOMATRIX™ formulations were prepared by mixing at a 1:5 ratio of protein to ISCOPREP™ as ISCOMATRIX™ for 60 minutes at 20-25° C. The ISCOMATRIX™ formulations used were DPPC and CHL. CHL ISCOMATRIX™ technology was used as a standard method for associating 6H proteins with ISCOMATRIX™.

After formulation, preparations were purified on a sucrose gradient (10 to 50% sucrose w/v) and fractions analysed for HpC, association between HpC and ISCOMATRIX™ and ISCOMATRIX™ (FIG. 10). HpC was detected by adsorbing fractions diluted 1 in 10 in PBS to wells of an EIA plate then detecting with a HRP conjugated monoclonal antibody to HpC. Association was determined by EIA using a monoclonal antibody to HpC to capture and a HRP conjugated monoclonal antibody to ISCOPREP™ to detect. ISCOMATRIX™ was determined by detection of DPH as described in example 1.

Figure 10A:
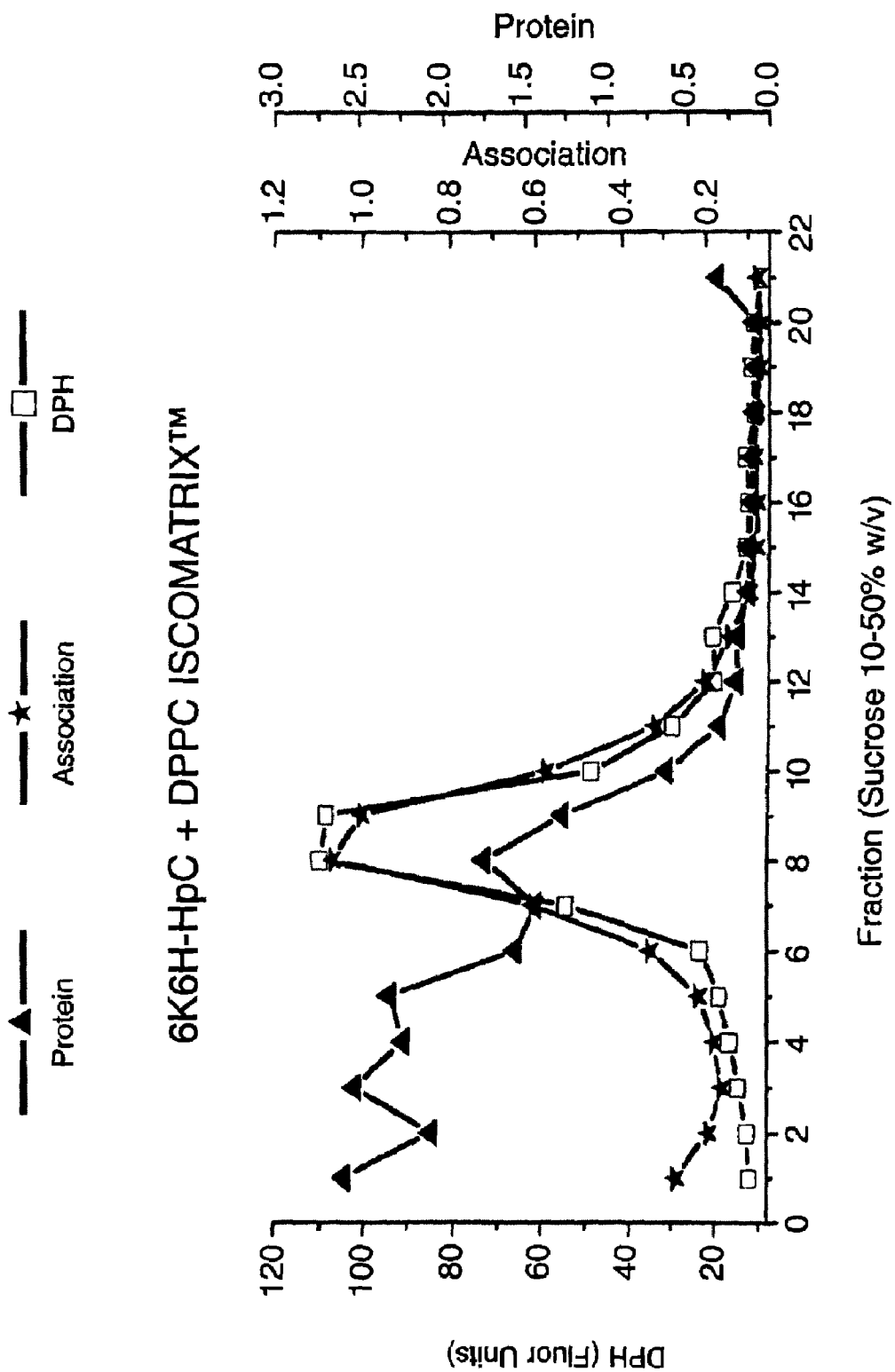
FIG. 10 is a graphical representation of the sucrose gradient analysis of ISCOMATRIX™ formulations after mixing with modified HpC from Example 11. It can be seen that addition of 6K to HpC increases the association with DPPC ISCOMATRIX™ to a level comparable to that with the 6H and CHL ISCOMATRIX™ formulation.
Figure 10B:
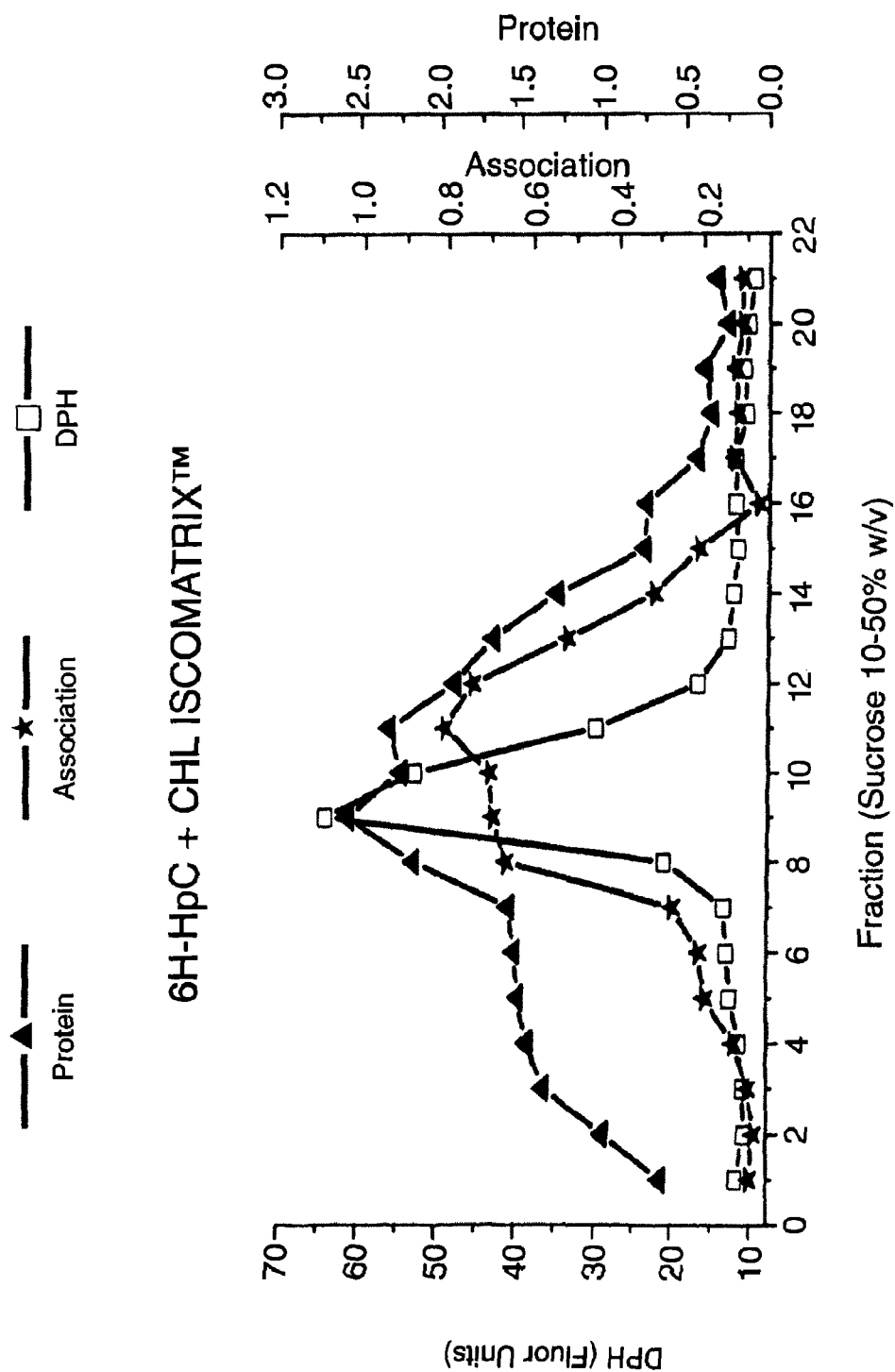
Figure 10C:
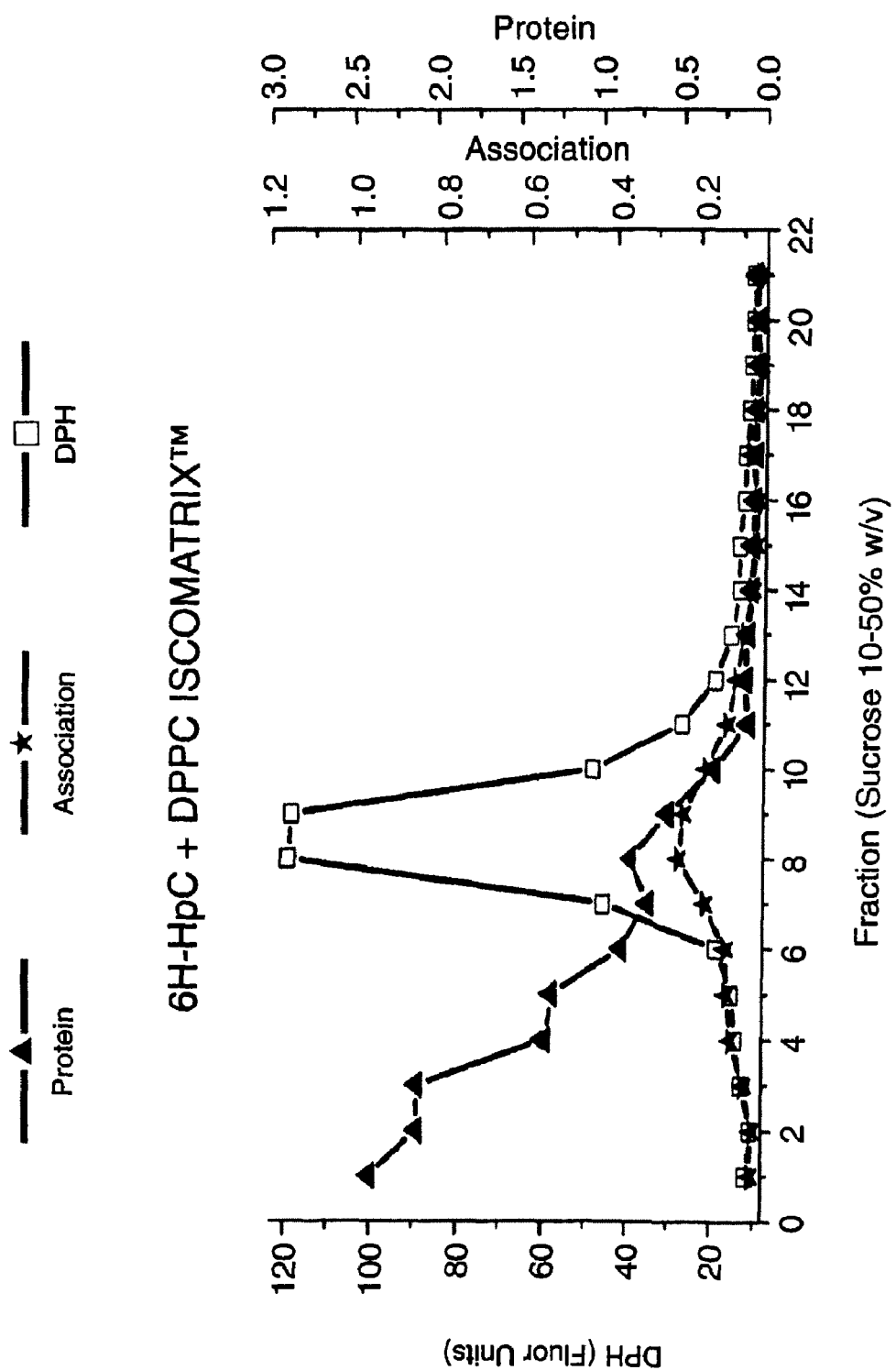

When mixed with standard DPPC ISCOMATRIX™ the 6H-HpC was found in fractions 1-6 and with little evidence of association (FIG. 10C). When 6K6H-HpC was mixed with DPPC ISCOMATRIX™ a significant amount of HpC was in fractions 7-11 coinciding with the association and ISCOMATRIX™ peaks indicating association (FIG. 10A). When 6H-HpC was mixed with CHL ISCOMATRIX™ most of the HpC was in fractions 7-14 coinciding with the ISCOMATRIX™ and association peaks indicating association (FIG. 10B).

These results show that addition of a 6K to a negatively charged protein increased its capacity to associate with standard DPPC ISCOMATRIX™ and the association achieved was comparable to that using 6H with CHL ISCOMATRIX™.

EXAMPLE 13

Preparation of Synthetic POLYTOPE ISCOM™ and Associated ISCOMATRIX™ with Palmitic Acid (PAL), 6H, 6K and No Formulation Tags The polytopes were synthesised and purifed by Chiron Technologies on Multipin (TM) crowns, as described by Valerio et al., using the Fmoc alpha-amino protection scheme for the amino acids. After sidechain deprotection and cleavage in a trifluoracetic acid/scavenger solution, peptides were precipitated with ether and dried. The redissolved peptide was purified by preparative reverse phase HPLC using elution with a gradient of acetonitrile. Fractions containing material of the correct molecular mass, as determined by ion spray mass spectrometry, were pooled and dried.

The polytope was as follows:
Tag-YPHFMPTNLRPQASGV YMTYORTRALVSYTPS AEK3-OH (<400>3) containing four known BALB/c restricted epitopes, YPHFMPTNL (<400>4), RPQAS- GVYM (<400>5), TYQRTRALV (<400>6) and SYIP-SAEKI (<400>7). The tags used were PAL, 6H, 6K or H (No tag).

For the PAL polytope association was achieved by incorporation into ISCOM™ (Immunostimulating complex) according to the method of Morein et al. (1989). Briefly, to 4 mg of polytope solubilised in 1.76 ml 10% MEGA-10 detergent (w/v), 50% Acetonitrile in PBS was added 0.16 ml of a solution containing 10 mg/ml cholesterol and 10 mg/ml DPPC in 20% MEGA-10 detergent (w/v) then 0.08 ml of a solution containing 100 mg/ml ISCOPREP™ 703 in PBS. The solution was held at 25° C. for 1 hour with gentle mixing. During subsequent dialysis against PBS/azide ISCOMs™ containing palmityfied polytope, cholesterol, DPPC and ISCOPREP™ were formed. These ISCOMs™ were of typical appearance by electron microscopy.

The 6H polytope was solubilised in 8M urea then mixed with CHL ISCOMATRIX™ and the 6K and no tag polytopes were solubilised in PBS then mixed with standard DPPC ISCOMATRIX™. All formulations were prepared at a ratio of 1:8 protein to ISCOPREP™ as ISCOMATRIX™ and incubated for 60 mins at 20-25° C.

The preparations were purified on a sucrose gradient (10 to 50% sucrose w/v) and fractions analysed for protein and ISCOMATRIX™. Protein was detected using CBQCA (<400>8) from Molecular Probes according to the manufacturers instructions or by Coomassie according to the method of Bradford (1976). Briefly 100 µl of each fraction was added to a microplate followed by addition of 100 µl Coomassie reagent then the plate read at 595 nm. ISCOMATRIX™ was detected by DPH as described in example 1.

Figure 11A:
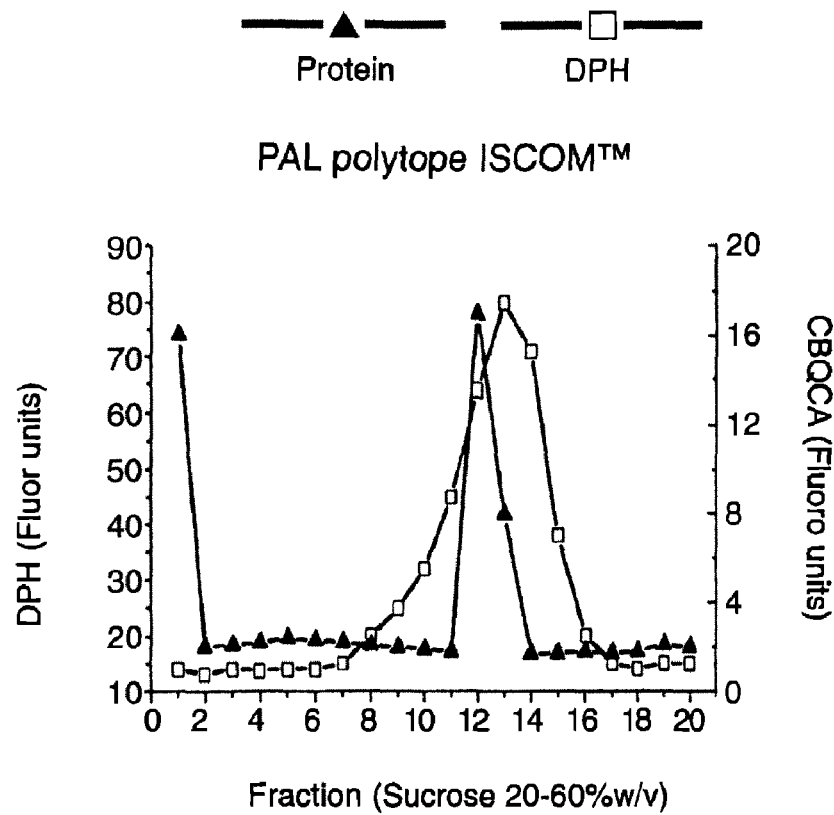
FIG. 11 is a graphical representation of the sucrose gradient analysis of four polytope ISCOM™ and ISCOMATRIX™ formulations from Example 13. It can be seen that mere is some association of the 6K polytope with ISCOMATRIX™ but there is no association if the 6K are not present. The 6K polytope association with ISCOMATRIX™ was comparable to hydrophobic incorporation of the PAL polytope into ISCOMs™ but less than association between 6H polytope and CHL ISCOMATRIX™.
Figure 11B:
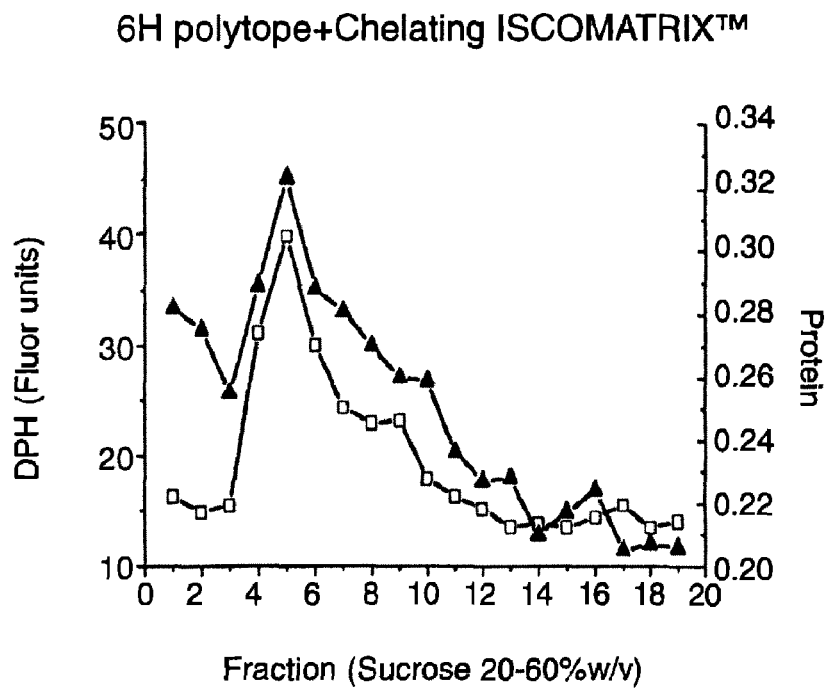
Figure 11C:
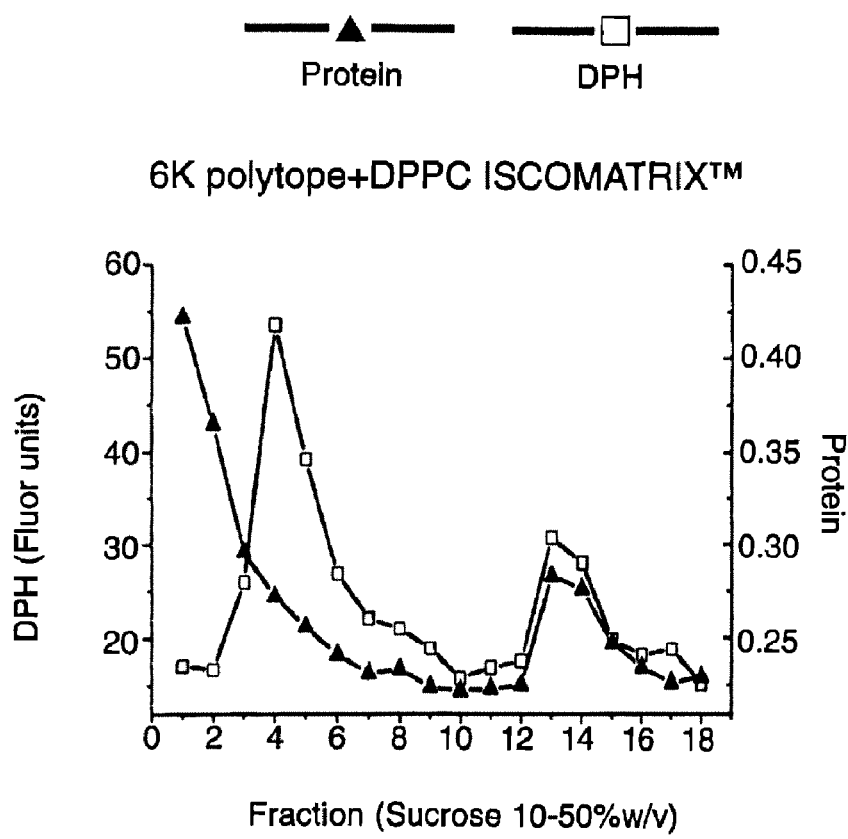
Figure 11D:
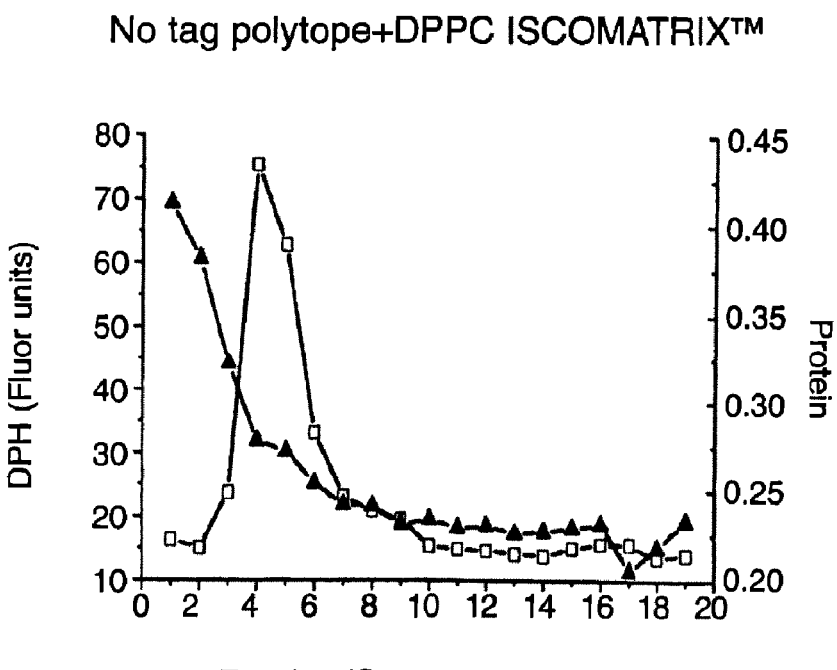
Figure 11E:
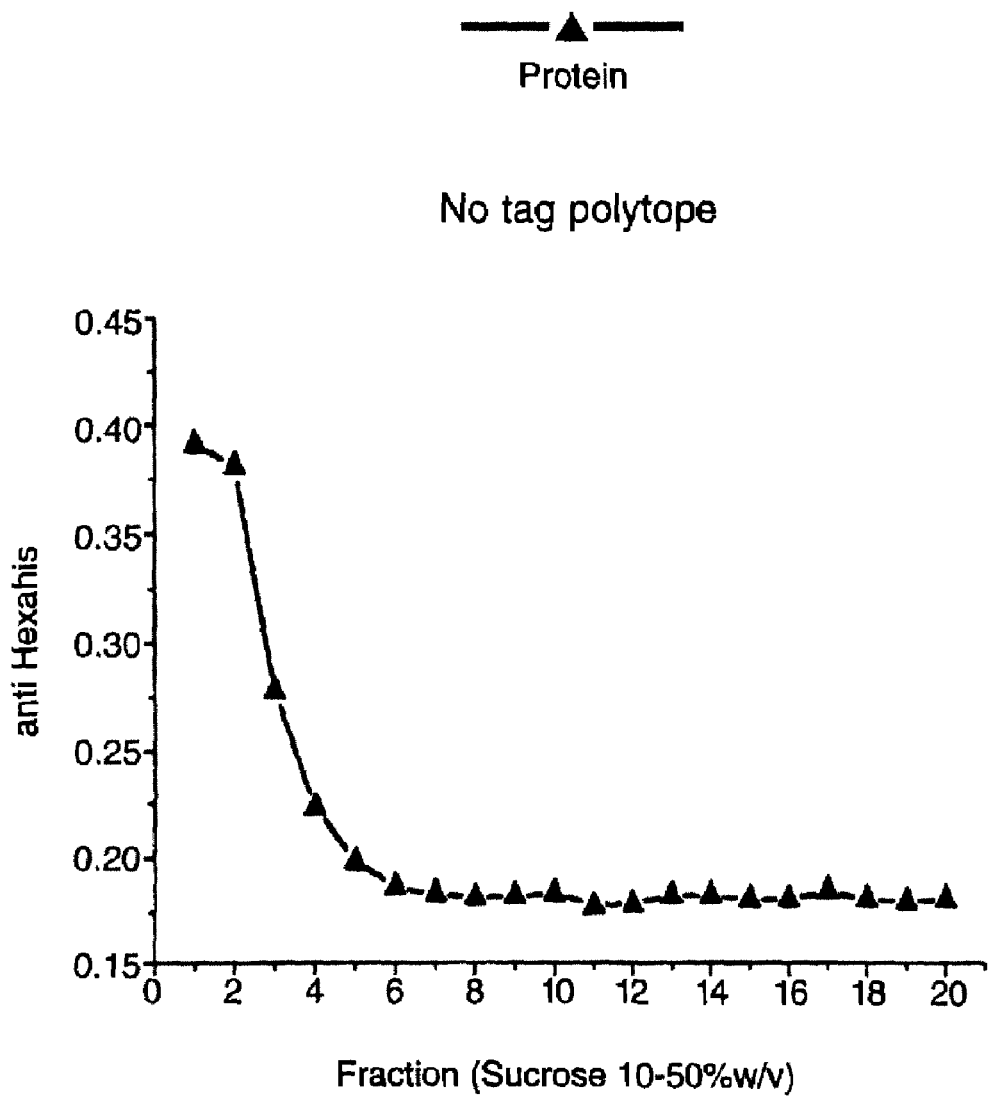

The polytope alone was found in fractions 1-5 (FIG. 11E). The protein, as detected by CBQCA (<400> 8), in the PAL polytope ISCOM™ was found predominantly in fractions 11-13 coinciding with the ISCOMATRIX™ peak indicating incorporation (FIG. 11A). The protein, as detected by Coomassie, in the 6K polytope associated ISCOMATRIX™ was found predominantly in fractions 1-5 and was probably not associated with ISCOMATRIX™ (FIG. 11C). A significant proportion of polytope was found in fractions 12-14 coinciding with the ISCOMATRIX™ peak indicating association. The protein, as detected by Coomassie, in the 6H polytope associated CHL ISCOMATRIX™ was found predominantly in fractions 4-10 coinciding with the ISCOMATRIX™ peak indicating association (FIG. 11B). There was a significant proportion of 6H polytope found in fractions 1-3 which was probably not associated. The protein, as detected by Coomassie, in the no tag associated ISCOMATRIX™ was almost all found in fractions 1-5 and probably not associated with ISCOMATRIX™.

These results show that a tag was required for association of the polytope tested with ISCOMATRIX™ and that 6 K polytope association with standard DPPC ISCOMATRIX™ was comparable to incorporation of hydrophobic PAL polytope into ISCOMs™ but not as good as 6H polytope association with CHL ISCOMATRIX™.

EXAMPLE 14

Immunisation of Mice with Synthetic Polytope ISCOM™ and Associated ISCOMATRIX™ Formulations Three BALB/c mice were immunized subcutaneously at the base of the tail with 0.1 ml of polytope ISCOM™ or associated ISCOMATRIX™ containing 6 µg ISCOPREP™ and between 3.5 µg and 5 µg protien.

CTL assays were performed according to the method of Elliott et al. (1999). Briefly, splenocytes from each spleen were removed on day 14 and cultured in 1 ml medium at $5\times10^6$ cell/ml, in a 24 well plate, together with 1 µg/ml of the individual peptides (4 peptides/spleen) in a humidifed incubator at 37° C. On day 3, 1 ml of fresh media was added and then further in vitro restimulation performed on day 7 by adding irradiated (800 rad) peptide sensitised (10 µg/ml, 1 hr 37° C., 2 washes) P815 cells at a responder to stimulator ratio of 20:1 to $2\times10^6$ effectors/well. The procedure was repeated twice more at 7 day intervals and the bulk cultures were used as effectors 6 days later in a standard 6 hr chromium release assay. Medium contained RPMI 1640 supplemented with 10% FCS (QIMR), $5\times10^{-5}$ M 2-mercaptoethanol, 2 mM glutamine and pen/strep antibiotics. Target cells were $^{51}$Cr labelled peptide sensitised and unsensitised (control) P815 cells. The ratio of effector:target was 50, 10 and 2 to 1. The assays were performed in 96 well round bottom plates in duplicate.

Figure 12A:
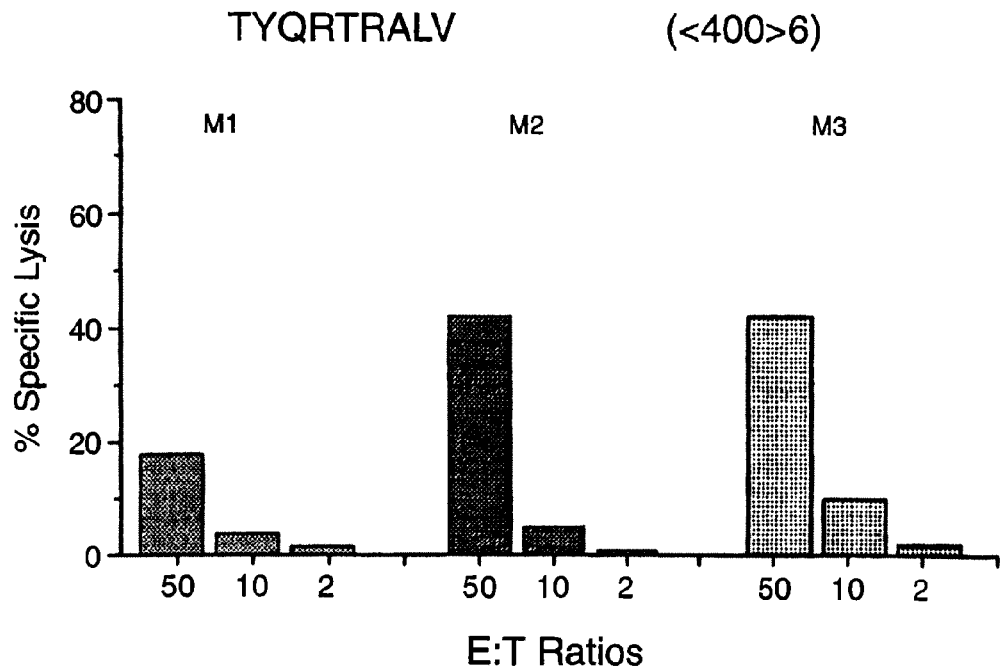
FIG. 12 is a graphical representation of the CTL analysis of four synthetic polytope ISCOMATRIX™ formulations from Example 13. It can be seen that 6K polytope ISCOMATRIX™ induced CTL responses against all 4 epitopes in the polytope (FIG. 12C) but the polytope ISCOMATRIX™ formulation without a tag only induced a low CTL response to one of the epitopes (FIG. 12D). The CTL responses for the 6K polytope ISCOMATRIX™ were comparable to those induced with the PAL polytope ISCOM™ (FIG. 12A) and the 6H polytope CHL ISCOMATRIX™ (FIG. 12B).
Figure 12A:
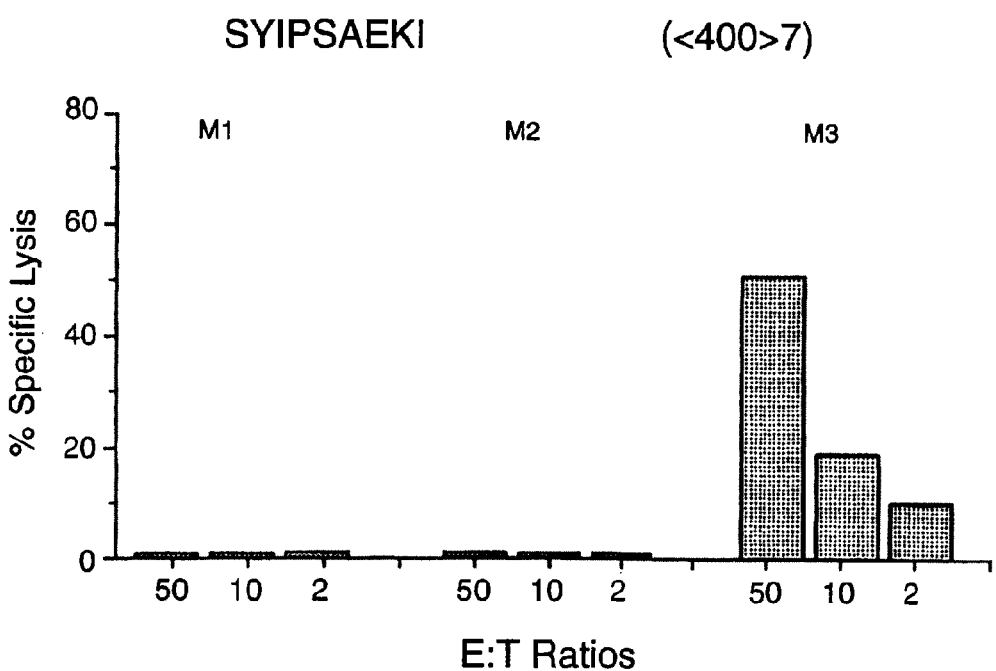
Figure 12B:
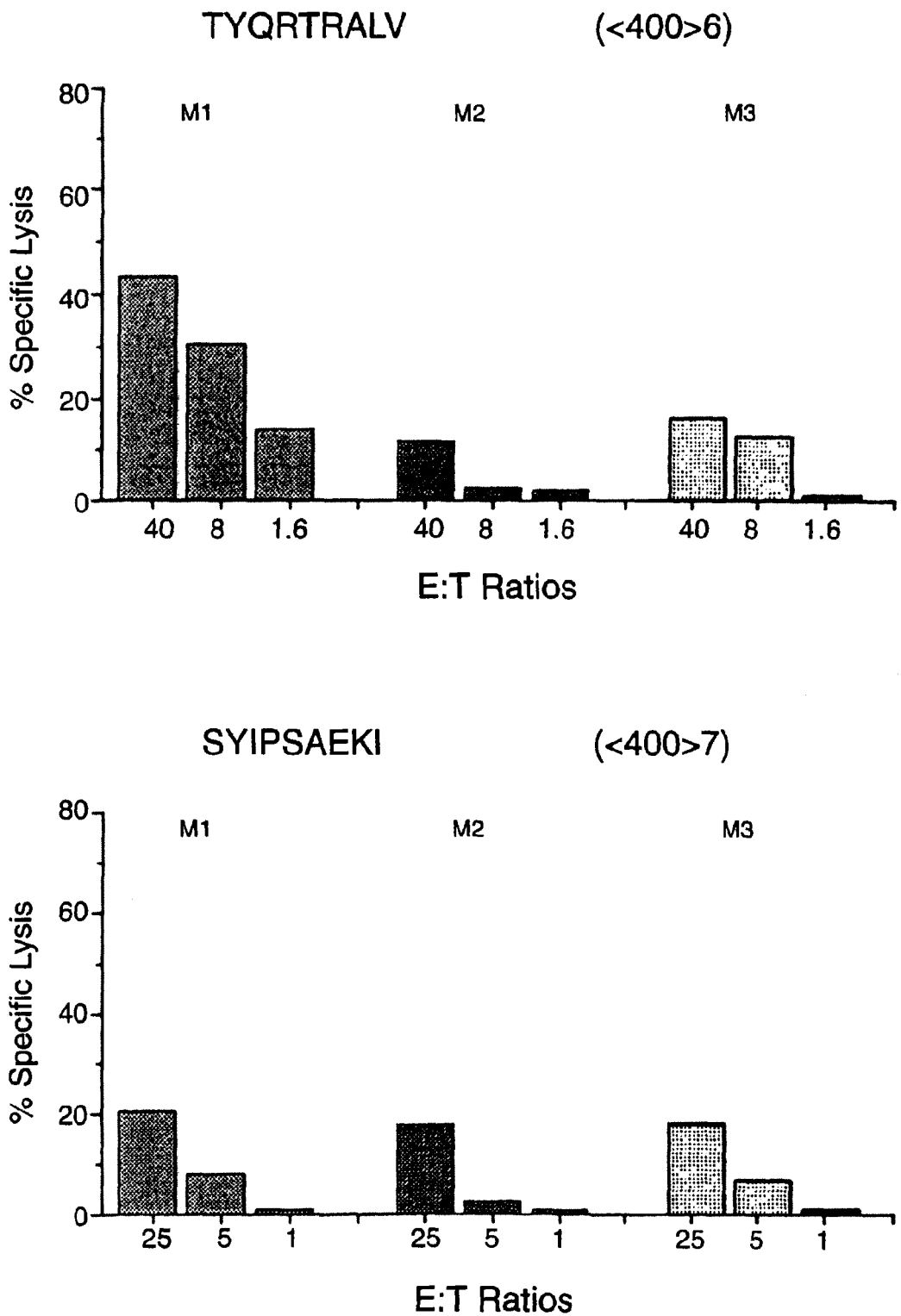
Figure 12C:
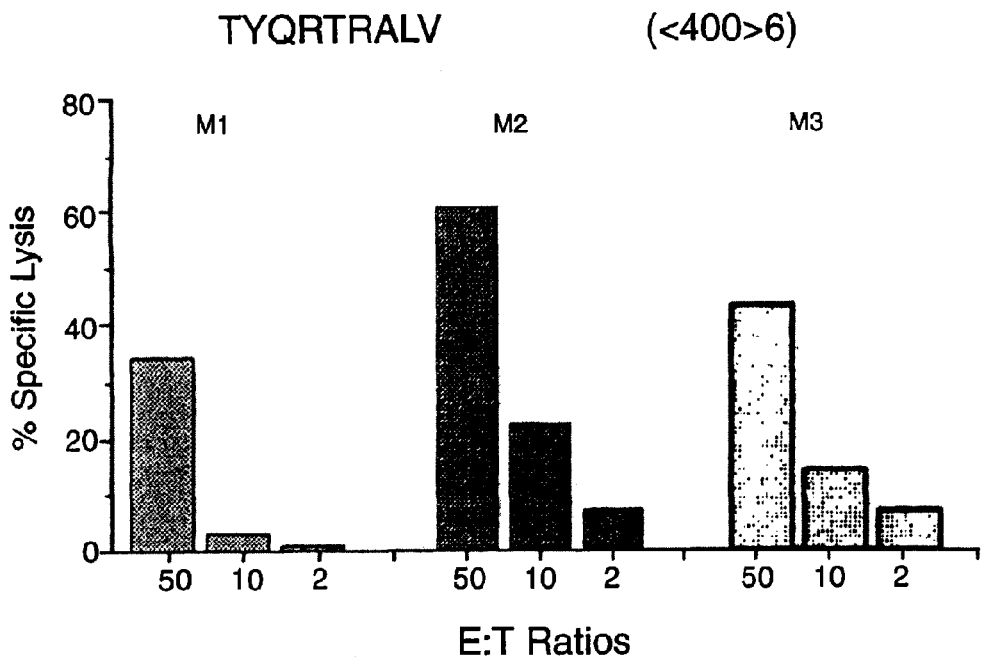
Figure 12C:
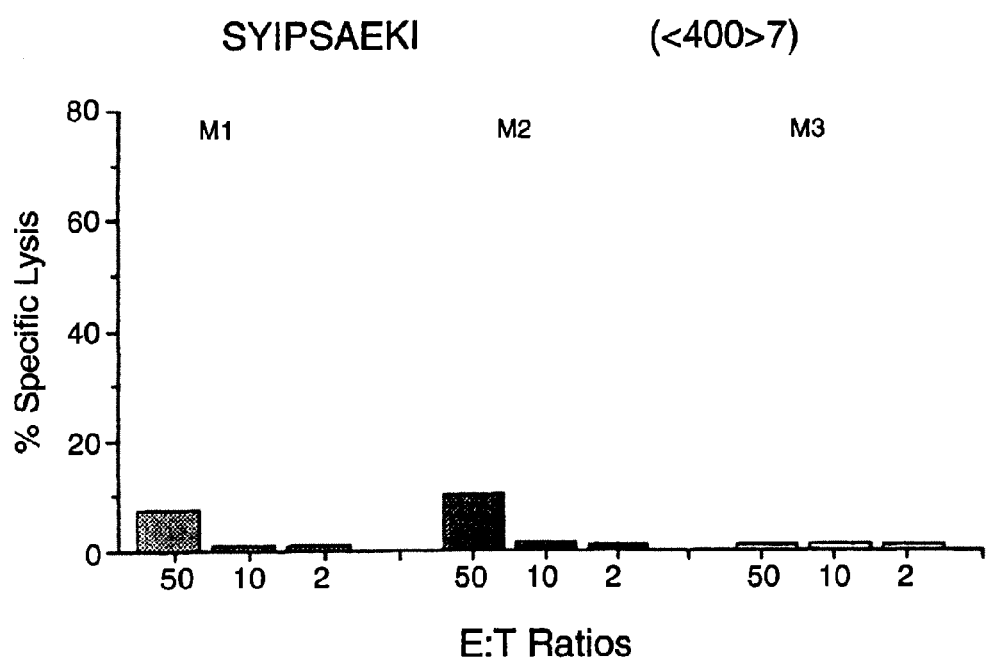
Figure 12D:
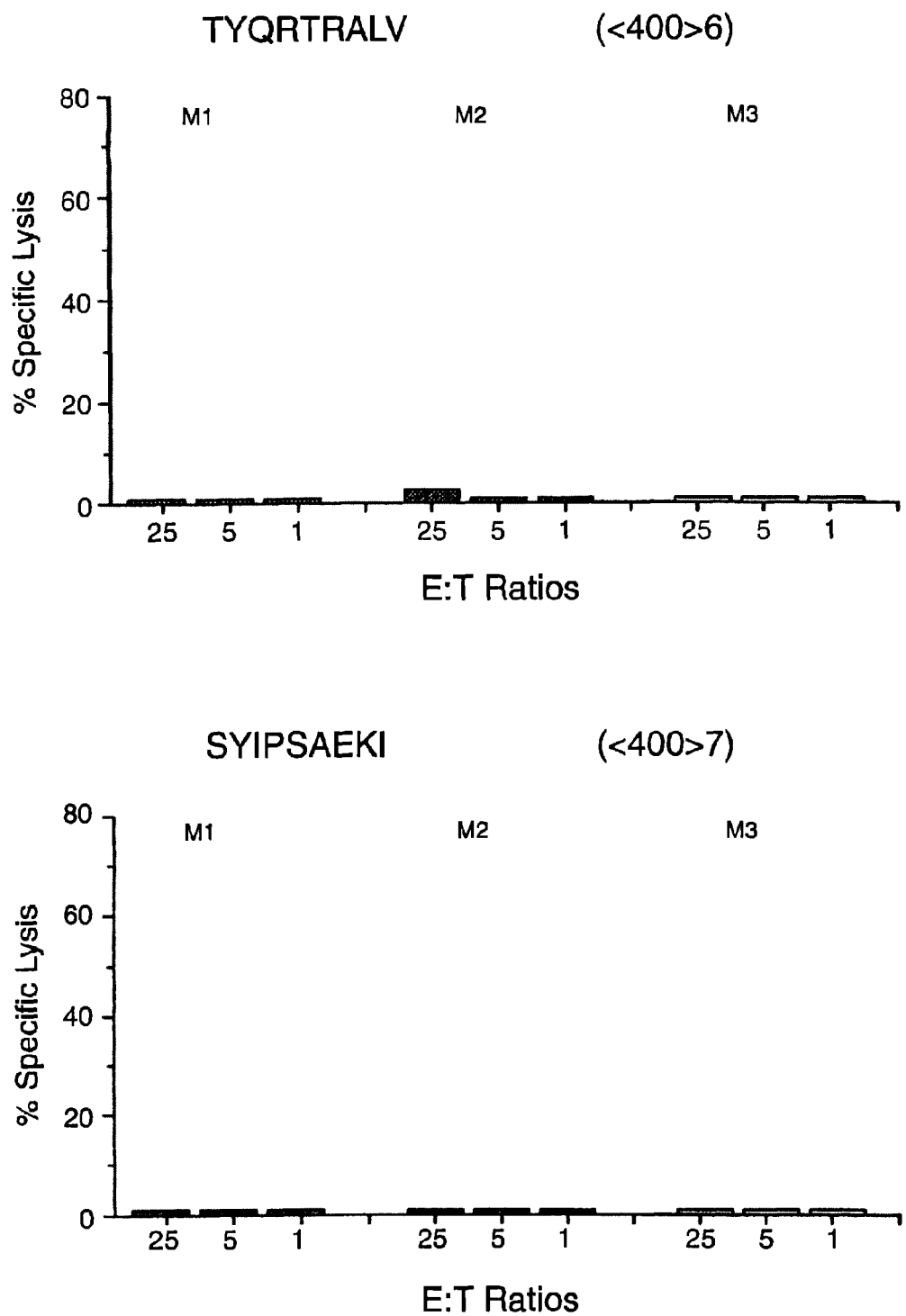

The PAL polytope ISCOM™ induced CTL responses against all 4 epitopes with 3/3 mice for TYQ, 1/3 for SYI, 2/3 for YPH and 2/3 for RPQ (FIG. 12A). The 6H polytope associated CHL ISCOMATRIX™ induced CTL responses against 3/3 mice for all 4 epitopes (FIG. 12B). The 6K polytope associated DPPC ISCOMATRIX™ induced CTL responses against all 4 epitopes with 3/3 for TYQ, YPH and RPQ and 2/3 for SYI (FIG. 12C). The no tag polytope associated DPPC ISCOMATRIX™ induced a weak CTL response in 2/3 mice for RPQ but there was no CTL response detected to any of the other epitopes (FIG. 12D). The SYI sequence is known to be a weak epitope and this was the case for all formulations.

These results show that association of polytope with the ISCOM™ or ISCOMATRIX™ was required for optimal CTL induction and that association using 6K was as effective as 6H with CHL ISCOMATRIX™ or classical incorporation of hydrophobic proteins (PAL polytope ISCOM™).

EXAMPLE 15

Generation, Expression and Purification of Recombinant (r) 6H ±6K Polytope

Pstmpdv DNA(supplied by QIMR) was used as the template for PCR amplification of the murine polytope, YPH-FMPTNLTSSGPSNTPPEIFAPGNYPAL-SYIPSAEKIEEGAIVGEI RPQASGVYM (<400>9), to enable generation with and without a C-terminal 6K (CSL 1430 and 1426 respectively). PCR products were cloned into the BamHI-XhoI sites of the expression vector pET24b (Novagen) generating an N-terminal T7-tag (for identification) and tandem C-terminal 6K followed by 6H (for purification).

Clones were generated in the *E. coli* strain ER1793 and subsequently transformed into the expression strain BL21 (DE3). One litre cultures were induced at $A_{600}$=2 with 0.5 mM IPTG and harvested 4 hours post induction. Soluble recombinant protein was purified utilising the C-terminal 6H tag for metal (nickel) affinity chromatography. Eluted protein was dialysed against PBS.

EXAMPLE 16

Preparation of rPolytope Associated ISCOMATRIX™ 6H and 6K

The murine polytope with 6H has a pI of 5.85 making it negatively charged at pH7.2. Addition of a 6K to this gives a pI of 7.68 making it positively charged at pH7.2. Both forms of the protein were soluble in PBS pH7.2. The polytope associated ISCOMATRIX™ formulations were prepared by mixing at a 1:5 ratio of protein to ISCOPREP™ as ISCOMATRIX™ for 60 minutes at 20-25° C. The ISCOMATRIX™ formulations used were DPPC, CDL, DPL and CHL. Formulation at pH4.3 to be below the pi of glutamic acid (E) was investigated as there were a number of E's in the sequence which could potentially interfere with association.

After formulation, preparations were purified on a sucrose gradient (10 to 50% sucrose w/v) and fractions analysed for protein and ISCOMATRIX™ (FIG. 13). Protein was detected by adsorbing fractions diluted 1 in 10 in PBS to wells of an EIA plate then detecting with a HRP conjugated monoclonal antibody to 6H. ISCOMATRIX™ was determined by of detection 3H cholesterol or DPH as described in example 1.

Figure 13A:
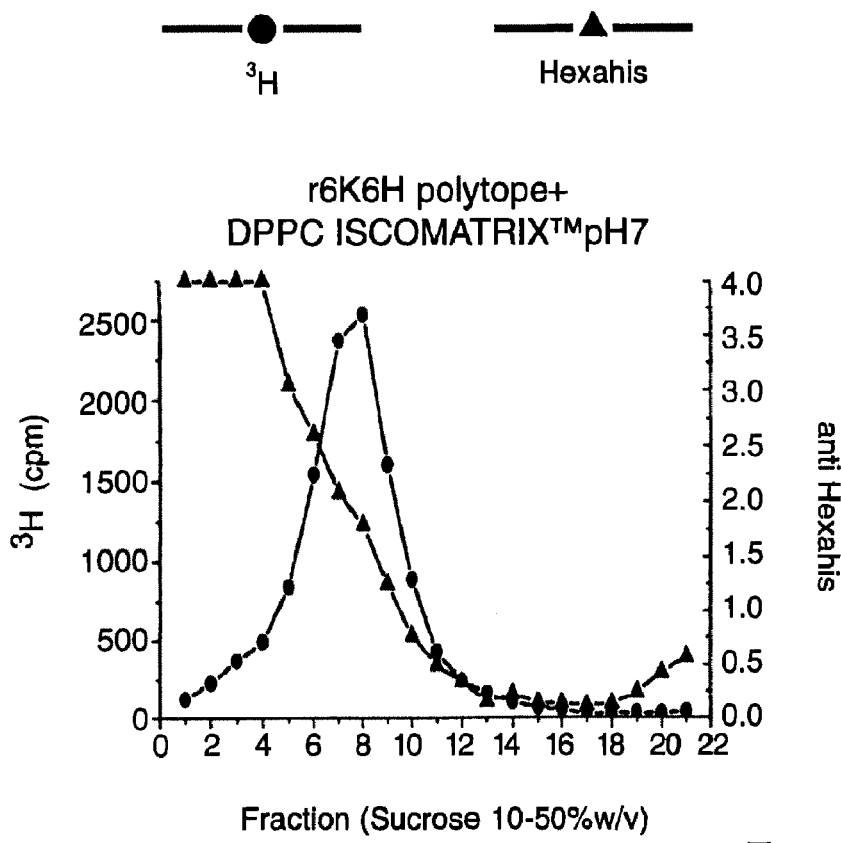
FIG. 13 is a graphical representation of the sucrose gradient analysis of ten recombinant ISCOMATRIX™ formulations from Example 16. It can be seen that the combination of adding a 6K tag with CDL or DPL ISCOMATRIX™ gives increased association over 6K with DPPC ISCOMATRIX™ and to then combine these with low pH increase the capacity to associate even further. The association achieved with the combination of 6K, CDL ISCOMATRIX™ and low pH gave almost complete association of the polytope with ISCOMATRIX™ and the association was greater than could be achieved with 6H polytope CHL ISCOMATRIX™.
Figure 13B:
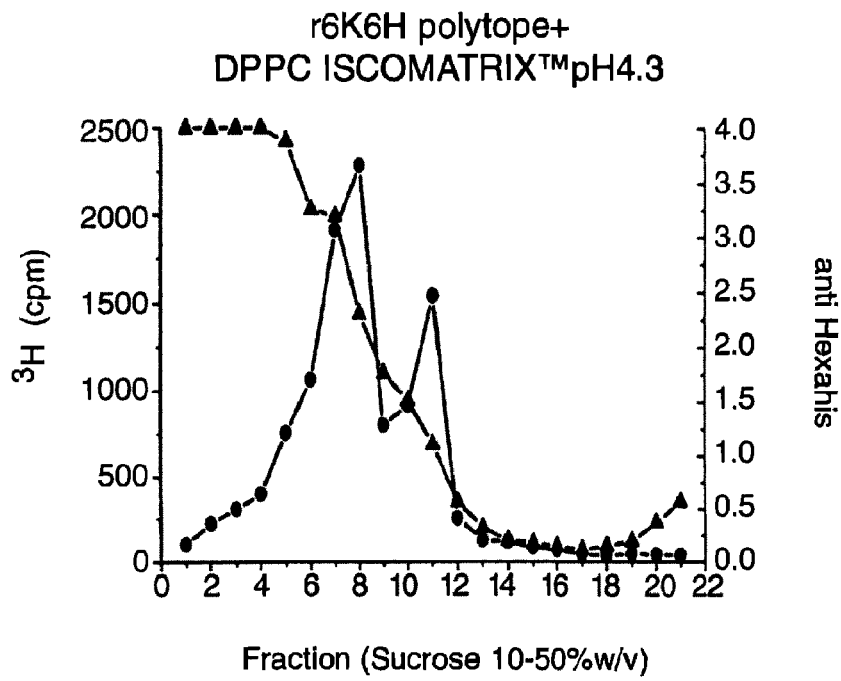
Figure 13C:
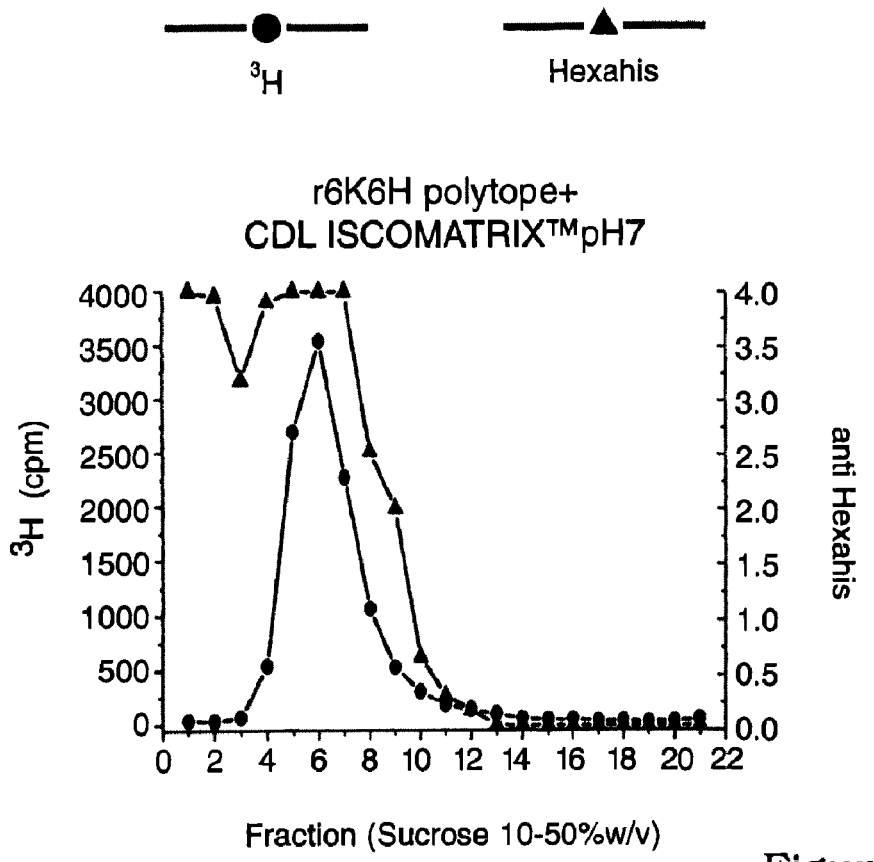
Figure 13D:
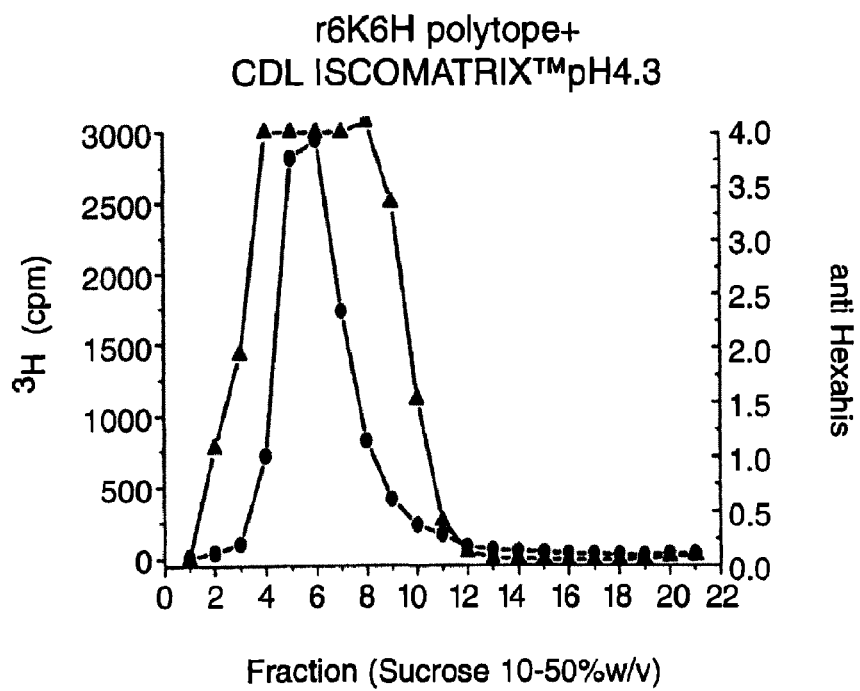
Figure 13E:
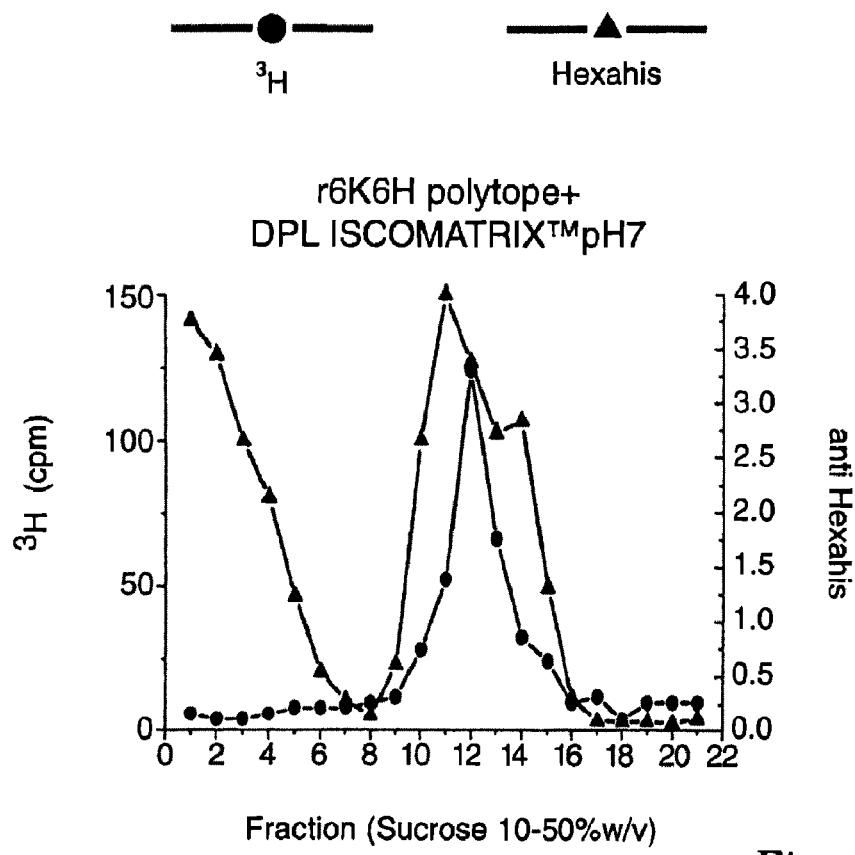
Figure 13F:
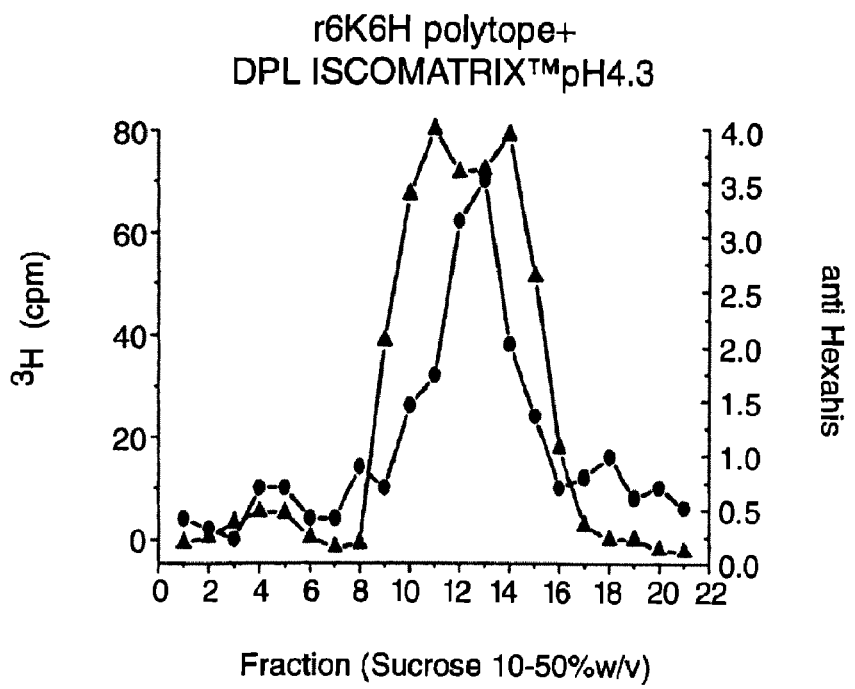
Figure 13G:
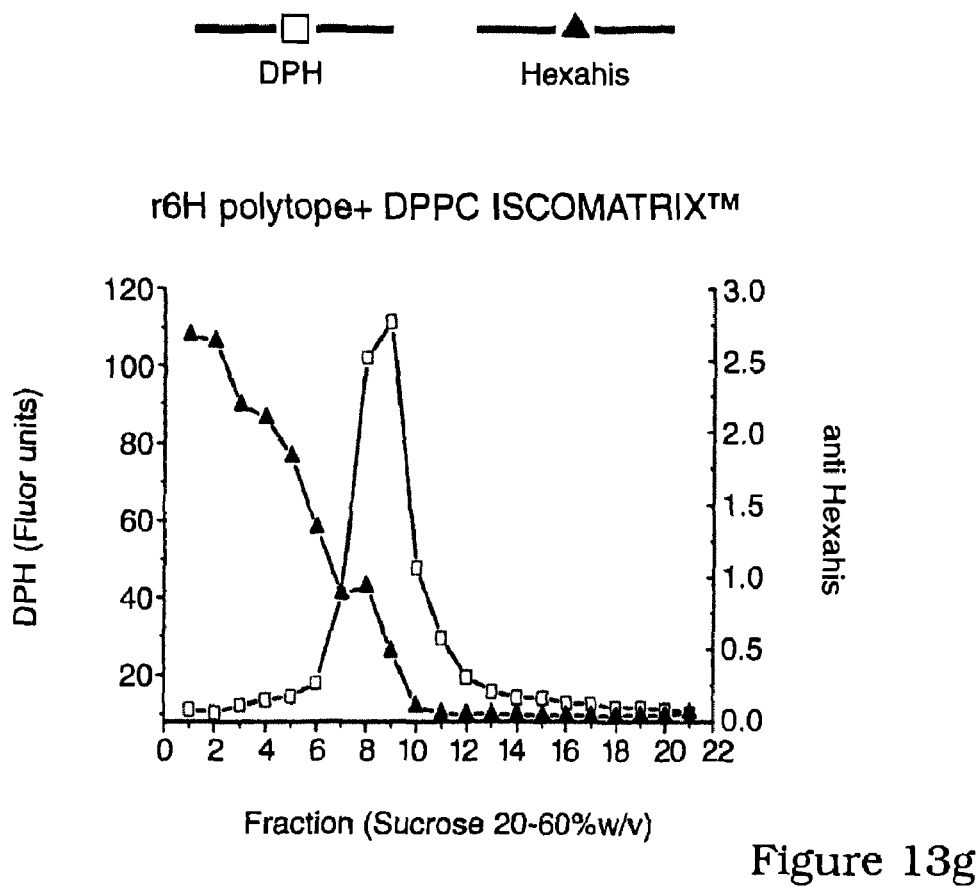
Figure 13H:
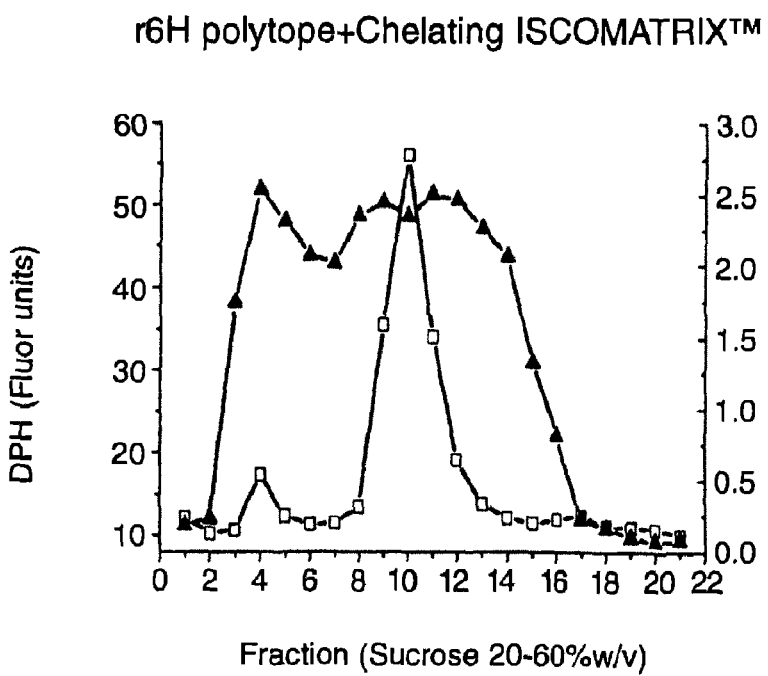
Figure 13I:
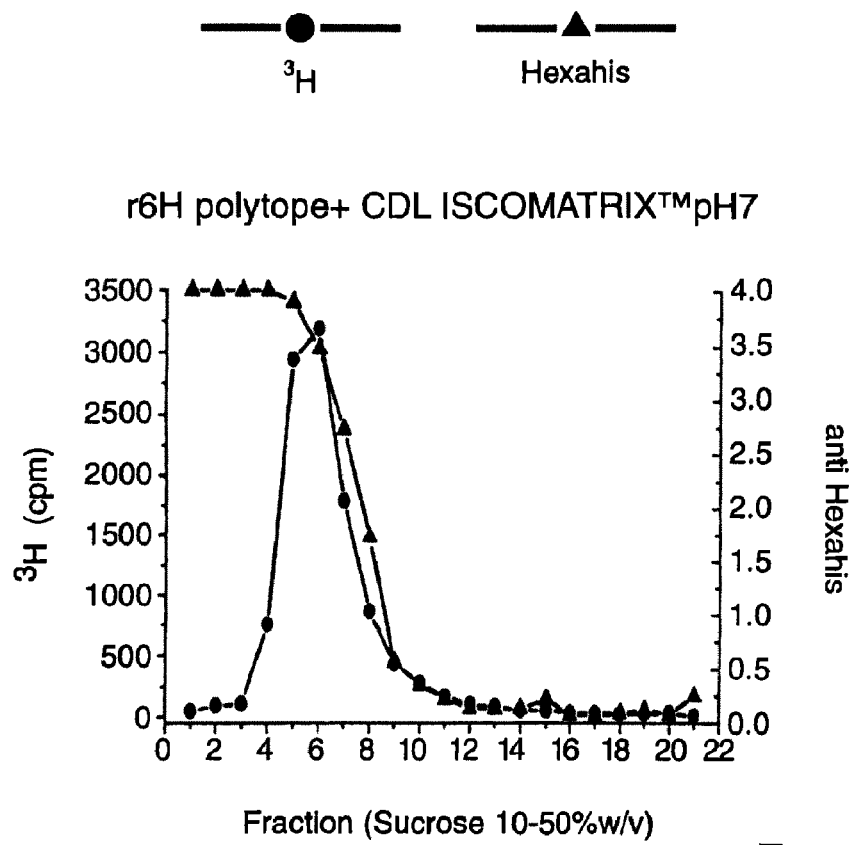
Figure 13J:
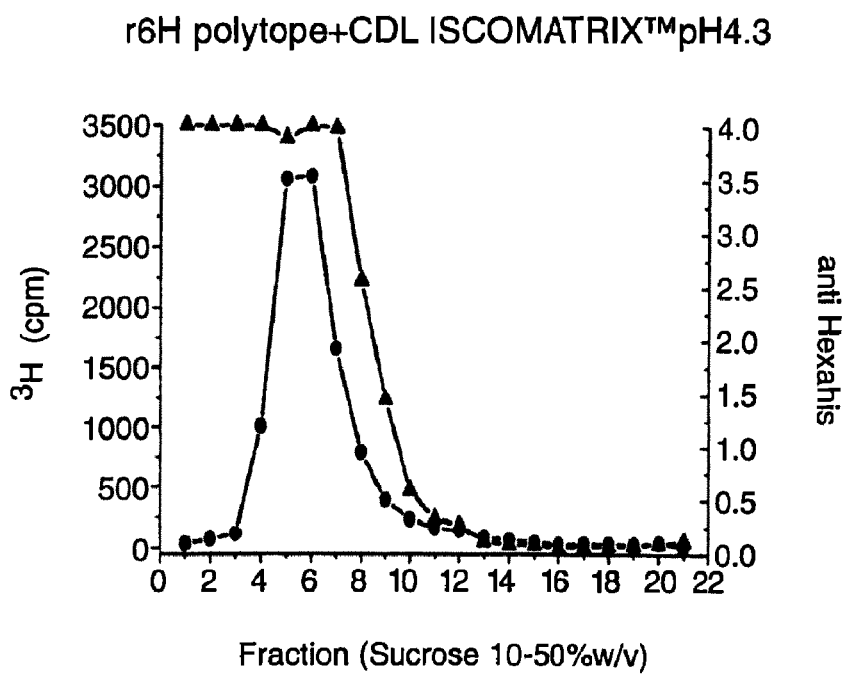
Figure 13K:
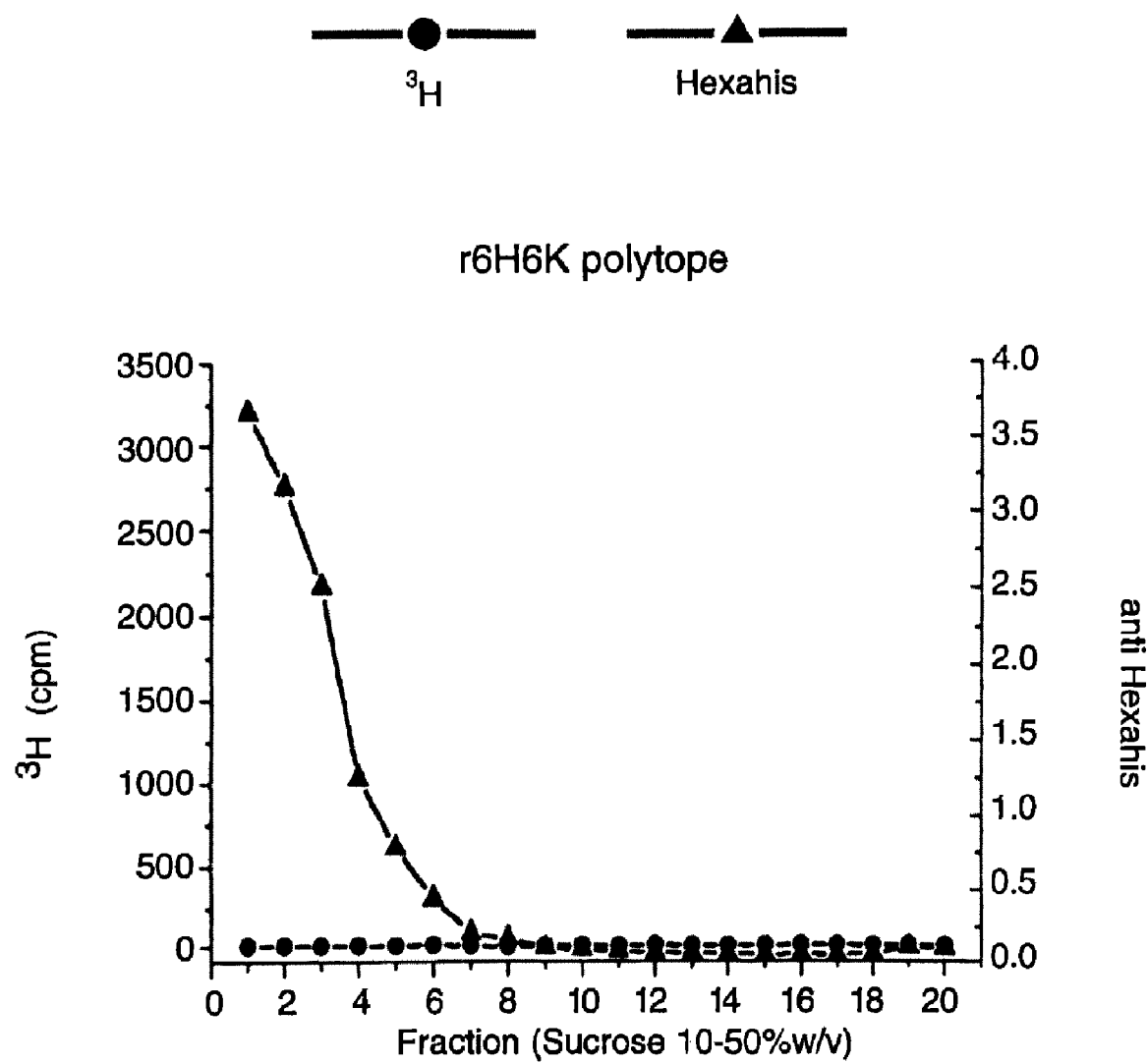

The protein in the r6H6K polytope alone was found in fractions 1-6 (FIG. 13K). The protein in the r6K6H polytope mixed with standard DPPC ISCOMATRIX™ at pH7 was found predominantly in fractions 1-9 with little evidence of association (FIG. 13 A). The protein in the r6K6H polytope mixed with CDL and DPL ISCOMATRIX™ at pH 7 was found predominantly in fractions coinciding with ISCOMATRIX™ indicating association (FIGS. 13 C, E). There was a significant proportion of protein found in fractions 1-3 and 1-6, for CDL and DPL respectively, and probably not associated. The protein in the r6K6H polytope mixed with standard DPPC ISCOMATRIX™ at pH4.3 was found predominantly in fractions 1-9 with some evidence of association in the coinciding ISCOMATRIX™ peak in fractions 10-12 (FIG. 13 B). The protein in the r6K6H polytope mixed with CDL and DPL ISCOMATRIX™ at pH4.3 was almost all found in fractions coinciding with ISCOMATRIX™ indicating almost complete association (FIGS. 13 D, F). The r6H polytope mixed with DPPC ISCOMATRIX™ was found predominanty in fractions 1-7 with little evidence of association. The r6H polytope mixed with CHL ISCOMATRIX™ showed similar patterns of association for standard DPPC and CDL ISCOMATRIX™ at both pH7 and pH4.3. The protein was found in about equal amounts in fractions 1-4 non-associated and 5-10 coinciding with the ISCOMATRIX™ peak indicating association (FIGS. 13 H, I, J).

These results show that the rpolytope used here would not associate with standard ISCOMATRIX™ even with the addition of 6K. Association could be achieved using modified ISCOMATRIX™ and the capacity to associate with these formulations was increased by utilising low pH. The combination of modified ISCOMATRIX™ and low pH resulted in as good as, or better, association than with 6H CHL ISCOMATRIX™ which was not increased by use of modified ISCOMATRIX™ or low pH.

EXAMPLE 17

Immunisation of Mice with rPolytope Associated ISCOMATRIX™ Formulations

Three BALB/c mice were immunized subcutaneously at the base of the tail with 0.1 ml of associated ISCOMATRIX™ containing 6 μg ISCOPREP™ 703 and between 3.5 μg and 5 μg protein.

CTL assays were performed according to the method of Elliott et al. (199°). Briefly, spienocytes from each spleen were removed on day 14 and cultured in 1 ml medium at $5 \times 10^6$ cell/ml, in a24 well plate, together with 1 μg/ml of the individual peptides (4 peptides/spleen) in a humidifed incubator at 37° C. On day 3, 1 ml of fresh media was added and then further in vitro restimulation performed on day 7 by adding irradiated (800 rad) peptide sensitised (10 μg/ml, 1 hr 37° C., 2 washes) P815 cells at a res ponder to stimulator ratio of 20:1 to $2 \times 10^5$ effectors/well. The procedure was repeated twice more at 7 day intervals and the bulk cultures were used as effectors 6 days later in a standard 6 hr chromium release assay. Medium contained RPMI 1640 supplemented with 10% FCS (QIMR), $5 \times 10^{-5}$ M 2-mercaptoethanol, 2 mM glutamine and pen/strep antibiotics. Target cells were $^{51}$Cr labelled peptide sensitised and unsensitised (control) P815 cells. The ratio of effector:target was 50, 10 and 2 to 1. The assays were performed in 96 well round bottom plates in duplicate.

Figure 14A:
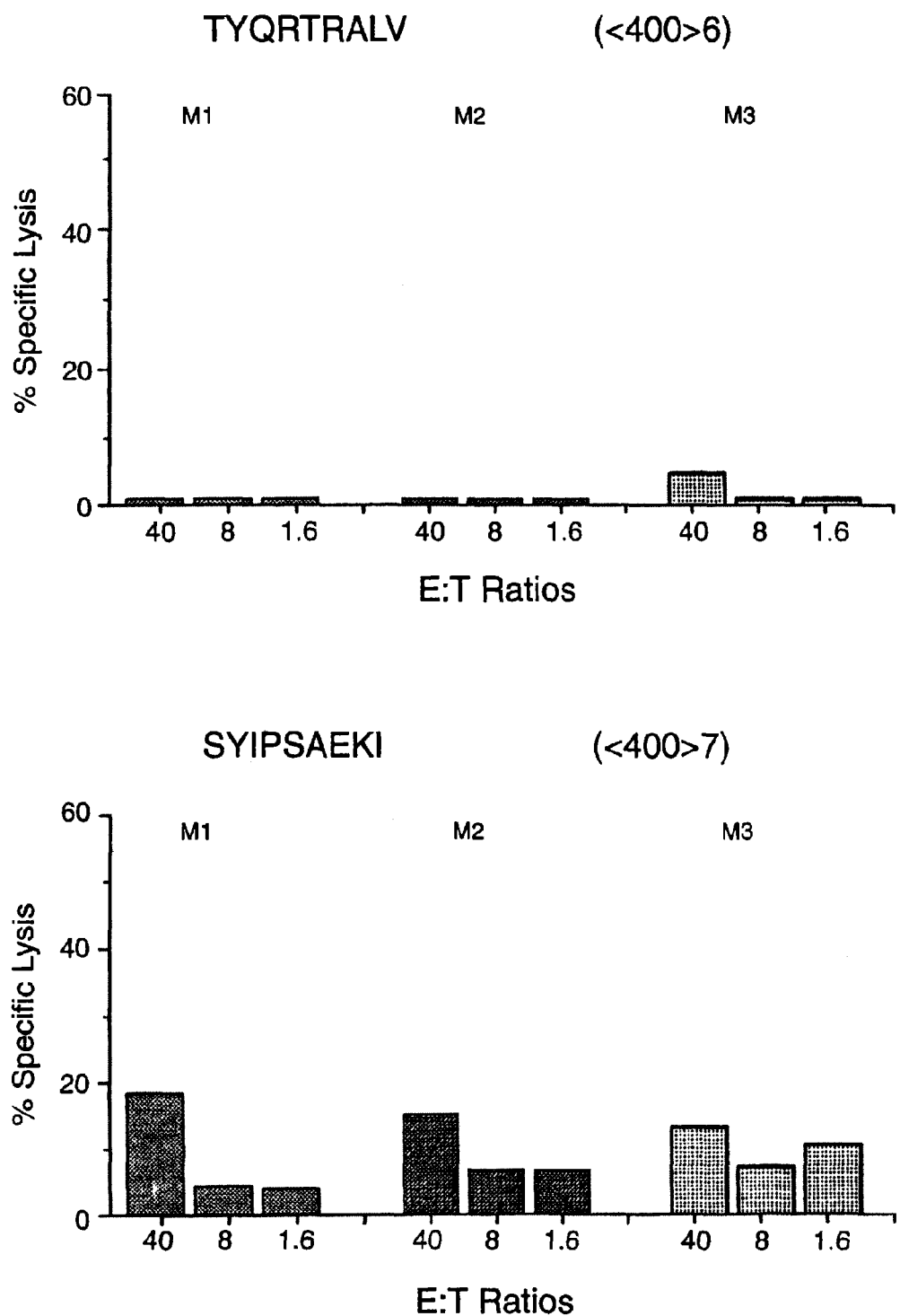
FIG. 14 is a graphical representation of the CTL analysis of the 6K polytope CDL ISCOMATRIX™ pH4.3 (FIG. 14A) and 6H polytope CHL ISCOMATRIX™ (FIG. 14B) formulations. It can be seen that CTL responses were induced to all 4 epitopes in the polytope for both the formulations but the responses were very low to the TYQ epitope.
Figure 14B:
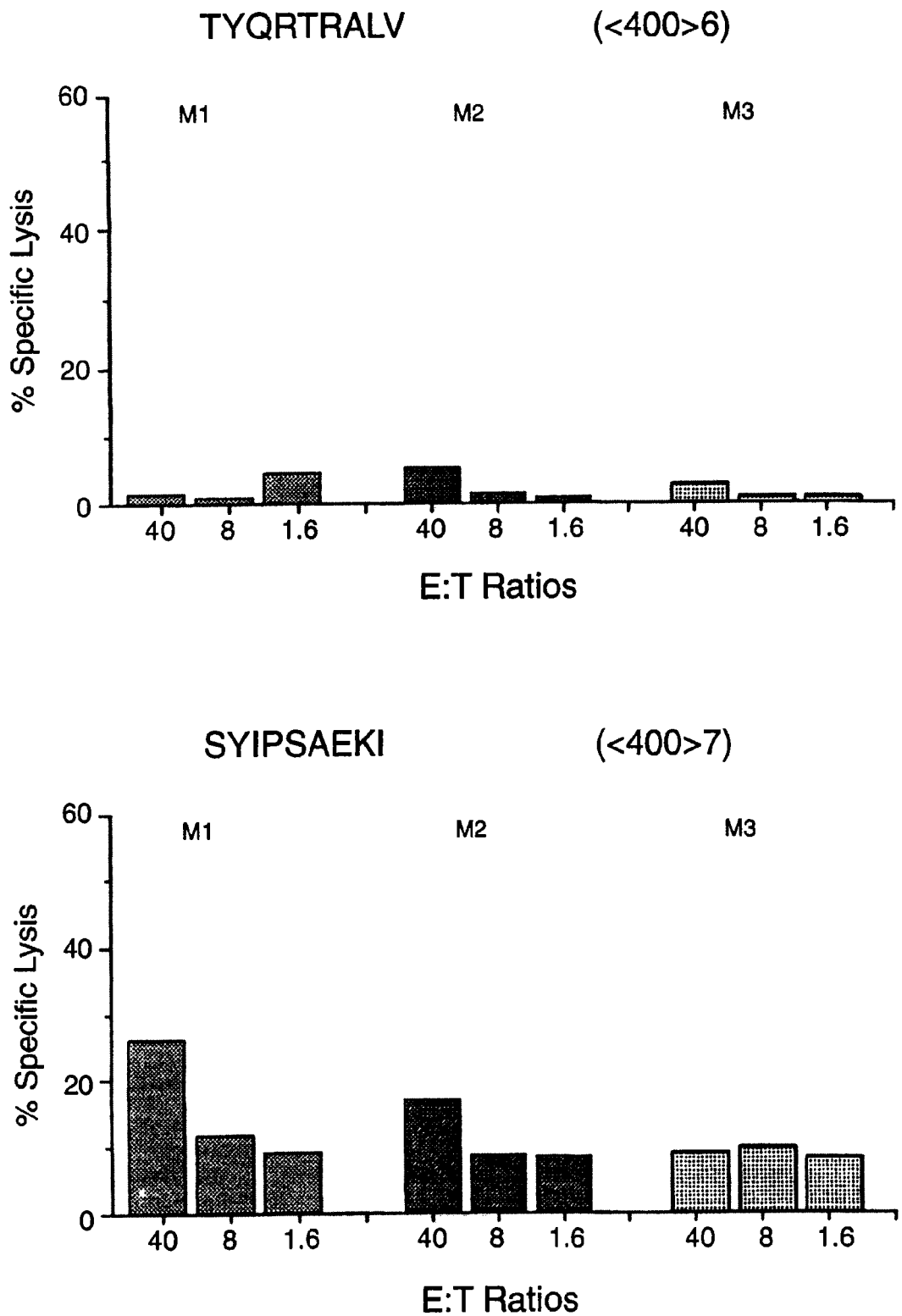

The r6K6H polytope associated CDL ISCOMATRIX™ pH4.3 induced CTL responses in 3/3 mice for the SYI, YPH and RPQ epitopes and in 1/3 for the TYQ epitope (FIG. 14A). The r6H associated CHL ISCOMATRIX™ pH7 induced CTL responses in 3/3 mice for the SYI, YPH and RPQ epitopes and in 2/3 for the TYQ epitope (FIG. 14B). Both formulations induced very low responses to the TYQ epitope.

These results show that CTL responses can be induced using r6K6H polytope associated CDL ISCOMATRIX™ pH4.3 and are comparable to responses with r6H associated CHL ISCOMATRIX™ pH7.

EXAMPLE 18

Preparation of DPPC and DPL Liposomes with a Naturally Negatively Charged Protein: E6E7

Liposomes were prepared according to the method of Talsma and Crommelin (1992). Briefly, $^3$H cholesterol was dissolved in methanol, chloroform then lipid added and liposomes allowed to form by solvent evaporation in a rotaflask with gentle swirling. The lipids used were the standard DPPC and the negatively charged DPL. E6E7 was then added to the liposomes and the mixture sonicated then extruded through a 26G needle. The liposomes were of typical appearance by electron microscopy.

After formulation, preparations were purified on a sucrose gradient (10 to 50% sucrose w/v) and fractions analysed for protein and ISCOMATRIX™ (FIG. 15). Protein was detected by sandwich EIA for E7 using monoclonal antibodies. ISCOMATRIX™ was determined by detection 3H cholesterol.

Figure 15A:
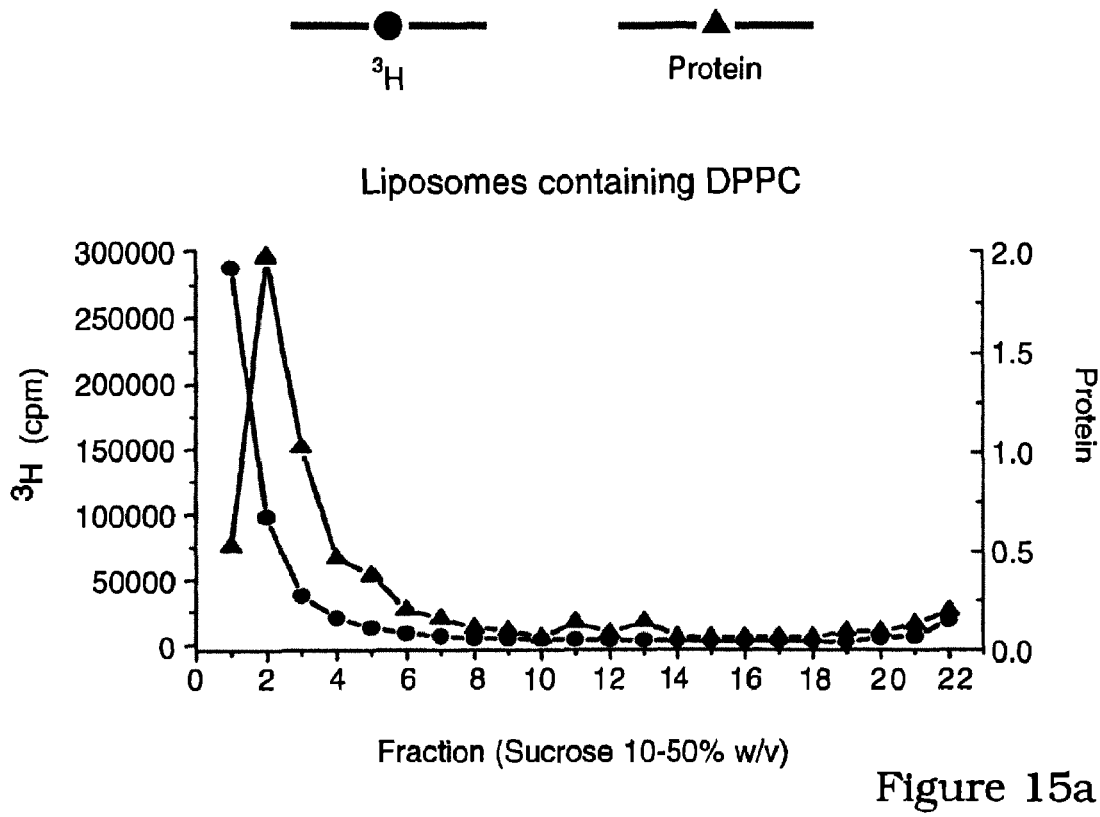
FIG. 15 is a graphical representation of the liposomes mixed with E6E7 from Example 18. It can be seen that most of the E6E7 was associated with the DPL liposomes but very little E6E7 was associated with the DPPC liposomes.
Figure 15B:
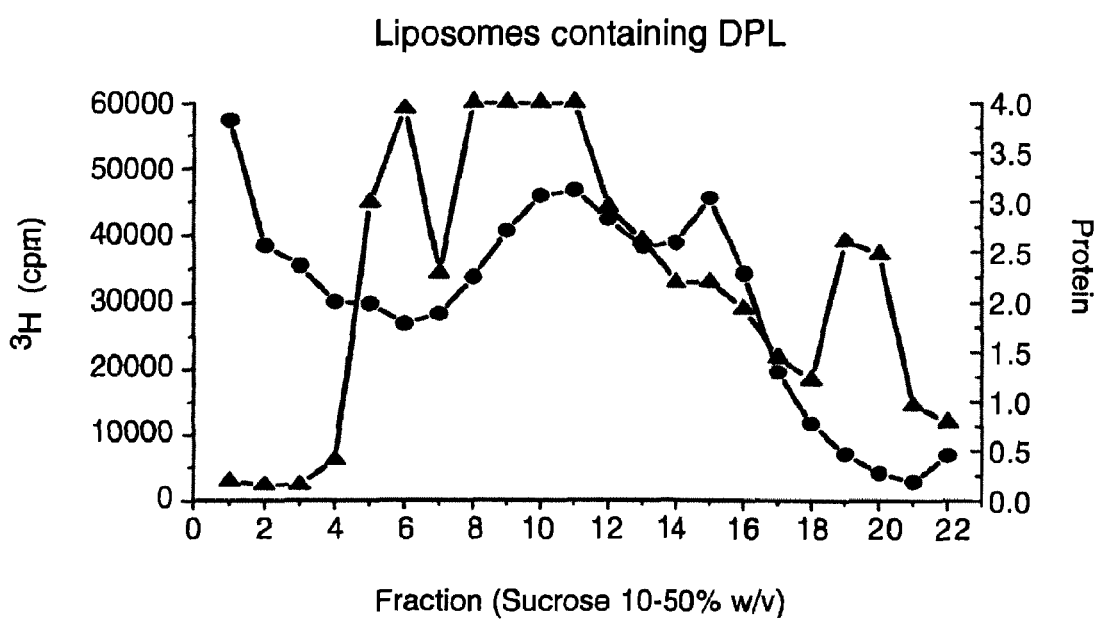

The E6E7 in the DPPC liposomes was found predominantly in fractions 1-3 but very little was present on the gradient which indicated the protein had precipitated (FIG. 15A). The protein that was present was probably not associated with the liposome which was found in fractions 2-4. The E6E7 in the DPL Liposome was found throughout the gradient coinciding with the liposome which was also found throughtout the gradient (FIG. 15B). The spread of the formulation throughout the gradient was probably indicative of a range of sizes of liposomes but almost all of the protein seems to be associated with the liposomes.

These results show that negatively charged lipids can be used in liposomes to allow association with a negatively charged protein which would not associate with standard liposomes.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 2

Cytokine Analysis of E6E7 Associated ISCOMATRIX ™

| Stimulated with | Concentration μg | Cytokine pg/ml | |
|---|---|---|---|
| | | αIFN | IL5 |
| GSTE7 | 5 | 7400 | 140 |
| GSTE7 | 1 | 1050 | 85 |
| ConA | 0.4 | 2130 | 74 |
| RPMI | — | <30 | 4 |

REFERENCES

Bradford, M. M. (1976) *Anal. Biochem,* 36:201-211.
Cox, J. C. and Coulter, A. R. *Advances in Adjuvant Technology and Application in Animal Parasite Control Utilising Biotechnology.* Chapter 4. Editor Yong, W. K. CRC Press, 1992.
Cox, J. C. and Coulter, A. R. (1997) *Vaccine* 15(3):248-256.
Cox, J. C. and Coulter, A. R. (1999) *BioDrugs* 12(6):439-453.
Edwards, S. J., Margetts, M. B., Hocking, D. M., Moloney, M. B. H., Rothel, L. J. and Webb, E. A. (1998). Design of a candidate recombinant therapeutic vaccine or cervical cancer. In: Recent Research Development in Biotechnology & Bioengineering. Editor S. G. Pandalai, Research Signpost, India, 343-356.
Elliot, S. L., Pye, S., Le, T., Mateo, L., Cox, J., Macdonald, L., Scalzo, A. A., Forbes, C. A. and Suhrbier, A. (1999) *Vaccine* 17:2009-2019.
Morein, B., Lövgren, K. and Hoglund, S., (1989), Immunostimulating complex (ISCOM). In "Vaccines: Recent Trends and Progress." G. Gregoriadis, A. C. Allison and G. Poster (Eds), Plenium Press, New York, p153.
Talsma, H. and Crommelin, D. J. A. (1992) *BioPharm, October,* 36-47.
Valerio, R. M., Bray, A. M. and Maeji, N. J., *Int. J. Pept. Prof. Res.* 44:158-165 (1994).

The invention claimed is:

1. A method of making an electrostatically-associated immunogenic complex comprising a negatively-charged organic complex and a positively-charged antigen, consisting essentially of admixing:
   (A) a pre-formed, negatively charged organic complex that comprises a saponin and a sterol, and
   (B) an isolated, positively charged antigen,
   thereby forming an immunogenic complex wherein said organic complex and antigen are associated only by electrostatic interaction.

2. The method according to claim 1 wherein said antigen is a protein or comprises a peptide region.

3. The method according to claim 1 wherein the pre-formed organic complex further comprises a phospholipid.

4. The method according to claim 3 wherein said phospholipid is a phosphoglyceride.

5. The method according to claim 4 wherein the phosphoglyceride is selected from the group consisting of phosphatidyl inositol, phosphatidyl glycerol, phosphatidic acid and cardiolipin.

6. The method according to claim 3 wherein said phospholipid is lipid A.

7. The method according to claim 6 wherein the lipid A is selected from the group consisting of diphosphoryl lipid A and monophosphoryl lipid A.

8. The method according to claim 1, wherein said immunogenic complex induces a cytotoxic T-lymphocyte response when administered to a mammal.

9. The method according to claim 1, wherein said antigen has been modified to increase the degree of its positive charge.

10. The method according to claim 1, wherein said preformed organic complex has been modified to increase the degree of its negative charge.

11. The method according to claim 9, wherein said antigen is a naturally positively charged antigen which has been modified to increase the degree of its positive charge.

12. The method according to claim 9, wherein said antigen has been modified by the addition of polylysine and/or arginine.

13. The method according to claim 10, wherein said preformed organic complex is a naturally negatively charged complex which has been modified to increase the degree of its negative charge.

14. The method according to claim 13, wherein said preformed organic complex has been modified with an anionic surfactant and/or negatively charged lipid.

15. The method according to claim 1, wherein said antigen is a non-amphipathic antigen.

16. The method according to claim 1, wherein said antigen does not comprise a hydrophobic region.

17. The method according to claim 1, wherein said organic complex does not comprise a liposome.

* * * * *

SEQUENCE LISTING

```
<160> NUMBER OF SEQ ID NOS: 13

<210> SEQ ID NO 1
<211> LENGTH: 11
<212> TYPE: PRT
<213> ORGANISM: Unknown Sequence
<220> FEATURE:
<223> OTHER INFORMATION: Description of Unknown Sequence: Mammalian
      peptide sequence

<400> SEQUENCE: 1

Ser Leu Leu Met Trp Ile Thr Gln Cys Phe Leu
 1               5                  10

<210> SEQ ID NO 2
<211> LENGTH: 9
<212> TYPE: PRT
<213> ORGANISM: Unknown Organism
<220> FEATURE:
<223> OTHER INFORMATION: Description of Unknown Organism: Mammalian
      peptide sequence

<400> SEQUENCE: 2

Ser Leu Leu Met Trp Ile Thr Gln Cys
 1               5

<210> SEQ ID NO 3
<211> LENGTH: 36
<212> TYPE: PRT
<213> ORGANISM: Artificial Sequence
<220> FEATURE:
<223> OTHER INFORMATION: Description of Artificial Sequence: Synthetic
      polytope peptide

<400> SEQUENCE: 3

Tyr Pro His Phe Met Pro Thr Asn Leu Arg Pro Gln Ala Ser Gly Val
 1               5                  10                  15

Tyr Met Thr Tyr Gln Arg Thr Arg Ala Leu Val Ser Tyr Ile Pro Ser
                20                  25                  30

Ala Glu Lys Ile
            35

<210> SEQ ID NO 4
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      polytope peptide

<400> SEQUENCE: 4

Tyr Pro His Phe Met Pro Thr Asn Leu
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      polytope peptide

<400> SEQUENCE: 5

Arg Pro Gln Ala Ser Gly Val Tyr Met
 1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      polytope peptide

<400> SEQUENCE: 6

Thr Tyr Gln Arg Thr Arg Ala Leu Val
 1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      polytope peptide

<400> SEQUENCE: 7

Ser Tyr Ile Pro Ser Ala Glu Lys Ile
 1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Asx Gln Cys Ala
 1               5

<210> SEQ ID NO 9
<211> LENGTH: 57
<212> TYPE: PRT
<213> ORGANISM: Artificial Sequence
<220> FEATURE:
<223> OTHER INFORMATION: Description of Artificial Sequence: Synthetic
      polytope peptide

<400> SEQUENCE: 9

Tyr Pro His Phe Met Pro Thr Asn Leu Thr Ser Ser Gly Pro Ser Asn
 1               5                  10                  15
```

```
Thr Pro Pro Glu Ile Phe Ala Pro Gly Asn Tyr Pro Ala Leu Ser Tyr
            20                  25                  30

Ile Pro Ser Ala Glu Lys Ile Glu Glu Gly Ala Ile Val Gly Glu Ile
        35                  40                  45

Arg Pro Gln Ala Ser Gly Val Tyr Met
        50                  55

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: 6-His tag

<400> SEQUENCE: 10

His His His His His His
 1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: 6-Lys tag

<400> SEQUENCE: 11

Lys Lys Lys Lys Lys Lys
 1               5

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: 6K6H-tag

<400> SEQUENCE: 12

Lys Lys Lys Lys Lys Lys His His His His His His
 1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: 6H6K-tag

<400> SEQUENCE: 13

His His His His His His Lys Lys Lys Lys Lys Lys
 1               5                   10
```